(12) United States Patent
Stepanov et al.

(10) Patent No.: US 12,111,319 B2
(45) Date of Patent: Oct. 8, 2024

(54) ARTICLES AND METHODS DIRECTED TO PERSONALIZED THERAPY OF CANCER

(71) Applicants: HESPERIX SA, Viganello (CH); THE SCRIPPS RESEARCH INSTITUTE, La Jolla, CA (US)

(72) Inventors: Alexey Vyacheslavovich Stepanov, Moscow (RU); Dmitry Dmitrievich Genkin, St. Petersburg (RU); Alexander Gabibovich Gabibov, Moscow (RU); Richard A. Lerner, La Jolla, CA (US); Alexey Anatolievich Belogurov, Moscow (RU); Jia Xie, San Diego, CA (US)

(73) Assignees: HESPERIX SA, Viganello (CH); THE SCRIPPS RESEARCH INSTITUTE, La Jolla, CA (US)

( * ) Notice: Subject to any disclaimer, the term of this patent is extended or adjusted under 35 U.S.C. 154(b) by 259 days.

(21) Appl. No.: 17/385,834

(22) Filed: Jul. 26, 2021

(65) Prior Publication Data

US 2022/0018845 A1    Jan. 20, 2022

Related U.S. Application Data

(63) Continuation of application No. 16/983,491, filed on Aug. 3, 2020, now Pat. No. 11,215,618, which is a continuation of application No. 16/753,635, filed as application No. PCT/RU2018/000653 on Oct. 4, 2018, now abandoned.

(30) Foreign Application Priority Data

Oct. 4, 2017   (RU) .......................... RU2017134483
Apr. 4, 2018   (RU) .......................... RU2018112009

(51) Int. Cl.
| | | |
|---|---|---|
| *G01N 33/574* | (2006.01) | |
| *A61K 35/17* | (2015.01) | |
| *A61K 39/00* | (2006.01) | |
| *C07K 16/28* | (2006.01) | |
| *C12Q 1/6886* | (2018.01) | |
| *G01N 33/50* | (2006.01) | |
| *G01N 33/543* | (2006.01) | |

(52) U.S. Cl.
CPC ....... *G01N 33/57492* (2013.01); *A61K 35/17* (2013.01); *A61K 39/0011* (2013.01); *C07K 16/2803* (2013.01); *C12Q 1/6886* (2013.01); *G01N 33/505* (2013.01); *G01N 33/543* (2013.01); *A61K 2039/5156* (2013.01); *A61K 2039/5158* (2013.01); *A61K 2039/54* (2013.01); *C07K 2317/24* (2013.01); *C07K 2317/53* (2013.01); *C07K 2317/73* (2013.01); *C07K 2319/03* (2013.01); *C07K 2319/33* (2013.01); *C12Q 2600/156* (2013.01)

(58) Field of Classification Search
None
See application file for complete search history.

(56) References Cited

FOREIGN PATENT DOCUMENTS

| WO | WO-2016198566 A1 * | 12/2016 | ............. A61K 45/00 |
| WO | WO-2019070161 A2 * | 4/2019 | ............. A61K 35/17 |

OTHER PUBLICATIONS

Ray, 2017, Progress Biophys and Mol. Biol. vol. 128: 74-84.*
Hanssens, 2021, Med. Res. Rev. vol. 42: 306-342.*
Schulze, 2018, ACS Chem. Biol. vol. 13: 3229-3235.*

* cited by examiner

*Primary Examiner* — Amy E Juedes
(74) *Attorney, Agent, or Firm* — ENTRALTA PLLC; James F. Fleming; Peter D. Weinstein

(57) ABSTRACT

Described are methods for providing personalized medicine for the treatment of B cell malignancies including lymphoma. The methods make use of Chimeric Antigen Receptor (CAR) technology.

10 Claims, 22 Drawing Sheets

Specification includes a Sequence Listing.

|  IL-2 signal sequence | | 7aa cyclopeptide library | G₃S | | |
|---|---|---|---|---|---|
| MYRMQLLSCI | ALSLALVTNS | ACXXXXXXXC | GGGSASEPKS | CDKTHTCPPC | |
| PAPPVAGPSV | FLFPPKPKDT | LMIARTPEVT | CVVVDVSHED | PEVKFNWYVD | IgG1 hinge |
| GVEVHNAKTK | PREEQYQSTY | RVVSVLTVLH | QDWLNGKEYK | CKVSNKALPA | |
| PIEKTISKAK | GQPREPQVYT | LPPSRDELTK | NQVSLTCLVK | GFYPSDIAVE | |
| WESNGQPENN | YKTTPPVLDS | DGSFFLYSKL | TVDKSRWQQG | NVFSCSVMHE | |
| | | linker | | | |
| ALHNHYTQKS | LSLSPGKGST | SGSGKPGSGE | GSTKGPWVLV | VVGGVLACYS | CD28 |
| LLVTVAFIIF | WVRSKRSRLL | HSDYMNMTFR | RPGPTRKHYQ | PYAPPRDFAA | |
| | | OX-40 | | | |
| YRSRDQRLPP | DAHKPPGGGS | FRTPIQEEQA | DAHSTLAKIR | VKFSRSADAP | CD3 zeta |
| AYQQGQNQLY | NELNLGRREE | YDVLDKRRGR | DPEMGGKPRR | KNPQEGLYNE | |
| LQKDKMAEAY | SEIGMKGERR | RGKGHDGLYQ | GLSTATKDTY | DALHMQALPP | |
| R | | | | | |

FIG. 5A

```
                IL-2 signal sequence
MYRMQLLSCI    ALSLALVTNS    AAQPAISREV    QLVESGGDLV    QPGGSLRLSC  ⎫
VASGFNFSNF    TMNWVRQAPG    KGLEWLSNIS    RNGSDKYYAD    SVKGRFNISR  ⎬ Lymphoma BCR VH
DNGNNSLYL     QMNRLKDEDTA   VYYCAKNRSD    SGSNQRFFDY    WGQGTLVTVS  ⎭
                linker
SASLGGGGS     GGGGSGGGGST   SYELMQPPSV    SVSPGQTASI    TCSGDKLGDK  ⎫
YVSWYQQKA     GQPLLLVIYQD   DKRPSGITER    FSGSNSGNTA    TLTISGAQAM  ⎬ Lymphoma BCR VL
DEADYFCQA     WDSNIYVFGSG   TKVTVLGGAL    GLGGLASEPK    SCDKTHTCPP  ⎭
CPAPELLGG     PSVFLFPPKPK   DTLMISRTPE    VTCVVVDVSH    EDPEVKFNWY  ⎫
VDGVEVHNA     KTKPREEQYNS   TYRVVSVLTV    LHQDWLNGKE    YKCKVSNKAL  ⎬ IgG1 hinge
RAPIEKTIS     KAKGQPREPQV   YTLPPSRDEL    TKNQVSLTCL    VKGFYPSDIA  ⎭
VEWESNGQP     ENNYKTTPPVL   DSDGSFFLYS    KLTVDKSRWQ    QGNVFSCSVM
                                            linker           TEV site
HEALHNHYT     QKSLSLSPGK    STSGSGKPGS    GEGSTKGENL    YFQGDLNAVG  ⎫
QDTAVGQDT     QEVIVVPHSLP   FKVVVISAIL    ALVVLTIISL    IILIMLWQKK  ⎬ PDGFR TM
FRIGIR                                                              ⎭
```

FIG. 5B

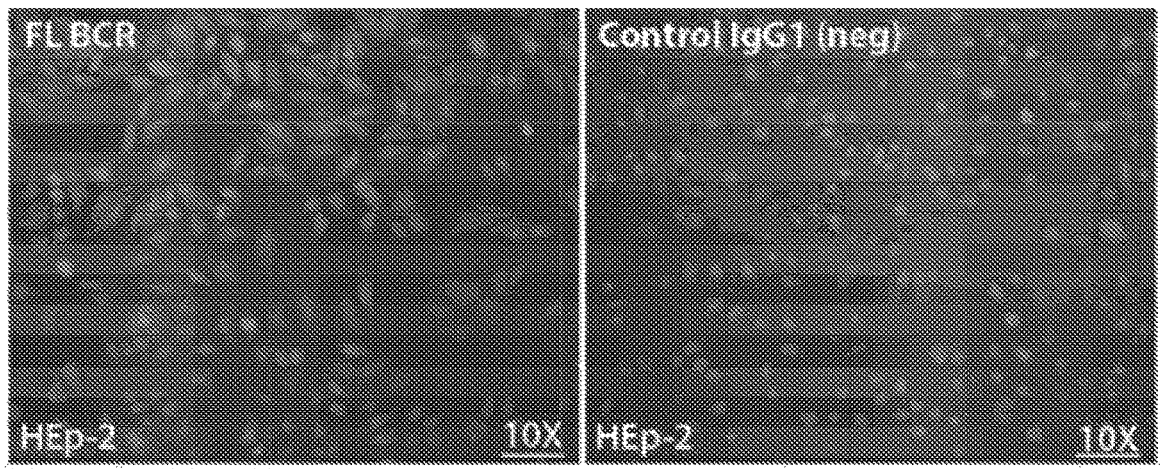
FIG. 8C
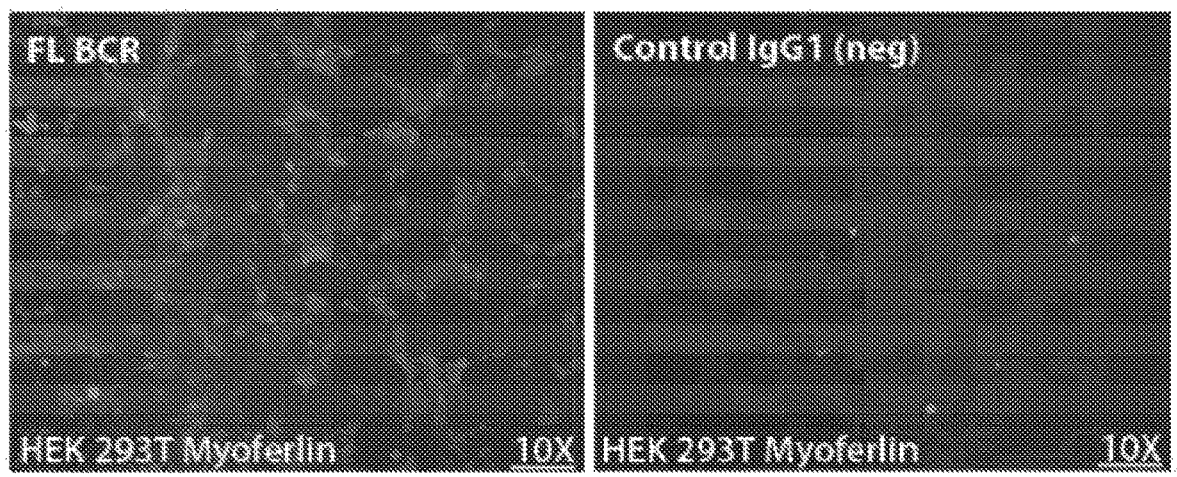
FIG. 8D
```
         CILDLPKFC                    FL patient BCR specific cyclopeptide
.1984 GKGRDEPNMNPKLDLPNRPETDPLWFTN 2010. Myoferlin, Homo sapiens
...77 KQSKIVSVVPNILDLPKFEGTTEWIDVN 104.. Surface protein, Streptococcus mitis
..424 YSSIDSIFYEGILDLPKFRYFISGKDIS 451.. Surface protein, Pneumocystis jirovecii
```
FIG. 8E Ph.D.-C7C:  GCT TGT (NNK)₇ TGC GGT GGA GGT
            CGA ACA (NNM)₇ ACG CCA CCT CCA
            Ala Cys  Xxx₇  Cys Gly Gly Gly

SEQUENCE LISTING

```
<160> NUMBER OF SEQ ID NOS: 44

<210> SEQ ID NO 1
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 1

Cys Ile Leu Asp Leu Pro Lys Phe Cys
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic polypeptide
```

```
<400> SEQUENCE: 2

Cys Met Pro His Trp Gln Asn His Cys
1               5

<210> SEQ ID NO 3
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 3

Cys Thr Thr Asp Gln Ala Arg Lys Cys
1               5

<210> SEQ ID NO 4
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 4
atggactgga cctggaggat cct                                         23

<210> SEQ ID NO 5
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 5
atggacatac tttgttccac gctc                                        24

<210> SEQ ID NO 6
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 6
atggagtttg ggctgagctg g                                           21

<210> SEQ ID NO 7
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 7
atgaaacacc tgtggttctt cct                                         23

<210> SEQ ID NO 8
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 8
atggggtcaa ccgccatcct c                                           21
```

```
<210> SEQ ID NO 9
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 9
atgtctgtct ccttcctcat cttc                                    24

<210> SEQ ID NO 10
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 10
ctctcaggac tgatgggaag cc                                      22

<210> SEQ ID NO 11
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 11
ggagacgagg gggaaaag                                           18

<210> SEQ ID NO 12
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 12
gcctgagttc cacgacacc                                          19

<210> SEQ ID NO 13
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 13 caggggaag accgatgg                                            18

<210> SEQ ID NO 14
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 14
gacatccaga tgacccagtc tcc                                     23

<210> SEQ ID NO 15
<211> LENGTH: 24
<212> TYPE: DNA
<213> ORGANISM: Artificial Sequence
<220> FEATURE:
<223> OTHER INFORMATION: Synthetic polynucleotide
```

```
<400> SEQUENCE: 15
gatattgtga tgacccagac tcca                                          24

<210> SEQ ID NO 16
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 16
gaaattgtgt tgacacagtc tcca                                          24

<210> SEQ ID NO 17
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 17
cccctgttga agctctttgt                                               20

<210> SEQ ID NO 18
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 18
agatggcggg aagatgaag                                                19

<210> SEQ ID NO 19
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 19
cagtctgtgt tgacgcagcc gccctc                                        26

<210> SEQ ID NO 20
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 20
tctgtgctga ctcagccacc ctc                                           23

<210> SEQ ID NO 21
<211> LENGTH: 26
<212> TYPE: DNA
<213> ORGANISM: Artificial Sequence
<220> FEATURE:
<223> OTHER INFORMATION: Synthetic polynucleotide

<400> SEQUENCE: 21
cagtctgtcg tgacgcagcc gccctc                                        26

<210> SEQ ID NO 22
<211> LENGTH: 26
```

```
<212> TYPE: DNA
<213> ORGANISM: Artificial Sequence
<220> FEATURE:
<223> OTHER INFORMATION: Synthetic polynucleotide

<400> SEQUENCE: 22
tccgtgtccg ggtctcctgg acagtc                                           26

<210> SEQ ID NO 23
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 23
actcagccac cctcggtgtc agtg                                             24

<210> SEQ ID NO 24
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 24
tcctctgcct ctgcttccct ggga                                             24

<210> SEQ ID NO 25
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 25
cagcctgtgc tgactcagcc                                                  20

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 26
gtgtggcctt gttggcttg                                                   19

<210> SEQ ID NO 27
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 27 cgaggggggca gccttggg                                                   18

<210> SEQ ID NO 28
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 28
```

```
agtgaccgtg gggttggcct tggg                                          24
```

<210> SEQ ID NO 29
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 29

```
Ala Cys Ile Leu Asp Leu Pro Lys Phe Cys Gly Gly Gly Ser
1               5                   10
```

<210> SEQ ID NO 30
<211> LENGTH: 14
<212> TYPE: PRT
<213> ORGANISM: Artificial Sequence
<220> FEATURE:
<223> OTHER INFORMATION: Synthetic polypeptide

<400> SEQUENCE: 30

```
Leu Glu Glu Lys Lys Gly Asn Tyr Val Val Thr Asp His Cys
1               5                   10
```

<210> SEQ ID NO 31
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 31

```
Cys Ile Leu Asp Leu Pro Lys Phe Cys
1               5
```

<210> SEQ ID NO 32
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 32

```
Thr Gly Thr Ala Thr Thr Cys Thr Thr Gly Ala Thr Thr Gly Cys
1               5                   10                  15

Cys Gly Ala Ala Gly Thr Thr Thr Gly Cys
            20                  25
```

<210> SEQ ID NO 33
<211> LENGTH: 501
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (23)..(29)
<223> OTHER INFORMATION: Xaa can be any naturally occurring amino acid

<400> SEQUENCE: 33

```
Met Tyr Arg Met Gln Leu Leu Ser Cys Ile Ala Leu Ser Leu Ala Leu
1               5                   10                  15

Val Thr Asn Ser Ala Cys Xaa Xaa Xaa Xaa Xaa Xaa Cys Gly Gly
            20                  25                  30

Gly Ser Ala Ser Glu Pro Lys Ser Cys Asp Lys Thr His Thr Cys Pro
        35                  40                  45
```

-continued

```
Pro Cys Pro Ala Pro Val Ala Gly Pro Ser Val Phe Leu Phe Pro
    50              55              60

Pro Lys Pro Lys Asp Thr Leu Met Ile Ala Arg Thr Pro Glu Val Thr
65              70              75              80

Cys Val Val Asp Val Ser His Glu Asp Pro Glu Val Lys Phe Asn
            85              90              95

Trp Tyr Val Asp Gly Val Glu Val His Asn Ala Lys Thr Lys Pro Arg
            100             105             110

Glu Glu Gln Tyr Gln Ser Thr Tyr Arg Val Val Ser Val Leu Thr Val
            115             120             125

Leu His Gln Asp Trp Leu Asn Gly Lys Glu Tyr Lys Cys Lys Val Ser
    130             135             140

Asn Lys Ala Leu Pro Ala Pro Ile Glu Lys Thr Ile Ser Lys Ala Lys
145             150             155             160

Gly Gln Pro Arg Glu Pro Gln Val Tyr Thr Leu Pro Pro Ser Arg Asp
            165             170             175

Glu Leu Thr Lys Asn Gln Val Ser Leu Thr Cys Leu Val Lys Gly Phe
            180             185             190

Tyr Pro Ser Asp Ile Ala Val Glu Trp Glu Ser Asn Gly Gln Pro Glu
            195             200             205

Asn Asn Tyr Lys Thr Thr Pro Pro Val Leu Asp Ser Asp Gly Ser Phe
    210             215             220

Phe Leu Tyr Ser Lys Leu Thr Val Asp Lys Ser Arg Trp Gln Gln Gly
225             230             235             240

Asn Val Phe Ser Cys Ser Val Met His Glu Ala Leu His Asn His Tyr
            245             250             255

Thr Gln Lys Ser Leu Ser Leu Ser Pro Gly Lys Gly Ser Thr Ser Gly
            260             265             270

Ser Gly Lys Pro Gly Ser Gly Glu Gly Ser Thr Lys Gly Phe Trp Val
            275             280             285

Leu Val Val Gly Gly Val Leu Ala Cys Tyr Ser Leu Leu Val Thr
    290             295             300

Val Ala Phe Ile Ile Phe Trp Val Arg Ser Lys Arg Ser Arg Leu Leu
305             310             315             320

His Ser Asp Tyr Met Asn Met Thr Pro Arg Arg Pro Gly Pro Thr Arg
            325             330             335

Lys His Tyr Gln Pro Tyr Ala Pro Pro Arg Asp Phe Ala Ala Tyr Arg
            340             345             350

Ser Arg Asp Gln Arg Leu Pro Pro Asp Ala His Lys Pro Pro Gly Gly
            355             360             365

Gly Ser Phe Arg Thr Pro Ile Gln Glu Glu Gln Ala Asp Ala His Ser
    370             375             380

Thr Leu Ala Lys Ile Arg Val Lys Phe Ser Arg Ser Ala Asp Ala Pro
385             390             395             400

Ala Tyr Gln Gln Gly Gln Asn Gln Leu Tyr Asn Glu Leu Asn Leu Gly
            405             410             415

Arg Arg Glu Glu Tyr Asp Val Leu Asp Lys Arg Arg Gly Arg Asp Pro
            420             425             430

Glu Met Gly Gly Lys Pro Arg Arg Lys Asn Pro Gln Glu Gly Leu Tyr
            435             440             445

Asn Glu Leu Gln Lys Asp Lys Met Ala Glu Ala Tyr Ser Glu Ile Gly
    450             455             460
```

```
Met Lys Gly Glu Arg Arg Gly Lys Gly His Asp Gly Leu Tyr Gln
465                 470                 475                 480

Gly Leu Ser Thr Ala Thr Lys Asp Thr Tyr Asp Ala Leu His Met Gln
            485                 490                 495

Ala Leu Pro Pro Arg
            500

<210> SEQ ID NO 34
<211> LENGTH: 607
<212> TYPE: PRT
<213> ORGANISM: Artificial Sequence
<220> FEATURE:
<223> OTHER INFORMATION: Synthetic polypeptide

<400> SEQUENCE: 34

Met Tyr Arg Met Gln Leu Leu Ser Cys Ile Ala Leu Ser Leu Ala Leu
1               5                   10                  15

Val Thr Asn Ser Ala Ala Gln Pro Ala Ile Ser Arg Glu Val Gln Leu
            20                  25                  30

Val Glu Ser Gly Gly Asp Leu Val Gln Pro Gly Gly Ser Leu Arg Leu
        35                  40                  45

Ser Cys Val Ala Ser Gly Phe Asn Phe Ser Asn Phe Thr Met Asn Trp
50                  55                  60

Val Arg Gln Ala Pro Gly Lys Gly Leu Glu Trp Leu Ser Asn Ile Ser
65                  70                  75                  80

Arg Asn Gly Ser Asp Lys Tyr Tyr Ala Asp Ser Val Lys Gly Arg Phe
                85                  90                  95

Asn Ile Ser Arg Asp Asn Gly Asn Ser Leu Tyr Leu Gln Met Asn
            100                 105                 110

Arg Leu Lys Asp Glu Asp Thr Ala Val Tyr Tyr Cys Ala Lys Asn Arg
        115                 120                 125

Ser Asp Ser Gly Ser Asn Gln Arg Phe Phe Asp Tyr Trp Gly Gln Gly
130                 135                 140

Thr Leu Val Thr Val Ser Ser Ala Ser Leu Gly Gly Gly Ser Gly
145                 150                 155                 160

Gly Gly Gly Ser Gly Gly Gly Ser Thr Ser Tyr Glu Leu Met Gln
                165                 170                 175

Pro Pro Ser Val Ser Val Ser Pro Gly Gln Thr Ala Ser Ile Thr Cys
            180                 185                 190

Ser Gly Asp Lys Leu Gly Asp Lys Tyr Val Ser Trp Tyr Gln Gln Lys
        195                 200                 205

Ala Gly Gln Pro Leu Leu Val Ile Tyr Gln Asp Asp Val Arg Pro
210                 215                 220

Ser Gly Ile Thr Glu Arg Phe Ser Gly Ser Asn Ser Gly Asn Thr Ala
225                 230                 235                 240

Thr Leu Thr Ile Ser Gly Ala Gln Ala Met Asp Glu Ala Asp Tyr Phe
                245                 250                 255

Cys Gln Ala Trp Asp Ser Asn Ile Tyr Val Phe Gly Ser Gly Thr Lys
            260                 265                 270

Val Thr Val Leu Gly Gly Ala Leu Gly Leu Gly Gly Leu Ala Ser Glu
        275                 280                 285

Pro Lys Ser Cys Asp Lys Thr His Thr Cys Pro Pro Cys Pro Ala Pro
290                 295                 300

Glu Leu Leu Gly Gly Pro Ser Val Phe Leu Phe Pro Pro Lys Pro Lys
305                 310                 315                 320
```

-continued

```
Asp Thr Leu Met Ile Ser Arg Thr Pro Glu Val Thr Cys Val Val Val
            325                 330                 335

Asp Val Ser His Glu Asp Pro Glu Val Lys Phe Asn Tyr Trp Tyr Val
        340                 345                 350

Asp Gly Val Glu Val His Asn Ala Lys Thr Lys Pro Arg Glu Glu Gln
    355                 360                 365

Tyr Asn Ser Thr Tyr Arg Val Val Ser Val Leu Thr Val Leu His Gln
370                 375                 380

Asp Trp Leu Asn Gly Lys Glu Tyr Lys Cys Lys Val Ser Asn Lys Ala
385                 390                 395                 400

Leu Pro Ala Pro Ile Glu Lys Thr Ile Ser Lys Ala Lys Gly Gln Pro
                405                 410                 415

Arg Glu Pro Gln Val Tyr Thr Leu Pro Pro Ser Arg Asp Glu Leu Thr
            420                 425                 430

Lys Asn Gln Val Ser Leu Thr Cys Leu Val Lys Gly Phe Tyr Pro Ser
        435                 440                 445

Asp Ile Ala Val Glu Trp Glu Ser Asn Gly Gln Pro Glu Asn Asn Tyr
    450                 455                 460

Lys Thr Thr Pro Pro Val Leu Asp Ser Asp Gly Ser Phe Phe Leu Tyr
465                 470                 475                 480

Ser Lys Leu Thr Val Asp Lys Ser Arg Trp Gln Gln Gly Asn Val Phe
                485                 490                 495

Ser Cys Ser Val Met His Glu Ala Leu His Asn His Tyr Thr Gln Lys
            500                 505                 510

Ser Leu Ser Leu Ser Pro Gly Lys Gly Ser Thr Ser Gly Ser Gly Lys
        515                 520                 525

Pro Gly Ser Gly Glu Gly Ser Thr Lys Gly Glu Asn Leu Tyr Phe Gln
    530                 535                 540

Gly Asp Leu Asn Ala Val Gly Gln Asp Thr Ala Val Gly Gln Asp Thr
545                 550                 555                 560

Gln Glu Val Ile Val Val Pro His Ser Leu Pro Phe Lys Val Val Val
                565                 570                 575

Ile Ser Ala Ile Leu Ala Leu Val Val Leu Thr Ile Ile Ser Leu Ile
            580                 585                 590

Ile Leu Ile Met Leu Trp Gln Lys Lys Pro Arg Ile Gly Ile Arg
        595                 600                 605

<210> SEQ ID NO 35
<211> LENGTH: 28
<212> TYPE: PRT
<213> ORGANISM: Homo Sapiens

<400> SEQUENCE: 35

Gly Lys Gly Arg Asp Glu Pro Asn Met Asn Pro Lys Leu Asp Leu Pro
1               5                   10                  15

Asn Arg Pro Glu Thr Ser Phe Leu Trp Phe Thr Asn
            20                  25

<210> SEQ ID NO 36
<211> LENGTH: 28
<212> TYPE: PRT
<213> ORGANISM: Streptococcus mitis

<400> SEQUENCE: 36

Lys Gln Ser Lys Ile Val Ser Val Val Pro Asn Ile Leu Asp Leu Pro
1               5                   10                  15
```

```
Lys Phe Glu Gly Thr Thr Glu Trp Ile Asp Val Asn
            20                  25

<210> SEQ ID NO 37
<211> LENGTH: 28
<212> TYPE: PRT
<213> ORGANISM: Pneumocystis jirovecii

<400> SEQUENCE: 37

Tyr Ser Ser Ile Asp Ser Ile Phe Tyr Glu Gly Ile Leu Asp Leu Pro
1               5                   10                  15

Lys Phe Arg Tyr Phe Ile Ser Gly Lys Asp Ile Ser
            20                  25

<210> SEQ ID NO 38
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(8)
<223> OTHER INFORMATION: n is a, c, g, t or u
<220> FEATURE:
<221> NAME/KEY: misc_feature
<222> LOCATION: (9)..(9)
<223> OTHER INFORMATION: k is g or t
<220> FEATURE:
<221> NAME/KEY: misc_feature
<222> LOCATION: (10)..(11)
<223> OTHER INFORMATION: n is a, c, g, t or u
<220> FEATURE:
<221> NAME/KEY: misc_feature
<222> LOCATION: (12)..(12)
<223> OTHER INFORMATION: k is g or t
<220> FEATURE:
<221> NAME/KEY: misc_feature
<222> LOCATION: (13)..(14)
<223> OTHER INFORMATION: n is a, c, g, t or u
<220> FEATURE:
<221> NAME/KEY: misc_feature
<222> LOCATION: (15)..(15)
<223> OTHER INFORMATION: k is g or t
<220> FEATURE:
<221> NAME/KEY: misc_feature
<222> LOCATION: (16)..(17)
<223> OTHER INFORMATION: n is a, c, g, t or u
<220> FEATURE:
<221> NAME/KEY: misc_feature
<222> LOCATION: (18)..(18)
<223> OTHER INFORMATION: k is g or t
<220> FEATURE:
<221> NAME/KEY: misc_feature
<222> LOCATION: (19)..(20)
<223> OTHER INFORMATION: n is a, c, g, t or u
<220> FEATURE:
<221> NAME/KEY: misc_feature
<222> LOCATION: (21)..(21)
<223> OTHER INFORMATION: k is g or t
<220> FEATURE:
<221> NAME/KEY: misc_feature
<222> LOCATION: (22)..(23)
<223> OTHER INFORMATION: n is a, c, g, t or u
<220> FEATURE:
<221> NAME/KEY: misc_feature
<222> LOCATION: (24)..(24)
<223> OTHER INFORMATION: k is g or t
<220> FEATURE:
<221> NAME/KEY: misc_feature
<222> LOCATION: (25)..(26)
<223> OTHER INFORMATION: n is a, c, g, t or u
<220> FEATURE:
<221> NAME/KEY: misc_feature
<222> LOCATION: (27)..(27)
```

<223> OTHER INFORMATION: k is g or t

<400> SEQUENCE: 38
gcttgtnnkn nknnknnknn knnknnktgc ggtggaggt                                39

<210> SEQ ID NO 39
<211> LENGTH: 39
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (7)..(8)
<223> OTHER INFORMATION: n is a, c, g, t or u
<220> FEATURE:
<221> NAME/KEY: misc_feature
<222> LOCATION: (9)..(9)
<223> OTHER INFORMATION: m is a or c
<220> FEATURE:
<221> NAME/KEY: misc_feature
<222> LOCATION: (10)..(11)
<223> OTHER INFORMATION: n is a, c, g, t or u
<220> FEATURE:
<221> NAME/KEY: misc_feature
<222> LOCATION: (12)..(12)
<223> OTHER INFORMATION: m is a or c
<220> FEATURE:
<221> NAME/KEY: misc_feature
<222> LOCATION: (13)..(14)
<223> OTHER INFORMATION: n is a, c, g, t or u
<220> FEATURE:
<221> NAME/KEY: misc_feature
<222> LOCATION: (15)..(15)
<223> OTHER INFORMATION: m is a or c
<220> FEATURE:
<221> NAME/KEY: misc_feature
<222> LOCATION: (16)..(17)
<223> OTHER INFORMATION: n is a, c, g, t or u
<220> FEATURE:
<221> NAME/KEY: misc_feature
<222> LOCATION: (18)..(18)
<223> OTHER INFORMATION: m is a or c
<220> FEATURE:
<221> NAME/KEY: misc_feature
<222> LOCATION: (19)..(20)
<223> OTHER INFORMATION: n is a, c, g, t or u
<220> FEATURE:
<221> NAME/KEY: misc_feature
<222> LOCATION: (21)..(21)
<223> OTHER INFORMATION: m is a or c
<220> FEATURE:
<221> NAME/KEY: misc_feature
<222> LOCATION: (22)..(23)
<223> OTHER INFORMATION: n is a, c, g, t or u
<220> FEATURE:
<221> NAME/KEY: misc_feature
<222> LOCATION: (24)..(24)
<223> OTHER INFORMATION: m is a or c
<220> FEATURE:
<221> NAME/KEY: misc_feature
<222> LOCATION: (25)..(26)
<223> OTHER INFORMATION: n is a, c, g, t or u
<220> FEATURE:
<221> NAME/KEY: misc_feature
<222> LOCATION: (27)..(27)
<223> OTHER INFORMATION: m is a or c

<400> SEQUENCE: 39
cgaacannmn nmnnmnnmn mnnmnnmacg ccacctcca                                 39

<210> SEQ ID NO 40
<211> LENGTH: 13
<212> TYPE: PRT
<213> ORGANISM: Artificial Sequence

```
<220> FEATURE:
<223> OTHER INFORMATION: Synthetic polypeptide
<220> FEATURE:
<221> NAME/KEY: misc_feature
<222> LOCATION: (3)..(9)
<223> OTHER INFORMATION: Xaa can be any naturally occurring amino acid

<400> SEQUENCE: 40

Ala Cys Xaa Xaa Xaa Xaa Xaa Xaa Xaa Cys Gly Gly Gly
1               5                   10

<210> SEQ ID NO 41
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 41
gcaatgcgat tgatactccc                                                20

<210> SEQ ID NO 42
<211> LENGTH: 7
<212> TYPE: PRT
<213> ORGANISM: Artificial Sequence
<220> FEATURE:
<223> OTHER INFORMATION: Synthetic polypeptide

<400> SEQUENCE: 42

Ile Leu Asp Leu Pro Lys Phe
1               5

<210> SEQ ID NO 43
<211> LENGTH: 59
<212> TYPE: DNA
<213> ORGANISM: Artificial Sequence
<220> FEATURE:
<223> OTHER INFORMATION: Synthetic polynucleotide

<400> SEQUENCE: 43
tcacgaattc ggcttgtatt cttgatttgc cgaagttttg cggtggaggt tcggctagc    59

<210> SEQ ID NO 44
<211> LENGTH: 49
<212> TYPE: DNA
<213> ORGANISM: Artificial Sequence
<220> FEATURE:
<223> OTHER INFORMATION: Synthetic polynucleotide

<400> SEQUENCE: 44
gctcgctagc cgaacctcca ccgcaaaact tcggcaaatc aagaataca               49
```

ARTICLES AND METHODS DIRECTED TO PERSONALIZED THERAPY OF CANCER

RELATED APPLICATIONS

This application is a continuation of U.S. application Ser. No. 16/983,491, filed Aug. 3, 2020, which is a continuation of U.S. application Ser. No. 16/753,635, filed Apr. 3, 2020, which is a national stage filing under 35 U.S.C. § 371 of international PCT application, PCT/RU2018/000653, filed Oct. 4, 2018, which claims priority to Russian Application No. 2017134483, filed Oct. 4, 2017, Russian Application No. 2018112009, filed Apr. 4, 2018, and Russian Application No. 2018134321, filed Oct. 1, 2018, the entire contents of each of which is hereby incorporated herein by reference.

BACKGROUND OF INVENTION

Lymphoma is a cancer in the lymphatic cells of the immune system. Typically, lymphomas present as a solid tumor of lymphoid cells. These malignant cells often originate in lymph nodes, presenting as an enlargement of the node, i.e., a tumor. It can also affect other organs in which case it is referred to as extranodal lymphoma. Extranodal sites include the skin, brain, bowels and bone. Lymphomas are closely related to lymphoid leukemias, which also originate in lymphocytes but typically involve only circulating blood and the bone marrow and do not usually form static tumors (Parham, P. The immune system. New York: Garland Science. p. 414, 2005). Treatment involves chemotherapy and in some cases radiotherapy and/or bone marrow transplantation, and can be curable depending on the histology, type, and stage of the disease. More advanced cases of lymphoma are resistant and, accordingly, novel treatment approaches are needed.

SUMMARY OF INVENTION

The disclosure provides methods for treatment of B cell malignancies using personalized medicine. More particularly, the methods provide for isolating a B cell receptor from a B cell malignancy in a subject, identifying a ligand for the B cell receptor, and then treating the subject with the B cell receptor ligand coupled to a therapeutic agent, e.g., a CART cell in which the B cell receptor ligand comprises the antigen binding domain.

In some embodiments, the methods of the disclosure use an autocrine-based format to identify B cell receptor ligands specific to a tumor. Once a B cell receptor ligand is identified, a patient can be treated with the ligand attached to a therapeutic agent. The whole process, from diagnosis to treatment can be completed in a short period of time, e.g., within several weeks. As an example, B cell receptor ligands may be identified by co-expressing a B cell receptor from a tumor and a chimeric antigen receptor (CAR) in a T cell, where the extracellular domain of the CAR comprises a peptide from a library. Activation of the T cell by the CAR indicates that the extracellular domain of the CAR has bound the B cell receptor and the peptide from the peptide library is a B cell receptor ligand. Alternatively, contemplated herein is the use of phage display for identification of the B cell receptor ligand.

The disclosure also provides methods for treatment of cancer by administering CAR-expressing T-cells, wherein the CAR comprises an antigen binding domain that specifically binds a cancer-specific antigen in a cancer-specific manner, e.g., a CAR with an antigen binding domain comprising a B cell receptor ligand as is described herein; and a vaccine comprising a polypeptide or a nucleic acid expressing the same cancer-specific antigen, or a cancer-specific fragment thereof, e.g., a B cell receptor or fragment thereof. It has surprisingly been discovered that when a CAR specific for a cancer antigen and that same antigen are administered to a subject, the two have a synergistic effect on a reduction in tumor volume.

In one aspect, provided herein are methods of treating lymphoma in a subject. The methods comprise:
  identifying a unique B cell receptor expressed in lymphoma cells of the subject;
  expressing the unique B cell receptor in a cell;
  contacting the cell with a putative unique B cell receptor ligand from a library;
  detecting binding of said unique B cell receptor to a putative unique B cell receptor ligand, thereby identifying a unique B cell receptor ligand; and
  administering to the subject a therapeutically effective amount of the B cell receptor ligand coupled to a therapeutic agent.

In some embodiments, the putative unique B cell receptor ligand comprises a peptide, a cyclopeptide, a peptoid, a cyclopeptoid, a polysaccharide, a lipid, or a small molecule. In some embodiments, the unique B cell receptor and the putative unique B cell receptor ligand are co-expressed in T cells. In some embodiments, the cell comprises a CAR comprising the putative unique B cell receptor ligand.

In some embodiments, the unique B cell receptor is contacted with a putative unique B cell receptor ligand from a library by phage display. In some embodiments, the library comprises a library of putative B cell receptor ligands linked to a phage. In some embodiments, the unique B cell receptor is attached to a solid support. In some embodiments, contacting unique B cell receptor with a putative unique B cell receptor ligand from a library comprises panning the unique B cell receptor attached to a solid support with the library of putative B cell receptor ligands linked to a phage for one or more rounds. In some embodiments, each round of the panning includes negative selection.

In some embodiments, said detection method comprises identifying activation of the T cell.

In another aspect, provided herein are methods of treating lymphoma in a subject. The methods comprise:
  identifying a unique B cell receptor expressed in lymphoma cells of the subject;
  co-expressing the unique B cell receptor and putative unique B cell receptor ligand from a library in a cell;
  detecting binding of said unique B cell receptor to a putative unique B cell receptor ligand, thereby identifying a unique B cell receptor ligand; and
  administering to the subject a therapeutically effective amount of the B cell receptor ligand coupled to a therapeutic agent.

In some embodiments, the unique B cell receptor and the putative unique B cell receptor ligand are co-expressed in T cells.

In some embodiments, the T cell comprises a CAR comprising the putative unique B cell receptor ligand.

In some embodiments, said detection method comprises identifying activation of the T cell.

In some embodiment, the subject is administered the B cell receptor, or a fragment thereof, concomitantly with the therapeutic agent.

In another aspect, provided herein are methods of identifying a B cell receptor ligand. The methods comprise:

providing to a population of T cells nucleic acid molecules encoding a B cell receptor and a library of chimeric antigen receptors (CARs), wherein each CAR within the library comprises a distinct putative B cell receptor ligand domain;

coexpressing the B cell receptor and the library of CARs in T cells;

measuring activation of the T cells, wherein the putative B cell receptor ligand domain of a CAR from the library of CARs comprises a ligand of the B cell receptor if a T cell expressing the B cell receptor and the CAR is activated; and isolating the nucleic acid molecule encoding the CAR from an activated T cell; and sequencing the putative B cell receptor ligand domain of the nucleic acid molecule encoding the CAR from the activated T cell;

thereby identifying a B cell receptor ligand.

In some embodiments, the B cell receptor is from a cancer cell. In some embodiments, the cancer cell is a lymphoma cell. In some embodiments, the lymphoma cell is obtained from a tumor from a patient In some embodiments, the methods further comprise treating a subject having lymphoma with the B cell receptor ligand wherein the B cell receptor is expressed in a tumor from the subject; and the B cell receptor ligand coupled to a therapeutic agent.

In some embodiment, the subject is administered the B cell receptor, or a fragment thereof, concomitantly with the therapeutic agent.

In another aspect, provided herein are methods of treating lymphoma. The methods comprise:
administering to a subject a therapeutically effective dose of a B cell receptor ligand coupled to a therapeutic agent,
wherein the B cell receptor ligand comprises a putative B cell receptor ligand domain, and wherein a CAR comprising the putative B cell receptor ligand domain activates a T cell when co-expressed with the B cell receptor of the lymphoma cells.

In another aspect, provided herein are methods of treating lymphoma in a subject. The methods comprise:
identifying a unique B cell receptor expressed in lymphoma cells of the subject;
co-expressing the unique B cell receptor and a chimeric antigen receptor (CAR) from a library of CARs in a T cell, wherein each CAR within the library comprises a distinct putative B cell receptor ligand domain;
identifying a B cell receptor ligand by identifying an activated T cell, wherein the putative B cell receptor ligand domain of the CAR from the library of CARs comprises a ligand of the unique B cell receptor if the T cell expressing the B cell receptor and the CAR is activated; and
administering to the subject a therapeutically effective dose of the B cell receptor ligand coupled to a therapeutic agent.

In some embodiments, the methods further comprise preparing the B cell receptor ligand coupled to a therapeutic agent.

In some embodiments, the T cell is activated by autocrine-based activation of the CAR.

In some embodiments, identifying a B cell receptor ligand further comprises isolating the nucleic acid molecule encoding the CAR from the activated T cell; and sequencing the putative B cell receptor ligand domain of the nucleic acid molecule encoding the CAR from the activated T cell.

In some embodiment, the subject is administered the B cell receptor, or a fragment thereof, concomitantly with the therapeutic agent.

In another aspect, provided herein are methods of treating lymphoma in a subject comprising:
identifying a unique B cell receptor expressed in lymphoma cells of the subject;
co-expressing the unique B cell receptor and a putative unique B cell receptor ligand from a library in a cell;
identifying said unique B cell receptor ligand by a detection method, wherein a putative unique B cell receptor ligand is a unique B cell receptor ligand if it interacts with the unique B cell receptor; and
administering to the subject a therapeutically effective amount of the B cell receptor ligand coupled to a therapeutic agent.

In some embodiments, the unique B cell receptor and a putative unique B cell receptor ligand are co-expressed in T cells.

In some embodiments, the cell comprises a CAR comprising the putative unique B cell receptor ligand.

In some embodiments, said detection method comprises identifying activation of the T cell.

In some embodiment, the subject is administered the B cell receptor, or a fragment thereof, concomitantly with the therapeutic agent.

In another aspect, provided herein are methods for treating lymphoma in a subject comprising: administering to the subject a therapeutically effective amount of a CART cell expressing a first CAR, wherein:
(i) the first CAR comprises an antigen binding domain that comprises a polypeptide from a cyclopeptide library that binds a unique B cell receptor expressed in lymphoma cells of the subject,
(ii) the antigen binding domain is identified by
    (a) identifying the unique B cell receptor expressed in lymphoma cells of the subject;
    (b) co-expressing the unique B cell receptor and a second CAR from a library of CARs in a T cell, wherein each CAR within the library comprises a distinct putative ligand domain that comprises a polypeptide from a cyclopeptide library; and
    (c) identifying the antigen binding domain of the first CAR by identifying an activated T cell, wherein the putative B cell receptor ligand domain of the second CAR from the library of CARs comprises the antigen binding domain of the first CAR if the T cell expressing the B cell receptor and the second CAR is activated; and
(iii) the first CAR has greater specificity and/or activity than a control.

In some embodiments, the control comprises a CART cell. In some embodiments, the antigen binding domain of the CAR expressed by the CART cell binds a ligand other than a B-cell receptor. In some embodiments, the antigen binding domain binds CD-19.

In some embodiments, the first CAR and the second CAR are the same CAR. In some embodiments, the first CAR and the second CAR are different CARs.

In some embodiments, activity comprises cytotoxicity towards cells expressing the unique B cell receptor relative to a control. In some embodiments, cytotoxicity of the CART towards cells expressing the unique B cell receptor is 0%-10% greater than the control, as measured by % lysis, at an effector:target ratio of 1:1-10:1. In some embodiments, cytotoxicity of the CART towards cells expressing the unique B cell receptor is at least 10% greater than the control, as measured by % lysis, at an effector:target ratio of 10:1 or greater.

In some embodiments, the control comprises a CAR comprising an antigen binding domain that binds a ligand other than the B-cell receptor expressed on the cells expressing the unique B cell receptor.

In some embodiments, specificity comprises cytotoxicity towards cells that do not express the unique B cell receptor. In some embodiments, cytotoxicity of the CART towards cells that do not express the unique B cell receptor is less than 10%, as measured by % lysis. In some embodiments, cytotoxicity of the CART towards cells that do not express the unique B cell receptor is 0-10% less than the cytotoxicity of a control that binds a ligand expressed on the cells at an effector:target ratio of less than 10:1. In some embodiments, cytotoxicity of the CART towards cells that do not express the unique B cell receptor is at least 15% less than the cytotoxicity of a control that binds a ligand expressed on the cells at an effector:target ratio of 10:1 or greater.

In some embodiment, the subject is administered the B cell receptor, or a fragment thereof, concomitantly with the therapeutic agent.

In another aspect, provided herein are methods for treating lymphoma in subject population comprising:
 selecting subjects having lymphoma; and
 administering to each subject a therapeutically effective amount of a CART cell expressing a first CAR unique to the B cell receptor expressed on the lymphoma cells on each subject, wherein:
 (i) the first CAR comprises an antigen binding domain that comprises a polypeptide from a cyclopeptide library that binds a unique B cell receptor expressed in lymphoma cells of each subject,
 (ii) the antigen binding domain is identified by
  (a) identifying the unique B cell receptor expressed in lymphoma cells of the subject;
  (b) co-expressing the unique B cell receptor and a second CAR from a library of CARs in a T cell, wherein each CAR within the library comprises a distinct putative ligand domain that comprises a polypeptide from a cyclopeptide library; and
  (c) identifying the antigen binding domain of the first CAR by identifying an activated T cell, wherein the putative B cell receptor ligand domain of the second CAR from the library of CARs comprises the antigen binding domain of the first CAR if the T cell expressing the B cell receptor and the second CAR is activated; and
 (iii) the first CAR has greater specificity and/or activity than a control.

In some embodiments, the control comprises a CART cell. In some embodiments, the antigen binding domain of the CAR expressed by the CART cell binds a ligand other than a B-cell receptor. In some embodiments, the antigen binding domain binds CD-19.

In some embodiments, the first CAR and the second CAR are the same CAR. In some embodiments, the first CAR and the second CAR are different CARs.

In some embodiments, activity comprises cytotoxicity towards cells expressing the unique B cell receptor relative to a control. In some embodiments, cytotoxicity of the CART towards cells expressing the unique B cell receptor is 0%-10% greater than the control, as measured by % lysis, at an effector:target ratio of 1:1-10:1. In some embodiments, cytotoxicity of the CART towards cells expressing the unique B cell receptor is at least 10% greater than the control, as measured by % lysis, at an effector:target ratio of 10:1 or greater.

In some embodiments, the control comprises a CAR comprising an antigen binding domain that binds a ligand other than the B-cell receptor expressed on the cells expressing the unique B cell receptor.

In some embodiments, specificity comprises cytotoxicity towards cells that do not express the unique B cell receptor. In some embodiments, cytotoxicity of the CART towards cells that do not express the unique B cell receptor is less than 10%, as measured by % lysis. In some embodiments, cytotoxicity of the CART towards cells that do not express the unique B cell receptor is 0-10% less than the cytotoxicity of a control that binds a ligand expressed on the cells at an effector:target ratio of less than 10:1. In some embodiments, cytotoxicity of the CART towards cells that do not express the unique B cell receptor is at least 15% less than the cytotoxicity of a control that binds a ligand expressed on the cells at an effector:target ratio of 10:1 or greater.

In another aspect, provided herein are methods of rapidly identifying a personalized antibody binding ligand specific for a B cell lymphoma, e.g., a B cell receptor ligand, comprising:
 identifying a B cell receptor from a B cell lymphoma cell,
 providing to a population of T cells nucleic acid molecules encoding the B cell receptor and a library of chimeric antigen receptors (CARs), wherein each CAR within the library comprises a distinct putative B cell receptor ligand domain;
 coexpressing the B cell receptor and the library of CARs in T cells;
 measuring activation of the T cells, wherein the putative B cell receptor ligand domain of a CAR from the library of CARs comprises a ligand of the B cell receptor if a T cell expressing the B cell receptor and the CAR is activated; and
 isolating the nucleic acid molecule encoding the CAR from an activated T cell; and
 sequencing the putative B cell receptor ligand domain of the nucleic acid molecule encoding the CAR from the activated T cell;
 thereby identifying a B cell receptor ligand.

In some embodiments, the B cell receptor ligand is identified within 4 weeks, within 3 weeks, within 2 weeks, or within 1 week. In some embodiments, the B cell receptor ligand is identified within 3 weeks.

In some embodiments, the B cell lymphoma cell is obtained from a tumor from a patient.

In some embodiments, the putative B cell receptor ligand domain comprises a polypeptide of 30 amino acids or less. In some embodiments, the putative B cell receptor ligand domain comprises a polypeptide from a cyclopeptide library. In some embodiments, the putative B cell receptor ligand domain further comprises an Fc region.

In some embodiments, T cell activation is measured by an increase in expression of CD69 or CD25. In some embodiments, T cell activation is measured by an increase in expression of a fluorescent protein reporter gene under the control of Jun, NF—KB and/or Rel.

In some embodiments, the methods further comprise treating a subject having lymphoma with the B cell receptor ligand, wherein the B cell receptor ligand coupled to a therapeutic agent.

In another aspect, provided herein is a chimeric antigen receptor (CAR) comprising:

a putative B cell receptor ligand domain that comprises a polypeptide from a cyclopeptide library;
a transmembrane domain; and
an intracellular region.

In some embodiments, the CAR activates a T cell when co-expressed with a B cell receptor, wherein a B cell receptor ligand of the B cell receptor comprises the putative B cell receptor ligand domain. In some embodiments, the B cell receptor ligand comprises the amino acid sequence of any of SEQ ID NOs: 1-3.

In another aspect, provided herein is a method of treating lymphoma in a subject comprising:
identifying a unique B cell receptor expressed in lymphoma cells of the subject;
contacting the unique B cell receptor with a phage display library, wherein the phage display library comprises a library of putative unique B cell receptor ligands linked to phages;
detecting binding of said unique B cell receptor to a putative unique B cell receptor ligand, thereby identifying a unique B cell receptor ligand; and
administering to the subject a therapeutically effective amount of the B cell receptor ligand coupled to a therapeutic agent.

In some embodiments, the putative unique B cell receptor ligand comprises a peptide, a cyclopeptide, a peptoid, a cyclopeptoid, a polysaccharide, a lipid, or a small molecule.

In some embodiments, the unique B cell receptor is attached to a solid support.

In some embodiments, contacting unique B cell receptor with a putative unique B cell receptor ligand from a library comprises panning the unique B cell receptor attached to a solid support with the library of putative B cell receptor ligands linked to a phage for one or more rounds. In some embodiments, each round of the panning includes negative selection.

In some embodiments, the subject is determined to have lymphoma.

In some embodiments, the subject is determined to have one or more single-nucleotide polymorphisms (SNPs) associated with lymphoma.

In some embodiments, identifying a unique B cell receptor comprises:
obtaining cells from a biopsy;
extracting RNA from the cells;
synthesizing cDNA from the extracted RNA; and
sequencing the cDNA. In some embodiments, identifying a unique B cell receptor comprises cloning and sequencing circulating cell free DNA.

In some embodiments, the method is performed in 3 weeks or less.

In some embodiments, the therapeutic agent comprises a radioactive isotope.

In some embodiments, the B cell receptor ligand coupled to a therapeutic agent comprises a therapeutic CAR. In some embodiments, the therapeutic agent comprises a chemotherapy. In some embodiments, the therapeutic agent comprises an immunotherapy.

In another aspect, provided herein is a method of treating cancer in a subject. In some embodiments, the method comprises concomitantly administering: CAR-expressing T-cells, wherein the CAR comprises an antigen binding domain that specifically binds a cancer-specific antigen in a cancer-specific manner; and a vaccine comprising a polypeptide or a nucleic acid expressing the cancer-specific antigen, or a cancer-specific fragment thereof.

In some embodiments, the cancer-specific antigen is a B-cell receptor. In some embodiments, the cancer is a lymphoma. In some embodiments, the polypeptide or nucleic acid comprises a heavy or light chain variable region, or fragment thereof.

In some embodiments, the cancer-specific antigen is expressed in the cancer and comprises a somatic mutation. In some embodiments, the non-cancerous cells of the subject do not have the somatic mutation. In some embodiments, the mutation is a point mutation, a splice-site mutation, a frameshift mutation, a read-through mutation, or a gene-fusion mutation. In some embodiments, the somatic mutation comprises a mutation in EGFRvIII, PSCA, BCMA, CD30, CEA, CD22, L1CAM, ROR1, ErbB, CD123, IL13Rα2, Mesothelin, FRα, VEGFR, c-Met, 5T4, CD44v6, B7-H4, CD133, CD138, CD33, CD28, GPC3, EphA2, CD19, ACVR2B, anaplastic lymphoma kinase (ALK), MYCN, BCR, HER2, NY-ESO1, MUC1, or MUC16. In some embodiments, the cancer comprises a tumor. In some embodiments, the polypeptide or nucleic acid comprises the somatic mutation.

In some embodiments, the concomitant administration occurs at least two times, at least three times, at least four times, at least five times, at least six times, at least seven times, at least eight times, at least nine times, or at least ten times in the subject. In some embodiments, the CAR-expressing T-cells are administered before the vaccine. In some embodiments, the CAR-expressing T-cells are administered after the vaccine.

In some embodiments, the method further comprises identifying the cancer-specific antigen in the subject. In some embodiments, identifying the cancer-specific antigen comprises: (i) obtaining cancerous cells from a subject; (ii) extracting DNA from the cells; and (iii) sequencing the DNA. In some embodiments, identifying the cancer-specific antigen further comprises comparing the DNA sequence obtained from the cancerous cells to a DNA sequence of the same gene obtained from non-cancerous cells. In some embodiments, the DNA is isolated from tumor cells. In some embodiments, the cancer-specific antigen comprises isolating and sequencing circulating cell free DNA of the subject. In some embodiments, identifying the cancer-specific antigen comprises: (i) obtaining cancerous cells from a subject; (ii) extracting RNA from the cells; (iii) synthesizing cDNA from the extracted RNA; and (iv) sequencing the cDNA. In some embodiments, identifying the cancer-specific antigen further comprises comparing the cDNA sequence obtained from the cancerous cells to a cDNA sequence of the same gene obtained from non-cancerous cells.

In some embodiments, the vaccine comprises two or more polypeptides having overlapping sequences, each expressing a fragment of the cancer-specific antigen.

In some embodiments, the method further comprises providing CAR-expressing T-cells by: (i) identifying an antigen binding domain that specifically binds the cancer-specific antigen in a cancer-specific manner; and (ii) expressing a CAR comprising the antigen binding domain in T-cells.

In some embodiments, the polypeptide is conjugated to KLH.

In some embodiments the vaccine is administered by intravenous, intraperitoneal, transmucosal, oral, subcutaneous, pulmonary, intranasal, intradermal or intramuscular administration. In some embodiments the vaccine is administered intratumorally.

In some embodiments the CAR-expressing T-cells are administered by intravenous administration.

In some embodiments, the method further comprises administering a TLR9 agonist. In some embodiments, the cancer-specific antigen is OX40.

In another aspect, provided herein is a composition for treating cancer in a subject comprising: CAR-expressing T-cells, wherein the CAR comprises an antigen binding domain that specifically binds a cancer-specific antigen in a cancer-specific manner; and a polypeptide or a nucleic acid expressing the cancer-specific antigen, or a cancer-specific fragment thereof.

In some embodiments, the cancer-specific antigen is a B-cell receptor. In some embodiments, the polypeptide or nucleic acid comprises a heavy or light chain variable region, or fragment thereof.

In some embodiments, the cancer-specific antigen is expressed in the cancer and comprises a somatic mutation.

In some embodiments, the non-cancerous cells of the subject do not have the somatic mutation. In some embodiments, the mutation is a point mutation, a splice-site mutation, a frameshift mutation, a read-through mutation, or a gene-fusion mutation. In some embodiments, the somatic mutation comprises a mutation in EGFRvIII, PSCA, BCMA, CD30, CEA, CD22, L1CAM, ROR1, ErbB, CD123, IL13Rα2, Mesothelin, FRα, VEGFR, c-Met, 5T4, CD44v6, B7-H4, CD133, CD138, CD33, CD28, GPC3, EphA2, CD19, ACVR2B, anaplastic lymphoma kinase (ALK), MYCN, BCR, HER2, NY-ESO1, MUC1, or MUC16. In some embodiments, the polypeptide or nucleic acid comprises the somatic mutation.

In some embodiments, the vaccine comprises two or more polypeptides having overlapping sequences, each expressing a fragment of the cancer-specific antigen.

In some embodiments, the polypeptide is conjugated to KLH.

In some embodiments, the method further comprises administering a TLR9 agonist. In some embodiments, the cancer-specific antigen is OX40.

In some embodiments, the CAR, e.g., a CAR described herein, comprises a transmembrane domain. In some embodiments, the transmembrane domain comprises alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137 and/or CD154.

In some embodiments, the CAR, e.g., a CAR described herein, comprises an intracellular region. In some embodiments, the intracellular region comprises a MHC class I molecule, a TNF receptor protein, an Immunoglobulin-like protein, a cytokine receptor, an integrin, a signaling lymphocytic activation molecule (SLAM protein), an activating NK cell receptor, BTLA, a Toll ligand receptor, OX40, CD2, CD7, CD27, CD28, CD30, CD40, CDS, ICAM-1, LFA-1 (CD25/CD18), 4-29B (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD423, ITGA4, IA4, CD49D, ITGA6, VLA-6, CD49f, ITGAD, CD11d, ITGAE, CD103, ITGAL, CD11a, LFA-1, ITGAM, CD129, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 304), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD123, and/or a ligand that specifically binds with CD83.

In some embodiments, the CAR, e.g., a CAR described herein, comprises a hinge domain.

In some embodiments, the therapeutic agent comprises a radioactive isotope. In some embodiments, the B cell receptor ligand coupled to a therapeutic agent comprises a therapeutic CAR. In some embodiments, the therapeutic agent comprises a chemotherapy. In some embodiments, the therapeutic agent comprises an immunotherapy.

In some embodiments, identifying a unique B cell receptor comprises: obtaining cells from a biopsy; extracting RNA from the cells; synthesizing cDNA from the extracted RNA; and sequencing the cDNA. In some embodiments, identifying a unique B cell receptor comprises cloning and sequencing circulating cell free DNA.

In some embodiments, the putative B cell receptor ligand domain comprises a polypeptide of 30 amino acids or less. In some embodiments, the putative B cell receptor ligand domain comprises a polypeptide from a cyclopeptide library. In some embodiments, the putative B cell receptor ligand domain further comprises an Fc region.

In some embodiments, T cell activation is measured by an increase in expression of CD69 or CD25. In some embodiments, T cell activation is measured by an increase in expression of a fluorescent protein reporter gene under the control of Jun, NF-κB and/or Rel.

In some embodiments, the method is performed in 3 weeks or less.

In some embodiments, the subject is determined to have lymphoma. In some embodiments, the subject is determined to have one or more single-nucleotide polymorphisms (SNPs) associated with lymphoma.

BRIEF DESCRIPTION OF DRAWINGS

The following drawings form part of the present specification and are included to further demonstrate certain aspects of the present disclosure, which can be better understood by reference to one or more of these drawings in combination with the detailed description of specific embodiments presented herein. In the figures:

FIG. 2A shows the reporter system format. FIG. 2B is flow cytometry data showing verification of the reporter cell assay by Myc-CAR/anti-Myc antibody pair interaction. FIG. 2C shows that patient BCR-specific peptides on CAR activate reporter Jurkat cells transduced by membrane tethered follicular lymphoma BCRs.

FIG. 3A is a series of histograms showing SPR analysis of the interaction of the selected cyclopeptides CILDLPKFC (FL1) (SEQ ID NO: 1), CMPHWQNHC (FL2) (SEQ ID NO: 2), and CTTDQARKC (FL3) (SEQ ID NO: 3) and the malignant BCR. Surface staining of Raji cells transduced with lymphoma BCR scFv by synthetic biotinylated peptides and antibody against IgG Fc. For IgG Fc staining, same Raji cell population flow cytometry result was used as control in the three histograms. FIG. 3B is a series of graphs showing % cell lysis. FL-CARTs were co-cultured with Raji cells transduced with different lymphoma BCRs. Mock transduced T cells and CD19-CART was used as a comparison. Cytotoxicity was determined by measuring lactate dehydrogenase release after 6 hours. FIG. 3C shows cells from the patient's biopsy or control B-cells were stained with the synthetic biotinylated FL1 peptide. The B-cell population was identified by B220 specific antibody and the FL1 peptide was labeled with biotin and detected with FITC labeled streptavidin. FIG. 3D is a graph showing lysis of B cells derived from the lymphoma biopsy sample by FL1-CART compared to Myc-CART and Mock transduced T cells.

FIG. 4A is a schematic diagram showing experimental design indicating the engraftment of NOD SCID mice with 5×10$^6$ Raji-FL1 cells. At day 15, animals (12 per group) were randomized according to the tumor volume and received i.v. 3×10$^6$ FL1-CART, CD19-CAR or Myc-CART per mouse at day 17. FIG. 4B is a series of graphs showing transduction efficacy of activated, CD3/CD28 bead-expanded human CD8$^+$ T-cells with lentiviral based vectors expressing FL1-CAR, Myc-CAR and CD19-CAR constructs. Cells were stained with IgG1 specific antibody or protein L. FIG. 4C is a graph showing survival of Raji-FL xenografted mice treated on day 17 after tumor injection with 3×10$^6$ CTLs (n=12 mice per group). Overall survival curves were plotted using the Kaplan-Meier method and compared using the log-rank (Mantel-Cox) test ($*p<0.01$). FIG. 4D is a graph showing a tumor growth curve in groups of mice (n=12) treated by 3×10$^6$ of FL1-CART, CD19-CART or Myc-CART administered i.v. on day 17 after injection of Raji-FL1. Absolute counts of adoptively transferred modified T cells were monitored in blood obtained from retro-orbital puncture using flow cytometry analysis with a CD3$^+$ specific antibody (insert). FIG. 4E shows flow cytometry analysis of the phenotype of FL1-CART cells prior to injection and on day 21 following the injection. FIG. 4F is a graph showing relative percentages of naïve, central memory and effector memory CART on day 21 following the injection.

FIGS. 5A-5C illustrate the structure of the reconstituted malignant BCR and combinatorial cyclopeptide library. FIG. 5A shows amino acid sequences of the combinatorial cyclopeptide library fused with chimeric antigen receptors signaling domains. The sequence corresponds to SEQ ID NO: 33. FIG. 5B shows reconstituted malignant BCR fused with the IgG1 Fc hinge and membrane-spanning PDGFR domain. The sequence corresponds to SEQ ID NO: 34. FIG. 5C shows a schematic representation of secreted molecules.

FIG. 7A shows bioluminescent imaging of organ-specific metastasis of Raji-FL1 cells (green, indicated by arrows) on day 35 after tumor implantation in mice treated by CD19-CART, FL1-CART and Myc-CART. For the Raji-FL1 cells detection mice received i.p. injection of the D-luciferine. FIG. 7B shows histopathological changes analysis in tumors from CD19-CART, FL1-CART or Myc-CART treated animals. For identification of the histopathological changes tumors were stained with Hematoxylin-Eosin. Lymphoma B cells with basophilic cytoplasm and high mitotic rate are indicated as black arrows, right panel. Macrophages containing cellular debris giving the characteristic "starry sky" appearance are indicated by red arrows, right panel. Cells thought to be in the state of apoptosis are indicated by arrows, left panel. FIG. 7C shows immunohistochemical analysis of CD19-CART, FL1-CART or Myc-CART infiltration into the tumor (black arrows). The human CD8-specific antibodies were used for CART staining.

FIGS. 8A-8E show that malignant B cell receptor recognizes self-antigen myoferlin. FIG. 8A shows a schematic representation of myoferlin-driven autoreactive lymphomagenesis. FIG. 8B shows PCR analysis of bcl-2 rearrangement in FL patient 1 biopsy sample. Staining of HEp-2 cells (FIG. 8C) and myoferlin-expressing HEK293T cells (FIG. 8D) with soluble malignant BCR is shown. Shown in FIG. 8E is an alignment of the amino acid sequences of the identified malignant-specific peptide FL1 with the protein Myoferlin and surface proteins from *Streptococcus mitis* and *Pneumocytis jirovecii*. The sequences from top to bottom correspond to SEQ ID NOs: 1, 35, 36, and 37.

DETAILED DESCRIPTION OF INVENTION

Figure 1:
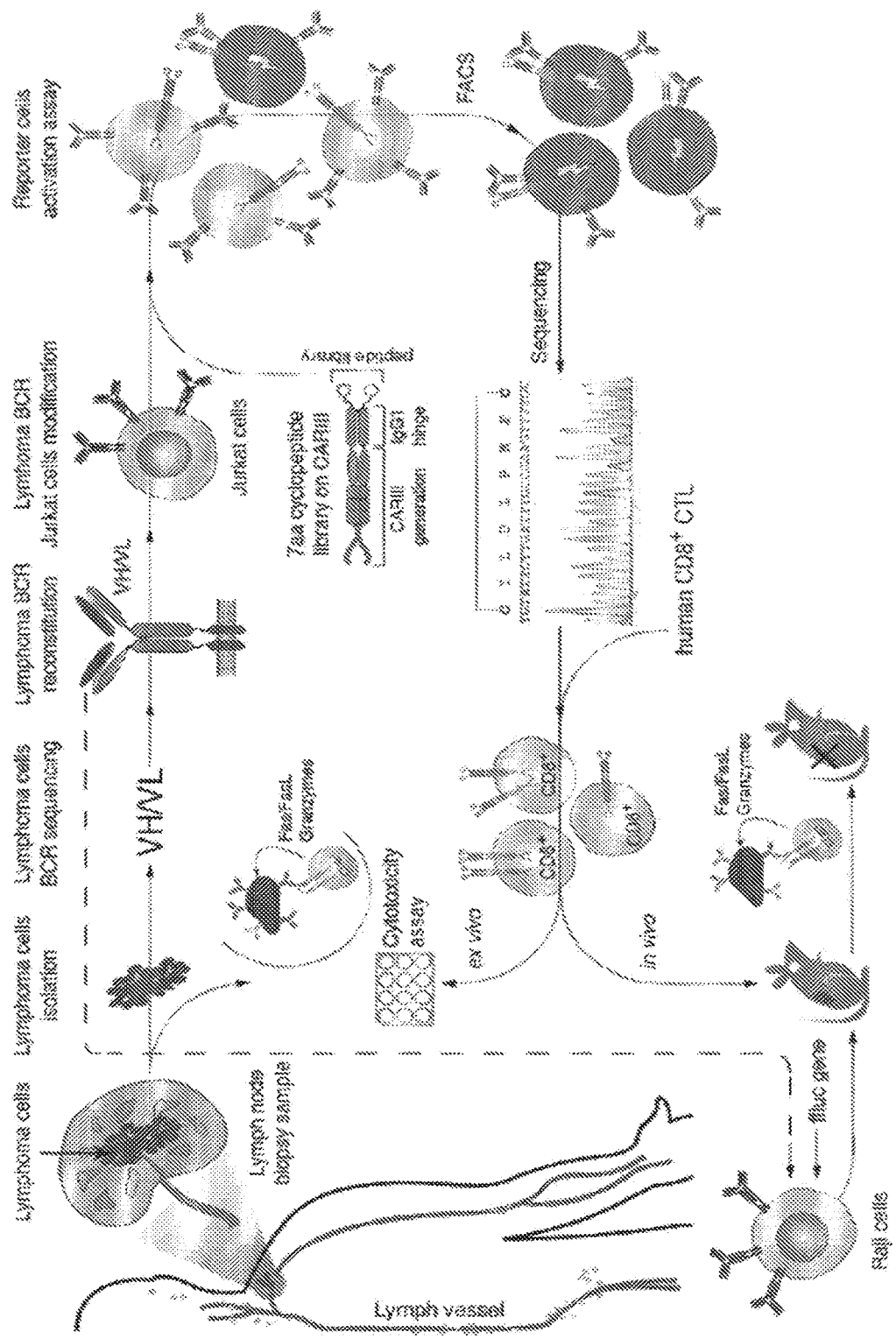
FIG. 1 is a schematic diagram showing the workflow for selection of ligands for the personalized follicular lymphoma CAR-T therapy. A lymph node biopsy sample from a patient with Follicular lymphoma is isolated and the collected tumor cells are used for identification of the malignant BCR genes after which they are reconstituted as a membrane bound BCR using PDGFR as a membrane anchor. The reconstituted malignant BCR, co-expressed with the cyclopeptide-CAR library on the surface of the Jurkat cell line are used as a reporter-cell system for selection of the tumor cell targeting ligand. Following several rounds of panning, the selected peptide ligands fused to the chimeric antigen receptor are sequenced and may be immediately used for generation of the therapeutic T lymphocytes modified by tumor-specific CAR. The sequences top to bottom correspond to SEQ ID NOs: 31 and 32.

The disclosure provides methods for treatment of B cell malignancies using personalized medicine. More particularly, the methods provide for isolating a B cell receptor from a B cell malignancy in a subject, identifying a ligand for the B cell receptor, and then treating the subject with the B cell receptor ligand coupled to a therapeutic agent, e.g., a CART cell in which the B cell receptor ligand comprises the antigen binding domain. In some embodiments, the methods of the disclosure use an autocrine-based format to identify B cell receptor ligands specific to a tumor. By co-expressing a B cell receptor and a library of putative B cell receptor ligands, a B cell receptor ligand can be identified by its binding to the B cell receptor. Alternatively, the B cell receptor ligand can be identified by phage display. The B cell receptor ligand can be an effective therapeutic when coupled to a therapeutic agent because it can target the therapeutic agent to the B cell malignancy by binding the B cell receptor. The methods described herein are particularly useful for treating B cell malignancies because B cell tumors are clonal populations having B cell receptors that are present in all of the cells of the tumor and only in the cells of the tumor. This allows for the identification of a personalized therapeutic target with no or very little off target effects.

In some embodiments, the methods described herein utilize autocrine signaling. As such, the methods described herein make use of autocrine signaling to identify novel therapeutics for treating B cell malignancies. As is used herein, "autocrine signaling" refers to a form of cell signaling in which a cell secretes a hormone or chemical messenger, e.g., an antigen, that binds to autocrine receptors, e.g., B cell receptors, on that same cell, leading to changes in the cell.

As an example, B cell receptor ligands may be identified by co-expressing a B cell receptor from a tumor and a CAR in a T cell, where the extracellular domain of the CAR comprises a peptide from a combinatorial peptide library. Activation of the T cell by the CAR indicates that the extracellular domain of the CAR has bound the B cell receptor and the peptide from the peptide library is a B cell ligand.

Once a B cell receptor ligand is identified, a patient can be treated with the ligand attached to a therapeutic agent. Therapeutic agents can comprise chemotherapeutic drugs, immunotherapy, or radioactive isotopes. A CAR comprising the B cell receptor ligand can comprise a therapeutic agent. The CAR can be the same CAR used to identify the B cell receptor ligand, allowing for particularly fast identification of a personalized therapeutic target and synthesis of personalized medicine.

The whole process, from diagnosis to treatment can be completed in a short period of time, e.g., within several weeks.

The disclosure also provides methods for treatment of cancer by administering CAR-expressing T-cells, wherein the CAR comprises an antigen binding domain that specifically binds a cancer-specific antigen in a cancer-specific manner; and a vaccine comprising a polypeptide or a nucleic acid expressing the same cancer-specific antigen, or a cancer-specific fragment thereof. It has surprisingly been discovered that when a CAR specific for a cancer antigen and that same antigen are administered to a subject, the two have a synergistic effect on a reduction in tumor volume.

In some embodiments, the CAR-expressing T cells comprise the CAR with the putative B cell receptor ligand, and the vaccine comprises a fragment or all of the B cell receptor. In some embodiments, the CAR-expressing T cells comprise an antibody fragment to an antigen that is specific to cancer cells and the vaccine comprises a fragment or all of that same antigen.

B Cell Receptors

The B-cell receptor or BCR is a transmembrane receptor protein located on the outer surface of B cells. The receptor's binding moiety is composed of a membrane-bound antibody that, like all antibodies, has a unique and randomly determined antigen-binding site generated by V(D)J recombination. When a B cell is activated by its first encounter with an antigen that binds to its receptor (its "cognate antigen"), the cell proliferates and differentiates to generate a population of antibody-secreting plasma B cells and memory B cells.

The BCR complexes with CD79, a transmembrane protein, and generates a signal following recognition of antigen by the BCR. CD79 is composed of two distinct chains, CD79A and CD79B, which form a heterodimer on the surface of a B cell stabilized by disulfide bonding. CD79a and CD79b are both members of the immunoglobulin superfamily. Both CD79 chains contain an immunoreceptor tyrosine-based activation motif (ITAM) in their intracellular tails that they use to propagate a signal in a B cell, in a similar manner to CD3-generated signal transduction observed during T cell receptor activation on T cells.

As used herein, the term "antibody" refers to a protein that includes at least one immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. An antibody can have the structural features of IgA, IgG, IgE, IgD, IgM (as well as subtypes thereof).

The VH and VL regions can be further subdivided into regions of hypervariability, termed "complementarity determining regions" ("CDR"), interspersed with regions that are more conserved, termed "framework regions" ("FR"). The extent of the framework region and CDRs has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, see also www.hgmp.mrc.ac.uk). Kabat definitions are used herein. Each VH and VL is typically composed of three CDRs and four FRs, arranged from amino-terminus to carboxy-terminus in the following order: FR1, CDR1, FR2, CDR2, FR3, CDR3, FR4.

The VH or VL chain of the antibody can further include a heavy or light chain constant region, to thereby form a heavy or light immunoglobulin chain, respectively. In one embodiment, the antibody is a tetramer of two heavy immunoglobulin chains and two light immunoglobulin chains, wherein the heavy and light immunoglobulin chains are inter-connected by, e.g., disulfide bonds. In IgGs, the heavy chain constant region includes three immunoglobulin domains, CH1, CH2 and CH3.

B-cell malignancies represent a diverse collection of diseases, including most non-Hodgkin's lymphomas (NHL), some leukemias, and myelomas. Examples include chronic lymphocytic leukemia, follicular lymphoma, mantle cell lymphoma and diffuse large B-cell lymphoma. B cell malignancies can be characterized as indolent or aggressive. Indolent malignancies, such as follicular lymphoma, small lymphocytic lymphoma and marginal zone lymphoma, are characterized by slow growth and a high initial response rate, followed by a relapsing and progressive disease course. Aggressive lymphomas, such as diffuse large B-cell lymphoma, mantle cell lymphoma and Burkitt's lymphoma, are characterized by rapid growth and lower initial response rates, with shorter overall survival (OS).

B cell malignancies are characterized in that they are clonal populations of B cells. Since they are clonal populations of B cells, each cancerous cell in the population of cancer cells, e.g., a tumor, has the same B cell receptor. As such, B cell receptors on cancerous cells are tumor specific antigens that can be targeted by the ligand (or "antigen") of the BCR.

Accordingly, disclosed herein are methods for identifying BCR ligands. Once identified, BCR ligands can be used, for example, as a cancer treatment. Therapeutic agents can be targeted to cancer cells via the interaction between the BCR and the BCR ligand.

In some embodiments, the methods described herein comprise identifying or providing a B cell receptor, e.g., expressed in cancer cells. In some embodiments, identifying or providing a B cell receptor comprises acquiring a sample from a subject. In some embodiments, the sample is a fluid sample, e.g., blood. In some embodiments, the sample is a tissue sample. In some embodiments, the sample comprises a, e.g., a tumor sample or a biopsy. In some embodiments, the biopsy is a lymph node biopsy.

In some embodiments, the sample is from a subject having or suspected of having cancer. In some embodiments, the cancer is a B cell malignancy. In some embodiments, the cancer is a lymphoma. In some embodiments, the cancer is selected from diffuse large B-cell lymphoma (DLBCL), follicular lymphoma, marginal zone B-cell lymphoma (MZL) or mucosa-associated lymphatic tissue lymphoma (MALT), chronic lymphocytic leukemia (CLL), mantle cell lymphoma (MCL), Burkitt's lymphoma, lymphoplasmacytic lymphoma, nodal marginal zone B cell lymphoma (NMZL), splenic marginal zone lymphoma (SMZL), intravascular large B-cell lymphoma, primary effusion lymphoma, lymphomatoid granulomatosis, primary central nervous system lymphoma, ALK-positive large B-cell lymphoma, plasmablastic lymphoma, large B-cell lymphoma arising in HHV8-associated multicentric Castleman's disease, and B-cell lymphoma.

In some embodiments, the subject is determined to have any of the cancers described herein. In some embodiments, the subject is determined to have a B cell malignancy. In some embodiments, the subject is determined to have lymphoma. In some embodiments, the subject is determined to have one or more single-nucleotide polymorphisms associated with cancer, e.g., a B cell malignancy and/or lymphoma. As used herein "single-nucleotide polymorphism" (SNP) refers to a DNA sequence variation occurring when a single nucleotide—A, T, C or G—in the genome (or other shared sequence) differs between members of a biological species or paired chromosomes in an individual.

In some embodiments, identifying or providing a B cell receptor comprises extracting RNA out of the cells of the sample. Methods for extracting RNA out of cells are well known to those of skill in the art and include, for example, phenol/chloroform based extraction methods, or the use of the RNAeasy Kit™ (Qiagen).

In some embodiments, identifying or providing a B cell receptor comprises synthesizing cDNA out of extracted RNA. Methods for producing cDNA are well known to those of skill in the art and comprises the formation of cDNA from mRNA by reverse transcriptase.

In some embodiments, identifying or providing a B cell receptor comprises sequencing the cDNA. The type of sequencing performed can be, for example, pyrosequencing, single-molecule real-time sequencing, ion torrent sequencing, sequencing by synthesis, sequencing by ligation (SOLiD™), and chain termination sequencing (e.g., Sanger sequencing). Sequencing methods are known in the art and commercially available (see, e.g., Ronaghi et al.; Uhlén, M; Nyrén, P (1998). "A sequencing method based on real-time pyrophosphate". Science 281 (5375): 363; and Ronaghi et al.; Karamohamed, S; Pettersson, B; Uhlén, M; Nyrén, P (1996). "Real-time DNA sequencing using detection of pyrophosphate release". Analytical Biochemistry 242 (1): 84-9.; and services and products available from Roche (454 platform), Illumina (HiSeq and MiSeq systems), Pacific Biosciences (PACBIO RS II), Life Technologies (Ion Proton™ systems and SOLiD™ systems)).

In some embodiments, the B cell receptor is cloned into an expression vector for expressing the B cell receptor in T cells using methods described herein.

In some embodiments, the B cell receptor is cloned into an scFv format using a vector, e.g., a pComb3X vector.

In some embodiments, the scFv form of the B cell receptor is cloned into a vector for expressing the antibody molecules as dimers with the variable region in the plasma membrane with their binding sites facing the solvent. In some embodiments, the scFv form of the B cell receptor is cloned into a vector containing a linker. In some embodiments, the linker is a a flexible linker to a membrane-spanning domain of the platelet-derived growth factor receptor. In some embodiments, the vector further comprises a constant domain of antibody, e.g., Fc, e.g., IgG1 Fc.

Identifying B-Cell Receptor Ligands

In some embodiments, the methods described herein comprise identifying a B cell receptor ligand. Once the B cell receptor is identified, the ligand of the B cell receptor is identified by contacting the B cell receptor with putative B cell receptor ligands, e.g., a library of putative B cell receptor ligands.

In some embodiments, the methods described herein provide for co-expressing B cell receptors and a library of putative B cell receptor ligands in cells, e.g., T cells, and detecting binding of the B cell receptor to a putative B cell receptor ligand, thereby identifying a unique B cell receptor ligand.

In some embodiments, detecting binding comprises measuring the level of B cell receptor signaling. When the B cell receptor and a putative B cell receptor ligand are both expressed, e.g., in a B cell, if the putative B cell receptor ligand is a ligand of the B cell receptor, the binding of the B cell receptor will initiate a signaling cascade. It some embodiments, detecting binding comprises measuring the expression of genes regulated by BCR signaling.

In some embodiments, the methods described herein provide for co-expressing B cell receptors and a library of CARs comprising putative B cell receptor ligand domains in T cells and detecting binding of the B cell receptor to a putative B cell receptor ligand by identifying activation of the T cell by the CAR, thereby identifying a unique B cell receptor ligand.

In some embodiments, T cells are transduced or transfected with nucleic acids encoding B cell receptors and CARs and T cell activation is measured after a period of time. In some embodiments, T cell activation is measured 2, 4, 6, 8, 12, 16, or 20 hours, or 1, 1.5, 2, 2.5, 3, 3.5, 4, 4.5, or 5 days after transduction or transfection, e.g., 2 days after transduction or transfection.

In some embodiments, co-expressing the B cell receptors and CARs comprises culturing T cells transduced or transfected with nucleic acids encoding B cell receptors and CARs in culture media. Media for culturing T cells are well known to those of skill in the art. In some embodiments, T cells are cultured in DMEM or RPMI medium. In some embodiments, the medium is supplemented with FBS, e.g, 5-20% FBS, e.g., 10% FBS. In some embodiments, the medium is supplemented with HEPES, e.g., 1-100 mM HEPES, e.g., 10 mM HEPES. In some embodiments, the medium is supplemented with penicillin, e.g., 10-500 U/ml penicillin, e.g., 100 U/ml penicillin. In some embodiments, the medium is supplemented with streptomycin, e.g., 10-500 ug/ml streptomycin, e.g., 100 ug/ml streptomycin. In some embodiments, the medium is supplemented with L-alanyl-L-glutamine, e.g., 0.1-10 mM L-alanyl-L-glutamine, e.g., 2 mM L-alanyl-L-glutamine.

In some embodiments, measuring the level of T cell activation comprises measuring the nucleic acid or protein level of a gene expressed in activated T cells. Examples of genes downregulated during T cell activation include, for example, L-selectin, CD127, and BCL-2. Examples of genes downregulated during T cell activation include, for example CD69, CD25, CD40L, CD44, Ki67, and KLRG1. In some embodiments, the T cell comprises a fluorescent protein reporter gene under the control of a transcription factor that activates transcription when the T cell is activated and measuring activation comprises measuring the amount of fluorescent protein produced. In some embodiments, the transcription factor is Jun, NF-κB or Rel.

Gene expression can be measured at either the RNA or protein level. Assays for detecting RNA include, but are not limited to, Northern blot analysis, RT-PCR, sequencing technology, RNA in situ hybridization (using e.g., DNA or RNA probes to hybridize RNA molecules present in the sample), in situ RT-PCR (e.g., as described in Nuovo G J, et al. Am J Surg Pathol. 1993, 17: 683-90; Komminoth P, et al. Pathol Res Pract. 1994, 190: 1017-25), and oligonucleotide microarray (e.g., by hybridization of polynucleotide sequences derived from a sample to oligonucleotides attached to a solid surface (e.g., a glass wafer with addressable location, such as Affymetrix microarray (Affymetrix®, Santa Clara, CA)).

Assays for detecting protein levels include, but are not limited to, immunoassays (also referred to herein as immune-based or immuno-based assays, e.g., Western blot, ELISA, proximity extension assays, and ELISpot assays), Mass spectrometry, and multiplex bead-based assays. Other examples of protein detection and quantitation methods include multiplexed immunoassays as described for example in U.S. Pat. Nos. 6,939,720 and 8,148,171, and published U.S. Patent Application No. 2008/0255766, and protein microarrays as described for example in published U.S. Patent Application No. 2009/0088329.

In some embodiments, once an activated T cell is identified, the CAR expressed in the T cell is identified. Accordingly, in some embodiments, protocols for identifying activated T cells allow for the identification of activated T cells and the separation of activated T cells from unactivated T cells. One example of such a protocol is flow cytometry. The use of flow cytometry generally, and Fluorescence-activated cell sorting (FACS) in particular, are readily known to those of skill in the art for the purpose of cell sorting based on a variety of properties. In FACS, a heterogeneous mixture of biological cells can be sorted into two or more containers, one cell at a time, based upon the specific light scattering and fluorescent characteristics of each cell. This allows, for example, for cells to be sorted on the basis of fluorescent markers. Accordingly, in certain embodiments, T cell activation can be measured by levels of a fluorescently marked or labeled transcript or protein. In some embodiments, the expression level of a protein, e.g., a cell surface localized protein, e.g., a protein upregulated or downregulated in activated T cells described herein, can be measured by contacting the cells with an antibody coupled, covalently or non-covalently, to a fluorescent label. In some embodiments, the antibody targets the protein upregulated or downregulated in activated T cells. This can allow the cells to be sorted based on expression level of a protein upregulated or downregulated in activated T cells, thereby allowing separation of activated from unactivated T cells. In one exemplary embodiment, activated T cells can be identified by binding of the T cells to GFP-labeled anti-CD69 antibody.

In some embodiments, detecting binding between a putative B cell receptor ligand and a cell expressing a B cell receptor comprises visualizing binding of the putative B cell receptor ligand to the cell expressing the B cell receptor. For example, in some embodiments, the ligand is tagged to allow for visualization of the localization of the ligand. Suitable tags include, for example, fluorescent genes such as GFP, YFP, RFP and the like. In some embodiments, localization of the putative B cell receptor ligand to the cell expressing the B cell receptor can be assessed using any suitable method known by those of skill in the art, e.g., fluorescence microscopy, immunohistochemistry, or FACS. In some embodiments, a B cell receptor ligand binds to the cells expressing the B cell receptor and does not bind to the same cell type when the B cell receptor is not expressed.

In some embodiments the library pf putative B cell receptor ligands is contacted to the B cell receptor by phage display.

"Phage display" is a technique by which variant polypeptides are displayed as fusion proteins to a coat protein on the surface of phage, e.g. filamentous phage, particles. A utility of phage display lies in the fact that large libraries of randomized protein variants can be rapidly and efficiently sorted for those sequences that hind to a target molecule with high affinity. Display of peptides and proteins libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, Curr. Opin. Struct. Biol., 1992, 3:355-362 and references cited therein. In monovalent phage display, a protein or peptide library is fused to a gene III or a portion thereof and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, Methods: A companion to Methods in Enzymology, 1991, 3:205-216.

Phage display of proteins, peptides and mutated variants thereof, including constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, contacting the recombinant phage particles with a target molecule so that at least a portion of the particle bind to the target, separating the particles which bind from those that do not are known and may be used with the transformation method of the invention. See U.S. Pat. No. 5,750,373; WO 97/09446; U.S. Pat. Nos. 5,514,548; 5,498,538; 5,516,637; 5,432,018; WO 96/22393; U.S. Pat. Nos. 5,658,727; 5,627,024; WO 97/29185; O'Boyle et al, 1997, *Virology*, 236:338-347; Soumillion et al, 1994, *Appl. Biochem. Biotech.*, 47:175-190; O'Neil and Hoess, 1995, *Curr. Opin. Struct. Biol.*, 5:443-449; Makowski, 1993, *Gene*, 128:5-11, Dunn, 1996, *Curr. Opin. Struct. Biol.*, 7:547-553; shoo and Klug, 1995, *Curr. Opin. Struct. Biol.*, 6:431436; Bradbury and Cattaneo, 1995, *TINS*, 18:242-249; Cortese et al., 1995, *Curr. Opin. Struct. Biol.*, 6:73-80; Allen et al., 1995, *TIBS*, 20:509-516; Lindquist and Naderi, 1995, *FEMS Micro. Rev.*, 17:33-39; Clarkson and Wells, 1994, *Tibtech*, 12:173-184; Barbas, 1993. *Curr. Opin. Biol.*, 4:526.130; McGregor, 1996, *Mol. Biotech.*, 6:155-162; Cortese et al., 1996, *Curr. Opin. Biol.*, 7:616-621; McLafferty et al., 1993, *Gene*, 128:29-36. Using phage display, in some embodiments, putative B cell receptor ligands capable of binding to the B cell receptor as described herein are isolated from a suitable library. Exemplary putative B cell receptor ligand libraries include phage-peptide libraries such as New England Biolabs Ph.D.-7 and Ph.D.-12 libraries. Methods of generating peptide libraries and screening these libraries are also disclosed in U.S. Pat. Nos. 5,723,286; 5,432,018; 5,580,717; 5,427,908; and 5,498,530. See also U.S. Pat. Nos. 5,770,434; 5,734,018; 5,698,426; 5,763,192; and 5,723,323. In the selection process, a putative B cell receptor ligand library can be probed with the target B cell receptor or a fragment thereof and members of the library that are capable of binding to the B cell receptor can be isolated, typically by retention on a support. Such screening process may be performed by multiple rounds (e.g., including both positive and negative selections) to enrich the pool of putative B cell receptor ligands capable of binding to the B cell receptor. In some embodiments, negative selection is performed in each round of panning. Individual clones of the enriched pool can then be isolated and further characterized to identify those having desired binding activity and biological activity. Sequences of the putative B cell receptor ligands can also be determined via conventional methodology.

As an example, phage displays typically use a covalent linkage to bind the protein (e.g., putative B cell receptor ligand domain) component to a bacteriophage coat protein. The linkage results from translation of a nucleic acid encoding the putative B cell receptor ligand domain component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al. (1998) *Immunotechnology* 4:1-20; Hoogenboom et al. (2000) *Immunol Today* 2:371-8 and Hoet et al. (2005) *Nat Biotechnol.* 23(3)344-8. Bacteriophage displaying the putative B cell receptor ligand domain component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be selected, and then the nucleic acid may be isolated and sequenced.

After display library members are isolated for binding to the target antigen, each isolated library member can be also tested for its ability to bind to a non-target molecule to evaluate its binding specificity. Examples of non-target molecules include streptavidin on magnetic beads, blocking agents such as bovine serum albumin, non-fat bovine milk, soy protein, any capturing or target immobilizing monoclonal antibody, or non-transfected cells which do not express the target. A high-throughput ELISA screen can be used to obtain the data, for example. The ELISA screen can also be used to obtain quantitative data for binding of each library member to the target as well as for cross species reactivity to related targets or subunits of the target antigen and also under different condition such as pH 6 or pH 7.5. The non-target and target binding data are compared (e.g., using a computer and software) to identify library members that specifically bind to the target.

Putative B Cell Receptor Ligands

Provided herein are methods of identifying unique B cell receptor ligands, e.g., for cancer therapy, comprising identifying a putative unique B cell receptor ligand as binding a unique B cell receptor.

In some embodiments, the putative B cell receptor ligand comprises a polypeptide. In some embodiments, a putative B cell receptor ligand comprises a cyclopeptide. In some embodiments, a putative B cell receptor ligand comprises a peptoid. In some embodiments, a putative B cell receptor ligand comprises a cyclopeptoid. In some embodiments, the putative B cell receptor ligand comprises a polysaccharide. In some embodiments, the putative B cell receptor ligand comprises a lipid. In some embodiments, the putative B cell receptor ligand comprises a small molecule.

In some embodiments, the putative B cell receptor ligand comprises an amino acid sequence that encodes a portion or all of a cellular protein. In some embodiments, the putative B cell receptor ligand comprises an amino acid sequence that does not encode a portion or all of a cellular protein.

In some embodiments, the putative B cell receptor ligand is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acids in length, e.g., 9 amino acids in length. In some embodiments, the putative B cell receptor ligand is less than 20, less than 15, or less than 10 amino acids in length. In some embodiments, the putative B cell receptor ligand is 2-20, 5-15, or 7-10 amino acids in length.

In some embodiments, the putative B cell receptor ligand comprises the sequence $YX_nZ$. In some embodiments, Y and Z are polar uncharged amino acids. In some embodiments, Y and Z are C or conservative substitutions of C, e.g., S, A, M, or T. In some embodiments, the putative B cell receptor ligand comprises the sequence $CX_nC$. In some embodiments, the putative B cell receptor ligand comprises the sequence $SX_nS$. In some embodiments, the putative B cell receptor ligand comprises the sequence $CX_nS$. In some embodiments, the putative B cell receptor ligand comprises the sequence $SX_nC$. In some embodiments, X is any of the 20 amino acids encoded by DNA. In some embodiments, n is 1, 2, 3, 4, 5, 6, 7, 8, 9, 10, 11, 12, 13, 14, 15, 16, 17, 18, 19, or 20, e.g., n is 7. In some embodiments, n is 15 or less, 12 or less, or 9 or less. In some embodiments, n is 2-15, 5-10, or 6-8. In some embodiments, the putative B cell receptor ligand comprises any of SEQ ID NOs: 1-3.

In some embodiments, the putative B cell receptor ligand comprises a cyclopeptide with the sequence $CX_nC$, and the N- and C-terminal Cys form a Cys-Cys interaction, circularizing the cyclopeptide.

Also provided herein are libraries of putative B cell receptor ligands.

In some embodiments, the library of putative B cell receptor ligands is generated from a cDNA library and with each putative B cell receptor ligand comprising a portion or all of a cDNA.

In some embodiments, the library of putative B cell receptor ligands comprises a peptide library. In some embodiments, the peptide library is a combinatorial peptide library. In some embodiments, the putative B cell receptor ligands in the peptide library comprises the sequence $YX_nZ$ with the putative B cell receptor ligands differing in $X_n$ sequence. In some embodiments, Y and Z are polar uncharged amino acids. In some embodiments, Y and Z are C or conservative substitutions of C, e.g., S, A, M, or T. In some embodiments, the putative B cell receptor ligands in the peptide library comprises the sequence $CX_nC$ with the putative B cell receptor ligands differing in $X_n$ sequence. In some embodiments, the putative B cell receptor ligands in the peptide library comprises the sequence $SX_nS$ with the putative B cell receptor ligands differing in $X_n$ sequence. In some embodiments, the putative B cell receptor ligands in the peptide library comprises the sequence $CX_nS$ with the putative B cell receptor ligands differing in $X_n$ sequence. In some embodiments, the putative B cell receptor ligands in the peptide library comprises the sequence $SX_nC$ with the putative B cell receptor ligands differing in $X_n$ sequence. In some embodiments, X is any of the 20 amino acids encoded by DNA. In some embodiments, n is 1, 2, 3, 4, 5, 6, 7, 8, 9, 10, 11, 12, 13, 14, 15, 16, 17, 18, 19, or 20, e.g., n is 7. In some embodiments, n is 15 or less, 12 or less, or 9 or less. In some embodiments, n is 2-15, 5-10, or 6-8. In some embodiments, $X_n$ sequence is generated by PCR with oligonucleotides having degenerate NNN, NNK, or NNS codons at the X positions. In some embodiments, the degenerate codons are NNK codons.

In some embodiments the putative B cell receptor ligand comprises the antigen binding domain of a CAR. In some embodiments the putative B cell receptor ligand is linked to a phage, e.g., as a component of a phage display library.

Chimeric Antigen Receptors (CARs)

Disclosed herein are methods for identifying B cell receptor ligands by co-expressing B cell receptors and CARs having a putative B cell receptor ligand domain as an extracellular domain and measuring T cell activation.

Also disclosed herein are methods for treating cancer by treating a subject with CAR-expressing T-cells, wherein the CAR comprises an antigen binding domain that specifically binds a cancer-specific antigen in a cancer-specific manner and a vaccine comprising a polypeptide or a nucleic acid expressing the cancer-specific antigen, or a cancer-specific fragment thereof.

In one aspect an exemplary CAR construct disclosed herein comprise an optional leader sequence, an extracellular putative B cell receptor ligand domain, a hinge, a transmembrane domain, and an intracellular stimulatory domain. In one aspect an exemplary CAR construct comprises an optional leader sequence, an extracellular putative B cell receptor ligand domain, a hinge, a transmembrane domain, an intracellular costimulatory domain and an intracellular stimulatory domain.

The term "Chimeric Antigen Receptor" or alternatively a "CAR" refers to a recombinant polypeptide construct comprising at least an extracellular ligand domain, a transmembrane domain and a cytoplasmic signaling domain (also referred to herein as "an intracellular signaling domain") comprising a functional signaling domain derived from a stimulatory molecule as defined below. In some embodiments, the domains in the CAR polypeptide construct are in the same polypeptide chain, e.g., comprise a chimeric fusion protein. In some embodiments, the domains in the CAR polypeptide construct are not contiguous with each other.

Antigen Binding Domain

In some embodiments, the CAR described herein comprises an extracellular domain. In some embodiments, the extracellular domain comprises an antigen binding domain.

In some embodiments, the antigen binding domain is a putative B cell receptor ligand domain comprising a putative B cell receptor ligand, e.g., a putative B cell receptor ligand described herein. In some embodiments, provided herein are a library of CARs with the CARs differing in their antigen binding domains, e.g., putative B cell receptor ligand domains. In some embodiments, each CAR within the library comprises a distinct antigen binding domain, e.g., putative B cell receptor ligand domain. In some embodiments, the library of CARs comprises an extracellular domain and the extracellular domain comprises the library of antigen binding domains, e.g., putative B cell receptor ligands described herein.

In some embodiments, the putative B cell receptor ligand domain further comprises an Fc domain, which is CH2 and CH3 of a heavy chain constant region. In some embodiments, the Fc domain is from a heavy chain constant region chosen from, e.g., the heavy chain constant regions of IgG1, IgG2, IgG3, IgG4, IgM, IgA1, IgA2, IgD, and IgE; particularly, chosen from, e.g., the (e.g., human) heavy chain constant regions of IgG1, IgG2, IgG3, and IgG4.

In some embodiments, antigen binding domain comprises an immunoglobulin chain or fragment thereof, comprising at least one immunoglobulin variable domain sequence. The term "antigen binding domain" encompasses antibodies and antibody fragments. In an embodiment, an antibody molecule is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In an embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

In some embodiments, the antigen binding domain specifically binds a cancer-specific antigen.

In some embodiments, the CARs of the present invention includes CARs comprising an antigen binding domain (e.g., antibody or antibody fragment) that binds to a MHC presented peptide. Normally, peptides derived from endogenous proteins fill the pockets of Major histocompatibility complex (MHC) class I molecules, and are recognized by T cell receptors (TCRs) on CD8+ T lymphocytes. The WIC class I complexes are constitutively expressed by all nucleated cells. In cancer, virus-specific and/or tumor-specific peptide/WIC complexes represent a unique class of cell surface targets for immunotherapy. TCR-like antibodies targeting peptides derived from viral or tumor antigens in the context of human leukocyte antigen (HLA)-A1 or HLA-A2 have been described (see, e.g., Sastry et al., J Virol. 2011 85(5):1935-1942; Sergeeva et al., Blood, 2011 117(16): 4262-4272; Verma et al., J Immunol 2010 184(4):2156-2165; Willemsen et al., Gene Ther 2001 8(21):1601-1608; Dao et al., Sci Transl Med 2013 5(176):176ra33; Tassev et al., Cancer Gene Ther 2012 19(2):84-100). For example, TCR-like antibody can be identified from screening a library, such as a human scFv phage displayed library.

The antigen binding domain can be any protein that binds to the antigen including but not limited to a monoclonal antibody, a polyclonal antibody, a recombinant antibody, a human antibody, a humanized antibody, and a functional fragment thereof, including but not limited to a single-domain antibody such as a heavy chain variable domain (VH), a light chain variable domain (VL) and a variable domain (VHH) of camelid derived nanobody, and to an alternative scaffold known in the art to function as antigen binding domain, such as a recombinant fibronectin domain, and the like. In some instances, it is beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment.

In one aspect, the antigen binding domain comprises a human antibody or an antibody fragment.

In one aspect, the antigen binding domain comprises a humanized antibody or an antibody fragment.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, for example improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody or antibody fragment has one or more amino acid residues remaining in it from a source which is nonhuman. These nonhuman amino acid residues are often referred to as "import" residues, which are typically taken from an "import" variable domain. As provided herein, humanized antibodies or antibody fragments comprise one or more CDRs from nonhuman immunoglobulin molecules and framework regions wherein the amino acid residues comprising the framework are derived completely or mostly from human germline. Multiple techniques for humanization of antibodies or antibody fragments are well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized antibodies and antibody fragments, substantially less than an intact human variable domain has been substituted by the corresponding sequence from a nonhuman species. Humanized antibodies are often human antibodies in which some CDR residues and possibly some framework (FR) residues are substituted by residues from analogous sites in rodent antibodies. Humanization of antibodies and antibody fragments can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

In some embodiments, an antigen binding domain is derived from a display library. A display library is a collection of entities; each entity includes an accessible polypeptide component and a recoverable component that encodes or identifies the polypeptide component. The polypeptide component is varied so that different amino acid sequences are represented. The polypeptide component can be of any length, e.g. from three amino acids to over 300 amino acids. A display library entity can include more than one polypeptide component, for example, the two polypeptide chains of a Fab. In one exemplary embodiment, a display library can be used to identify an antigen binding domain. In a selection, the polypeptide component of each member of the library is probed with the antigen, or a fragment there, and if the polypeptide component binds to the antigen, the display library member is identified, typically by retention on a support.

Retained display library members are recovered from the support and analyzed. The analysis can include amplification and a subsequent selection under similar or dissimilar conditions. For example, positive and negative selections can be alternated. The analysis can also include determining the amino acid sequence of the polypeptide component and purification of the polypeptide component for detailed characterization.

A variety of formats can be used for display libraries. Examples include the phage display. In phage display, the protein component is typically covalently linked to a bacteriophage coat protein. The linkage results from translation of a nucleic acid encoding the protein component fused to the coat protein. The linkage can include a flexible peptide linker, a protease site, or an amino acid incorporated as a result of suppression of a stop codon. Phage display is described, for example, in U.S. Pat. No. 5,223,409; WO 92/18619; WO 91/17271; WO 92/20791; WO 92/15679; WO 93/01288; WO 92/01047; WO 92/09690; WO 90/02809. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be picked, the nucleic acid isolated and sequenced.

Other display formats include cell based display (see, e.g., WO 03/029456), protein-nucleic acid fusions (see, e.g., U.S. Pat. No. 6,207,446), ribosome display, and *E. coli* periplasmic display.

In one aspect the CAR comprises a leader sequence at the amino-terminus (N-ter) of the antigen binding domain. In one aspect, the CAR further comprises a leader sequence at the N-terminus of the antigen binding domain, wherein the leader sequence is optionally cleaved from the antigen binding domain (e.g., aa scFv) during cellular processing and localization of the CAR to the cellular membrane. In some embodiments, the leader sequence is an interleukin 2 signal peptide.

Transmembrane Domain

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the CAR has bound to a target. A transmembrane domain of particular use in this invention may include at least the transmembrane region(s) of e.g., the alpha, beta or zeta chain of the T-cell receptor, CD28, CD3 epsilon, CD45, CD4, CD5, CD8 (e.g., CD8 alpha, CD8 beta), CD9, CD16, CD22, CD33, CD37, CD64, CD80, CD86, CD134, CD137, CD154. In some embodiments, a transmembrane domain may include at least the transmembrane region(s) of, e.g., KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2R beta, IL2R gamma, IL7R a, ITGA1, VLA1, CD49a, ITGA4, IA4, CD49D, ITGA6, VLA-6, CD49f, ITGAD, CD11d, ITGAE, CD103, rfGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, NKG2C, and CD19.

In some instances, the transmembrane domain can be attached to the extracellular region of the CAR, e.g., the ligand domain of the CAR, via a hinge, e.g., a hinge from a human protein. For example, in one embodiment, the hinge can be a human Ig (immunoglobulin) hinge, e.g., an IgG4 hinge, or a CD8a hinge.

Cytoplasmic Domain

The cytoplasmic domain or region of the present CAR includes an intracellular signaling domain. An intracellular signaling domain is capable of activation of at least one of the normal effector functions of the immune cell in which the CAR has been introduced.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

An "intracellular signaling domain," as the term is used herein, refers to an intracellular portion of a molecule. The intracellular signaling domain can generate a signal that promotes an immune effector function of the CAR containing cell, e.g., a CART cell or CAR-expressing NK cell. Examples of immune effector function, e.g., in a CART cell or CAR-expressing NK cell, include cytolytic activity and helper activity, including the secretion of cytokines. In embodiments, the intracellular signal domain transduces the effector function signal and directs the cell to perform a specialized function. While the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal. In an embodiment, the intracellular signaling domain can comprise a primary intracellular signaling domain. Exemplary primary intracellular signaling domains include those derived from the molecules responsible for primary stimulation, or antigen dependent simulation. In an embodiment, the intracellular signaling domain can comprise a costimulatory intracellular domain. Exemplary costimulatory intracellular signaling domains include those derived from molecules responsible for costimulatory signals, or antigen independent stimulation. For example, in the case of a CAR-expressing immune effector cell, e.g., CART cell or CAR-expressing NK cell, a primary intracellular signaling domain can comprise a cytoplasmic sequence of a T cell receptor, and a costimulatory intracellular signaling domain can comprise cytoplasmic sequence from co-receptor or costimulatory molecule.

A primary intracellular signaling domain can comprise a signaling motif which is known as an immunoreceptor tyrosine-based activation motif or ITAM. Examples of ITAM containing primary cytoplasmic signaling sequences include, but are not limited to, those derived from CD3 zeta, FcR gamma, FcR beta, CD3 gamma, CD3 delta, CD3 epsilon, CD5, CD22, CD79a, CD79b, CD278 ("ICOS"), FceRI, CD66d, DAP10, and DAP12.

The intracellular signalling domain of the CAR can comprise the primary signalling domain, e.g., CD3-zeta signaling domain, by itself or it can be combined with any other desired intracellular signaling domain(s) useful in the context of a CAR of the invention. For example, the intracellular signaling domain of the CAR can comprise a primary signalling domain, e.g., CD3 zeta chain portion, and a costimulatory signaling domain.

A costimulatory intracellular signaling domain refers to the intracellular portion of a costimulatory molecule. The intracellular signaling domain can comprise the entire intracellular portion, or the entire native intracellular signaling domain, of the molecule from which it is derived, or a functional fragment thereof. The term "costimulatory molecule" refers to the cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are required for an efficient immune response. Examples of such molecules include a MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CDIOO (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. For example, CD27 co-stimulation has been demonstrated to enhance expansion, effector function, and survival of human CART cells in vitro and augments human T cell persistence and antitumor activity in vivo (Song et al. Blood. 2012; 119(3):696-706).

Expression in Cells

In some embodiments, the methods described herein comprise expressing B cell receptors and putative B cell receptor ligands, e.g., CARs comprising putative B cell receptor ligands, in cells, e.g., T cells for identifying a B cell receptor ligand, e.g., for treatment of cancer. The methods described herein also comprise expressing CARs in T cells for cancer treatment.

In some embodiments, the disclosure encompasses DNA constructs for expressing CARs in cells, e.g., T cells. The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. For example, as is described herein, sequences of B cell receptors can be derived from cancer cells. Recombinant DNA and molecular cloning techniques used here are well known in the art and are described, for example, by Sambrook, J., Fritsch, E. F. and Maniatis, T. MOLECULAR CLONING: A LABORATORY MANUAL, 2nd ed.; Cold Spring Harbor Laboratory: Cold Spring Harbor, N.Y., 1989 (hereinafter "Maniatis"); and by Silhavy, T. J., Bennan, M. L. and Enquist, L. W. EXPERIMENTS WITH GENE FUSIONS; Cold Spring Harbor Laboratory: Cold Spring Harbor, N.Y., 1984; and by Ausubel, F. M. et al., IN CURRENT PROTOCOLS IN MOLECULAR BIOLOGY, published by Greene Publishing and Wiley-Interscience, 1987; (the entirety of each of which is hereby incorporated herein by reference).

Alternatively, the gene of interest can be produced synthetically, rather than cloned.

The present disclosure also provides vectors in which a DNA of the present disclosure is inserted. Vectors derived from retroviruses such as the lentivirus are suitable tools to achieve long-term gene transfer since they allow long-term, stable integration of a transgene and its propagation in daughter cells. Lentiviral vectors have the added advantage over vectors derived from onco-retroviruses such as murine leukemia viruses in that they can transduce non-proliferating cells, such as hepatocytes. They also have the added advantage of low immunogenicity. In another embodiment, the desired B cell receptor or CAR can be expressed in the cells by way of transposons.

A "lentivirus" as used herein refers to a genus of the Retroviridae family. Lenti viruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lenti viruses. Vectors derived from lenti viruses offer the means to achieve significant levels of gene transfer in vivo.

Expression of natural or synthetic nucleic acids encoding B cell receptors and CARs is typically achieved by operably linking a nucleic acid encoding the polypeptide expressing the B cell receptor or CAR or portions thereof to a promoter, and incorporating the construct into an expression vector. The vectors can be suitable for replication and integration into eukaryotes. Typical cloning vectors contain transcription and translation terminators, initiation sequences, and promoters useful for regulation of the expression of the desired nucleic acid sequence. The expression constructs of the disclosure may also be used for nucleic acid immunization and gene therapy, using standard gene delivery protocols. Methods for gene delivery are known in the art. See, e.g., U.S. Pat. Nos. 5,399,346, 5,580,859, 5,589,466, incorporated by reference herein in their entireties. In another embodiment, the disclosure provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, retrovirus vectors are used. A number of retrovirus vectors are known in the art. In some embodiments, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Factor-1a (EF-1a). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the disclosure is not limited to the use of constitutive promoters. Inducible promoters are also contemplated as part of the disclosure. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter. In some embodiments, the promoter is a EF-1a promoter.

In order to assess the expression of a B cell receptors or CAR or portions thereof, the expression vector to be introduced into a cell can also contain either a selectable marker gene or a reporter gene or both to facilitate identification and selection of expressing cells. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like, and fluorescent genes such as GFP, YFP, RFP and the like. In some embodiments, reporter genes or selectable marker genes are excluded from a CAR polypeptide used in a therapy as described herein.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity, antibiotic resistance or fluorescence. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means. In some embodiments, the host cell is a T cell.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An example of a colloidal system for use as a delivery vehicle in vitro and in vivo is a liposome (e.g., an artificial membrane vesicle).

Sources of Cells

In some embodiments, cells are transfected with nucleic acids expressing a B cell receptor and/or a CAR. The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

In some embodiments, the cells are mammalian cells. In some embodiments, the cells are human cells. In some embodiments, the cells are immune cells, e.g., B cells, T cells, or NK cells. In particular embodiments, the cells are T cells.

Immune cells (e.g., T cells) can be obtained from a number of sources, including peripheral blood mononuclear cells, bone marrow, lymph node tissue, cord blood, thymus tissue, tissue from a site of infection, ascites, pleural effusion, spleen tissue, and tumors. The immune cells (e.g., T cells) may also be generated from induced pluripotent stem cells or hematopoietic stem cells or progenitor cells. In some embodiments, any number of immune cell lines, including but not limited to T cell lines, including, for example, Hep-2, Jurkat, and Raji cell lines, available in the art, may be used. In some embodiments, immune cells (e.g., T cells) can be obtained from a unit of blood collected from a subject using any number of techniques known to the skilled artisan, such as Ficoll™ separation. In some embodiments, cells from the circulating blood of an individual are obtained by apheresis. The apheresis product typically contains lymphocytes, including T cells, monocytes, granulocytes, B cells, NK cells, other nucleated white blood cells, red blood cells, and platelets. In some embodiments, the cells collected by apheresis may be washed to remove the plasma fraction and to place the cells in an appropriate buffer or media for subsequent processing steps. In some embodiments, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter CytoMate, or the Haemonetics Cell Saver 5) according to the manufacturer's instructions. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the apheresis sample may be removed and the cells directly resuspended in culture media.

In some embodiments, immune cells (e.g., T cells) are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$T cells, can be further isolated by positive or negative selection techniques.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for $CD4^+$ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express $CD4^+$, $CD25^+$, $CD62L^{hi}$, $GITR^+$, and $FoxP3^+$.

Alternatively, in certain embodiments, T regulatory cells are depleted by anti-C25 conjugated beads or other similar method of selection.

Methods of Treatment

Provided herein are methods of treatment using the B cell receptor ligands identified herein. In particular, provided herein are methods for rapid treatment of B cell malignancies. For example, the methods described herein allow for the rapid identification of a B cell receptor ligand by co-expressing a CAR having a putative B cell receptor ligand and a B cell receptor in a T cell, and identifying binding of the putative B cell receptor ligand to the B cell receptor by activation of the B cell, and in some embodiments, the same CAR used in identification of the B cell receptor ligand can be used for treatment, allowing for the rapid identification and treatment of B cell malignancies. In some embodiments, provided herein are methods of treatment using B cell receptor ligands that activate a T cell when a CAR comprising the B cell ligand is co-expressed with the B cell receptor of the lymphoma cells of a subject being treated in T cells.

In some embodiments, a subject is treated with a B cell receptor ligand coupled to a therapeutic agent.

In some embodiments, the B cell receptor ligand coupled to a therapeutic agent comprises a therapeutic CAR, e.g., a CAR described herein, expressed in a T cell as is described herein, e.g., a CAR-T cell. In some embodiments, the therapeutic CAR comprises a CAR used in a method of identifying a B cell receptor.

In some embodiments, the CART cell, e.g., a T cell expressing a CAR described herein, results in greater specificity and/or activity than a control. In some embodiments, the control comprises a CAR T cell. In some embodiments, the CAR T cell has an antigen binding domain specific for an antigen unrelated to cancer. In some embodiments, the CAR T cell has an antigen binding domain specific for a cancer-specific antigen, as is described herein.

In some embodiments, activity and specificity can be demonstrated by cytotoxicity. In some embodiments, activity comprises cytotoxicity, e.g., as measured by % lysis, towards cells expressing the unique B cell receptor relative to a control. In some embodiments, the % lysis is 0.1%, 1%, 2%, 3%, 4%, 5%, 6%, 7%, 8%, 9%, 10%, 15%, 20%, or more greater than a control.

In some embodiments, specificity comprises cytotoxicity, e.g., as measured by % lysis, towards cells that do not express the unique B cell receptor. In some embodiments, the % lysis is 0.1%, 1%, 2%, 3%, 4%, 5%, 6%, 7%, 8%, 9%, 10%, 15%, 20%, or more less than a control. In some embodiments, % lysis is measured at an effector:target ratio of 1:1, 2:1, 3:1, 4:1, 5:1, 6:1, 7:1, 8:1, 9:1, 10:1, or greater.

In some embodiments, subjects treated with the CART cell, e.g., a T cell expressing a CAR described herein, exhibit reduced cytokine release syndrome (CRS) relative to a subject treated with a control.

As used herein, "coupled" refers to the association of two molecules though covalently and non-covalent interactions, e.g., by hydrogen, ionic, or Van-der-Waals bonds. Such bonds may be formed between at least two of the same or different atoms or ions as a result of redistribution of electron densities of those atoms or ions. For example, a B cell ligand may be coupled to a therapeutic agent as a fusion protein.

In some embodiments, a therapeutic agent comprises a radioactive isotope such as an α-, β-, or γ-emitter, or a β- and γ-emitter.

In some embodiments, a therapeutic agent comprises a chemotherapy. Chemotherapeutic agents include, for example, including alkylating agents, anthracyclines, cytoskeletal disruptors (Taxanes), epothilones, histone deacetylase inhibitors, inhibitors of topoisomerase I, inhibitors of topoisomerase II, kinase inhibitors, nucleotide analogs and precursor analogs, peptide antibiotics, platinum-based agents, retinoids, vinca alkaloids and derivatives thereof. Non-limiting examples include: (i) anti-angiogenic agents (e.g., TNP-470, platelet factor 4, thrombospondin-1, tissue inhibitors of metalloproteases (TIMP1 and TIMP2), prolactin (16-Kd fragment), angiostatin (38-Kd fragment of plasminogen), endostatin, bFGF soluble receptor, transforming growth factor beta, interferon alpha, soluble KDR and FLT-1 receptors, placental proliferin-related protein, as well as those listed by Carmeliet and Jain (2000)); (ii) a VEGF antagonist or a VEGF receptor antagonist such as anti-VEGF antibodies, VEGF variants, soluble VEGF receptor fragments, aptamers capable of blocking VEGF or VEGFR, neutralizing anti-VEGFR antibodies, inhibitors of VEGFR tyrosine kinases and any combinations thereof; and (iii) chemotherapeutic compounds such as, e.g., pyrimidine analogs (5-fluorouracil, floxuridine, capecitabine, gemcitabine and cytarabine), purine analogs, folate antagonists and related inhibitors (mercaptopurine, thioguanine, pentostatin and 2-chlorodeoxyadenosine (cladribine)); antiproliferative/ antimitotic agents including natural products such as vinca alkaloids (vinblastine, vincristine, and vinorelbine), microtubule disruptors such as taxane (paclitaxel, docetaxel), vincristine, vinblastine, nocodazole, epothilones, and navelbine, epidipodophyllotoxins (etoposide and teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethyhnelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycin, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenesdacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (e.g., TNP-470, genistein, bevacizumab) and growth factor inhibitors (e.g., fibroblast growth factor (FGF) inhibitors); angiotensin receptor blocker; nitric oxide donors; anti-sense oligonucleotides; antibodies (trastuzumab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, mitoxantrone, topotecan, and irinotecan), corticosteroids (cortisone, dexamethasone, hydrocortisone, methylprednisolone, prednisone, and prednisolone); growth factor signal transduction kinase inhibitors; mitochondrial dysfunction inducers and caspase activators; and chromatin disruptors.

In some embodiments, a therapeutic agent comprises an immunotherapy. Cancer immunotherapy is the use of the immune system to reject cancer. The main premise is stimulating the subject's immune system to attack the tumor cells that are responsible for the disease. This can be either through immunization of the subject, in which case the subject's own immune system is rendered to recognize tumor cells as targets to be destroyed, or through the administration of therapeutics, such as antibodies, as drugs, in which case the subject's immune system is recruited to destroy tumor cells by the therapeutic agents. Cancer immunotherapy includes an antibody-based therapy and cytokine-based therapy.

A number of therapeutic monoclonal antibodies have been approved by the FDA for use in humans, and more are underway. The FDA-approved monoclonal antibodies for cancer immunotherapy include antibodies against CD52, CD33, CD20, ErbB2, vascular endothelial growth factor and epidermal growth factor receptor. Examples of monoclonal antibodies approved by the FDA for cancer therapy include, without limitation: Rituximab (available as Rituxan™), Trastuzumab (available as Herceptin™), Alemtuzumab (available as Campath-IH™) Cetuximab (available as Erbitux™), Bevacizumab (available as Avastin™) Panitumumab (available as Vectibix™), Gemtuzumab ozogamicin (available as Mylotarg™) Ibritumomab tiuxetan (available as Zevalin™), Tositumomab (available as Bexxar™) Ipilimumab (available as Yervoy™), Ofatunumab (available as Arzerra™), Daclizumab (available as Zinbryta™), Nivolumab (available as Opdivo™), and Pembrolizumab (available as Keytruda™). Examples of monoclonal antibodies currently undergoing human clinical testing for cancer therapy in the United States include, without limitation: WX-G250 (available as Rencarex™), Zanolimumab (available as HuMax-CD4), ch14.18, Zalutumumab (available as HuMax-EGFr), Oregovomab (available as B43.13, OvalRex™), Edrecolomab (available as IGN-101, Panorex™), 131I-chTNT-I/B (available as Cotara™), Pemtumomab (available as R-1549, Theragyn™), Lintuzumab (available as SGN-33), Labetuzumab (available as hMN14, CEAcide™), Catumaxomab (available as Removab™), CNTO 328 (available as cCLB8), 3F8, 177Lu-J591, Nimotuzumab, SGN-30, Ticilimumab (available as CP-675206), Epratuzumab (available as hLL2, LymphoCide™), 90Y-Epratuzumab, Galiximab (available as IDEC-114), MDX-060, CT-011, CS-1008, SGN-40, Mapatumumab (available as TRM-I), Apolizumab (available as HuID10, Remitogen™) and Volociximab (available as M200).

Cancer immunotherapy also includes a cytokine-based therapy. The cytokine-based cancer therapy utilizes one or more cytokines that modulate a subject's immune response. Non-limiting examples of cytokines useful in cancer treatment include interferon-α (IFN-α), interleukin-2 (IL-2), Granulocyte-macrophage colony-stimulating factor (GM-CSF) and interleukin-12 (IL-12).

The B cell receptor ligand coupled to therapeutic agents, as well as encoding nucleic acids or nucleic acid sets, vectors comprising such, or host cells comprising the vectors, described herein are useful for treating cancer, including B cell malignancies, e.g. B cell lymphomas.

In some embodiments, more than one B cell receptor ligand coupled to a therapeutic agent, or a combination of a B cell receptor ligand coupled to a therapeutic agent and another suitable therapeutic agent, may be administered to a subject in need of the treatment. The B cell receptor ligand coupled to a therapeutic agent can also be used in conjunction with other agents that serve to enhance and/or complement the effectiveness of the agents.

Also contemplated herein are methods of treatment comprises concomitantly administering CAR-expressing T-cells, wherein the CAR comprises an antigen binding domain that specifically binds a cancer-specific antigen in a cancer-specific manner; and a vaccine comprising a polypeptide or a nucleic acid expressing the cancer-specific antigen, or a cancer-specific fragment thereof. In some embodiments, the cancer-specific antigen comprises a B cell receptor and the antigen binding domain comprises a B cell receptor ligand described herein. In some embodiments, the antigen binding domain comprises a B cell receptor ligand described herein identified by the methods described herein.

The terms "cancer-specific antigen" or "tumor antigen" interchangeably refers to a molecule (typically a protein, carbohydrate or lipid) that is expressed on the surface of a cancer cell, either entirely or as a fragment (e.g., MHC/peptide), and which is useful for the preferential targeting of a pharmacological agent to the cancer cell. In some embodiments, the cancer-specific antigen comprises a B cell receptor and the antigen binding domain comprises a B cell receptor ligand described herein. In some embodiments, the antigen binding domain comprises a B cell receptor ligand described herein identified by the methods described herein. In some embodiments, a tumor antigen is a marker expressed by both normal cells and cancer cells, e.g., a lineage marker, e.g., CD19 on B cells. In some embodiments, a tumor antigen is a cell surface molecule that is overexpressed in a cancer cell in comparison to a normal cell, for instance, 1-fold over expression, 2-fold overexpression, 3-fold overexpression or more in comparison to a normal cell. In some embodiments, a tumor antigen comprises a somatic mutation, e.g., is a cell surface molecule that is inappropriately synthesized in the cancer cell, for instance, a molecule that contains deletions, additions or mutations in comparison to the molecule expressed on a normal cell. In some embodiments, a cancer-specific antigen comprises a point mutation, a splice-site mutation, a frameshift mutation, a read-through mutation, or a gene-fusion mutation. In some embodiments, a cancer-specific antigen comprises a mutation in EGFRvIII, PSCA, BCMA, CD30, CEA, CD22, L1CAM, ROR1, ErbB, CD123, IL13Rα2, Mesothelin, FRα, VEGFR, c-Met, 5T4, CD44v6, B7-H4, CD133, CD138, CD33, CD28, GPC3, EphA2, CD19, ACVR2B, anaplastic lymphoma kinase (ALK), MYCN, BCR, HER2, NY-ESO1, MUC1, or MUC16. In some embodiments, a tumor antigen will be expressed exclusively on the cell surface of a cancer cell, entirely or as a fragment (e.g., MHC/peptide), and not synthesized or expressed on the surface of a normal cell.

In some embodiments, the cancer-specific antigen binds a cancer-specific antigen in a cancer-specific manner. In some embodiments, when a the cancer-specific antigen binds a cancer-specific antigen in a cancer-specific manner, the cancer-specific antigen binds cancerous cells with 1.1×, 1.5×, 2×, 3×, 4×, 5×, 6×, 7×, 8×, 9×, 10×, 20×, 30×, 40×, 50×, 60×, 70×, 80×, 90×, 100×, 200×, 300×, 400×, 500×, 600×, 700×, 800×, 900×, 1,000× or more affinity than non-cancerous cells.

In some embodiments, the methods described herein comprise identifying the cancer-specific antigen in a subject. In some embodiments, identifying the cancer-specific antigen comprises obtaining cancerous cells from a subject. In some embodiments, the cancerous cells are obtained from a biopsy. In some embodiments, the cancerous cells are in the blood of the subject.

In some embodiments, DNA from the cancerous cells is extracted and sequenced. In some embodiments, the sequence of the DNA, or of one or more genes is compared to the same sequence in non-cancerous cells.

In some embodiments, RNA from the cancerous cells is extracted and cDNA is synthesized. In some embodiments, the cDNA is sequenced. In some embodiments, the sequence of the cDNA, or of one or more genes is compared to the same sequence in non-cancerous cells.

In some embodiments, identifying the cancer-specific antigen comprises isolating and sequencing circulating cell free DNA of the subject.

"Concomitantly" means administering two or more substances to a subject in a manner that is correlated in time, preferably sufficiently correlated in time so as to provide a modulation in an immune response. In embodiments, concomitant administration may occur through administration of two or more substances in the same dosage form. In other embodiments, concomitant administration may encompass administration of two or more substances in different dosage forms, but within a specified period of time, preferably within 1 month, more preferably within 1 week, still more preferably within 1 day, and even more preferably within 1 hour. The use of the term "concomitantly" does not restrict the order in which the therapeutic agents are administered to a subject. A first therapeutic agent, such as a CAR-T cell, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), simultaneously with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent, such as a vaccine described herein, to a subject. Thus, a first agent can be administered separately, sequentially or simultaneously with the second therapeutic agent. In some embodiments, the concomitant administration occurs at least two times, at least three times, at least four times, at least five times, at least six times, at least seven times, at least eight times, at least nine times, or at least ten times in the subject.

In some embodiments, the CAR-expressing T cells are administered before the vaccine. In some embodiments, the CAR-expressing T cells are administered after the vaccine.

To practice the method disclosed herein, an effective amount of the B cell receptor ligand coupled to a therapeutic agent, the CARs, and the vaccines described herein can be administered to a subject (e.g., a human) in need of the treatment via a suitable route, such as intravenous administration, e.g., as a bolus or by continuous infusion over a period of time, by intramuscular, intraperitoneal, intracerebrospinal, subcutaneous, intra-articular, intrasynovial, intrathecal, oral, inhalation or topical routes. In some embodiments, vaccines described herein are administered intratumorally. In some embodiments, CAR T-cells described herein are administered intraveneously. Commercially available nebulizers for liquid formulations, including jet nebulizers and ultrasonic nebulizers are useful for administration. Liquid formulations can be directly nebulized and lyophilized powder can be nebulized after reconstitution. Alternatively, the B cell receptor ligand coupled to a therapeutic agent, the CARs, and the vaccines as described herein can be aerosolized using a fluorocarbon formulation and a metered dose inhaler, or inhaled as a lyophilized and milled powder.

The subject to be treated by the methods described herein can be a mammal, more preferably a human. Mammals include, but are not limited to, farm animals, sport animals, pets, primates, horses, dogs, cats, mice and rats. A human subject who needs the treatment may be a human patient having, at risk for, or suspected of having a target disease/disorder, such as cancer. A subject having a target disease or disorder can be identified by routine medical examination, e.g., laboratory tests, organ functional tests, CT scans, or ultrasounds. A subject suspected of having any of such target disease/disorder might show one or more symptoms of the disease/disorder. A subject at risk for the disease/disorder can be a subject having one or more of the risk factors for that disease/disorder.

The methods and compositions described herein may be used to treat any disease or disorder associated with cancer. In some embodiments, the cancer is a B cell malignancy. In some embodiments, the cancer is a lymphoma. In some embodiments, the cancer is selected from diffuse large B-cell lymphoma (DLBCL), follicular lymphoma, marginal zone B-cell lymphoma (MZL) or mucosa-associated lymphatic tissue lymphoma (MALT), chronic lymphocytic leukemia (CLL), mantle cell lymphoma (MCL), Burkitt's lymphoma, lymphoplasmacytic lymphoma, nodal marginal zone B cell lymphoma (NMZL), splenic marginal zone lymphoma (SMZL), intravascular large B-cell lymphoma, primary effusion lymphoma, lymphomatoid granulomatosis, primary central nervous system lymphoma, ALK-positive large B-cell lymphoma, plasmablastic lymphoma, large B-cell lymphoma arising in HHV8-associated multicentric Castleman's disease, and B-cell lymphoma.

Other cancers include but are not limited to: Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: non-small cell lung cancer (NSCLC), small cell lung cancer, bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), rectal, colon, colon-rectum, colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), head and neck cancer, meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sefton-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, multiple endocrine neoplasia type 2A, multiple endocrine neoplasia type 2B, familial medullary thyroid cancer, pheochromocytoma, paraganglioma; and Adrenal glands: neuroblastoma.

As used herein, "an effective amount" refers to the amount of each active agent required to confer therapeutic effect on the subject, either alone or in combination with one or more other active agents. In some embodiments, the therapeutic effect is reduction in progression of cancer. Determination of whether an amount of the B cell receptor ligand coupled to a therapeutic agent described herein, or the CARs and the vaccines described herein achieved the therapeutic effect would be evident to one of skill in the art. Effective amounts vary, as recognized by those skilled in the art, depending on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment.

Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of a target disease/disorder.

In one example, dosages may be determined empirically in individuals who have been given one or more administration(s) of the molecule. Individuals are given incremental dosages of the molecule. To assess efficacy of the B cell receptor ligand coupled to a therapeutic agent, or the CARs and the vaccines an indicator of the disease/disorder can be followed.

For the purpose of the present disclosure, the appropriate dosage will depend on the type and severity of the disease/disorder, whether the B cell receptor ligand coupled to a therapeutic agent or the CARs and the vaccines described herein is administered for preventive or therapeutic purposes, previous therapy, the patient's clinical history and response to the B cell receptor ligand coupled to a therapeutic agent or the CARs and the vaccines, and the discretion of the attending physician. Typically the clinician will administer the B cell receptor ligand coupled to a therapeutic agent or the CARs and the vaccines, until a dosage is reached that achieves the desired result. In some embodiments, the desired result is a decrease the severity of cancer. Methods of determining whether a dosage resulted in the desired result would be evident to one of skill in the art. Administration of one or more B cell receptor ligands coupled to a therapeutic agents or the CARs and the vaccines can be continuous or intermittent, depending, for example, upon the recipient's physiological condition, whether the purpose of the administration is therapeutic or prophylactic, and other factors known to skilled practitioners. The administration of a B cell receptor ligand coupled to a therapeutic agent or the CARs and the vaccines may be essentially continuous over a preselected period of time or may be in a series of spaced dose, e.g., either before, during, or after developing a target disease or disorder.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

The B cell receptor ligand coupled to a therapeutic agent or the CARs and the vaccines described herein can be administered via conventional routes, e.g., administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In addition, it can be administered to the subject via injectable depot routes of administration such as using 1-, 3-, or 6-month depot injectable or biodegradable materials and methods. In some examples, the pharmaceutical composition is administered intraocularly or intravitreally.

In one embodiment, the B cell receptor ligand coupled to a therapeutic agent or the CARs and the vaccines described herein is administered via site-specific or targeted local delivery techniques. Examples of site-specific or targeted local delivery techniques include various implantable depot sources of the antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Targeted delivery of therapeutic compositions containing an antisense polynucleotide, expression vector, or subgenomic polynucleotides can also be used. Receptor-mediated DNA delivery techniques are described in, for example, Findeis et al., Trends Biotechnol. (1993) 11:202; Chiou et al., Gene Therapeutics: Methods And Applications Of Direct Gene Transfer (J. A. Wolff, ed.) (1994); Wu et al., J. Biol. Chem. (1988) 263:621; Wu et al., J. Biol. Chem. (1994) 269:542; Zenke et al., Proc. Natl. Acad. Sci. USA (1990) 87:3655; Wu et al., J. Biol. Chem. (1991) 266:338.

The therapeutic polynucleotides and polypeptides described herein can be delivered using gene delivery vehicles. The gene delivery vehicle can be of viral or non-viral origin (see generally, Jolly, Cancer Gene Therapy (1994) 1:51; Kimura, Human Gene Therapy (1994) 5:845; Connelly, Human Gene Therapy (1995) 1:185; and Kaplitt, Nature Genetics (1994) 6:148). Expression of such coding sequences can be induced using endogenous mammalian or heterologous promoters and/or enhancers. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther. (1992) 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther. (1992) 3:147); ligand-linked DNA (see, e.g., Wu, J. Biol. Chem. (1989) 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0524968. Additional approaches are described in Philip, Mol. Cell. Biol. (1994) 14:2411, and in Woffendin, Proc. Natl. Acad. Sci. (1994) 91:1581.

The particular dosage regimen, i.e., dose, timing and repetition, used in the method described herein will depend on the particular subject and that subject's medical history.

Treatment efficacy for a target disease/disorder can be assessed by methods well-known in the art.

As used herein, the term "in combination" refers to the use of more than one therapeutic agent. The use of the term "in combination" does not restrict the order in which the therapeutic agents are administered to a subject. A first therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent. Thus, a first agent can be administered separately, sequentially or simultaneously with the second therapeutic agent.

In some embodiments, a CAR-T cell and a vaccine described herein are administered in combination with a TLR9 agonist. In some embodiments, the TLR9 agonist is a CpG oligonucleotide.

Vaccines

In some embodiments, CAR-expressing T-cells described herein are administered with a vaccine. In some embodiments, the vaccine comprises a polypeptide or a nucleic acid expressing a cancer-specific antigen, or a cancer-specific fragment thereof, as is described supra.

In some embodiments, the vaccine comprises a cancer-specific fragment of a cancer-specific antigen.

In some embodiments, the cancer-specific fragment of the cancer specific antigen is 1-1000 amino acids long, or 10-500 amino acids long. In some embodiments, the cancer-specific fragment of the cancer specific antigen is 10, 20, 30, 40, 50, 60, 70, 80, 90, 100, 200, 300, 400, or 500 or more amino acids long.

In some embodiments, the cancer-specific antigen, or a cancer-specific fragment thereof comprises a somatic mutation as is described supra, e.g., comprises a point mutation, a splice-site mutation, a frameshift mutation, a read-through mutation, or a gene-fusion mutation, and the polypeptide or nucleic acid expressing the cancer-specific antigen, or cancer-specific fragment thereof comprises the somatic mutation.

Peptide Vaccines

In some embodiments, the vaccine comprises a polypeptide expressing a cancer-specific antigen, or a cancer-specific fragment thereof.

In particular embodiments, the DNA that encodes for the protein vaccine can be introduced into an expression vector, such as a plasmid. Multiple cloning sites, which contain DNA sequences that are recognized by restriction enzymes, can facilitate the insertion of the protein vaccine DNA into the vector. In particular embodiments, DNA constructs (such as expression vectors) that encode the proteins of interest can be introduced into cells to induce protein expression and the cells can be harvested to extract the protein of interest. The DNA encoding the protein of interest can be included in an expression vector that also contains sequences that control gene expression, such as promoter sequences. 5' and 3' untranslated regions can be encoded upstream and downstream of the protein coding sequence in order to enhance expression. For example, a 5' untranslated leader sequence and a 3' polyadenylation sequence can be used. In particular embodiments, the DNA can be introduced into cells for protein expression by heat-shock transformation. In particular embodiments, DNA can be introduced into cells for protein expression by transfection, electroporation, impalefection or hydrodynamic delivery. In particular embodiments, the DNA used for protein expression can be delivered in the form of a viral vector. In particular embodiments, the protein of interest can be harvested from lysed cells, and purified. Protein purification can be performed using size-exclusion chromatography, or by a chromatography technique that isolates the protein based on a protein-tag, such as a 6× histidine tag or a c-myc tag. The histidine tag can be encoded adjacent to a sequence recognized and cleaved by a protease, to facilitate removal of the histidine tag after protein purification. An example of a protease that can be used to remove a histidine tag from a protein is the human rhinovirus 3C protease.

In some embodiments, the vaccine comprises two or more polypeptides having overlapping sequences, each expressing a fragment of the cancer-specific antigen.

In some embodiments, the polypeptide is conjugated to a carrier protein, e.g., OVA, KLH, or BSA.

DNA Vaccines

In some embodiments, the vaccine comprises a nucleic acid expressing a cancer-specific antigen, or a cancer-specific fragment thereof.

In some embodiments, the nucleic acid is DNA. A DNA vaccine may comprise an "expression vector" or "expression cassette," i.e., a nucleotide sequence which is capable of affecting expression of a protein coding sequence in a host compatible with such sequences. Expression cassettes include at least a promoter operably linked with the polypeptide coding sequence; and, optionally, with other sequences, e.g., transcription termination signals. Additional factors necessary or helpful in effecting expression may also be included, e.g., enhancers.

"Operably linked" means that the coding sequence is linked to a regulatory sequence in a manner that allows expression of the coding sequence. Known regulatory sequences are selected to direct expression of the desired protein in an appropriate host cell. Accordingly, the term "regulatory sequence" includes promoters, enhancers and other expression control elements. Such regulatory sequences are described in, for example, Goeddel, *Gene Expression Technology. Methods in Enzymology*, vol. 185, Academic Press, San Diego, Calif. (1990)).

A promoter region of a DNA or RNA molecule binds RNA polymerase and promotes the transcription of an "operably linked" nucleic acid sequence. As used herein, a "promoter sequence" is the nucleotide sequence of the promoter which is found on that strand of the DNA or RNA which is transcribed by the RNA polymerase. Two sequences of a nucleic acid molecule, such as a promoter and a coding sequence, are "operably linked" when they are linked to each other in a manner Which permits both sequences to be transcribed onto the same RNA transcript or permits an RNA transcript begun in one sequence to be extended into the second sequence. Thus, two sequences, such as a promoter sequence and a coding sequence of DNA or RNA are operably linked if transcription commencing in the promoter sequence will produce an RNA transcript of the operably linked coding sequence. In order to be "operably linked" it is not necessary that two sequences be immediately adjacent to one another in the linear sequence.

The preferred promoter sequences of the present invention must be operable in mammalian cells and may be either eukaryotic or viral promoters. Suitable promoters may be inducible, repressible or constitutive. A "constitutive" promoter is one which is active under most conditions encountered in the cell's environmental and throughout development. An "inducible" promoter is one which is under environmental or developmental regulation. A "tissue specific" promoter is active in certain tissue types of an organism. An example of a constitutive promoter is the viral promoter MSV-LTR, which is efficient and active in a variety of cell types, and, in contrast to most other promoters, has the same enhancing activity in arrested and growling cells. Other preferred viral promoters include that present in the CMV-LTR (from cytomegalovirus) (Bashart, M. et al., Cell 41:521, 1985) or in the RSV-LTR (from Rous sarcoma virus) (Gorman, C. M., Proc. Natl. Acad. Sci. USA 79:6777, 1982). Also useful are the promoter of the mouse metallothionein I gene (Hamer, D, et al., J. Mol. Appl. Gen. 1:273-88, 1982; the TK promoter of Herpes virus (McKnight, S. Cell 31:355-65, 1982); the SV40 early promoter (Benoist, C., et al., Nature 290:304-10, 1981); and the yeast gal4 gene promoter (Johnston, S A et al., Proc. Natl. Acad. Sci. USA 79:6971-5, 1982); Silver, P A, et al., Proc. Natl. Acad. Sci. (USA) 81:5951-5, 1984)). Other illustrative descriptions of transcriptional factor association with promoter regions and the separate activation and DNA binding of transcription factors include: Keegan et al., Nature 231:699, 1986; Fields et al., Nature 340:245, 1989; Jones; Cell 61:9, 1990; Lewin, Cell 61:1161, 1990; Ptashne et al., Nature 346:329, 1990; Adams et al., Cell 72:306, 1993.

The promoter region may further include an octamer region which may also function as a tissue specific enhancer, by interacting with certain proteins found in the specific tissue. The enhancer domain of the DNA construct of the present invention is one which is specific for the target cells to be transfected, or is highly activated by cellular factors of such target cells. Examples of vectors (plasmid or retrovirus) are disclosed, e.g., in Roy-Burman et al.; U.S. Pat. No. 5,112,767. For a general discussion of enhancers and their actions in transcription, see. Lewin, B M, Genes IV, Oxford University Press pp. 552-576, 1990 (or later edition). Particularly, useful are retroviral enhancers (e.g., viral LTR) that is preferably placed upstream from the promoter with which it interacts to stimulate gene expression. For use with retroviral vectors, the endogenous viral LTR may be rendered enhancer-less and substituted with other desired enhancer sequences which confer tissue specificity or other desirable properties such as transcriptional efficiency.

Thus, expression cassettes include plasmids, recombinant viruses, any form of a recombinant "naked DNA" vector, and the like. A "vector" comprises a nucleic acid which can infect, transfect, transiently or permanently transduce a cell. It will be recognized that a vector can be a naked nucleic acid, or a nucleic acid complexed with protein or lipid. The vector optionally comprises viral or bacterial nucleic acids and/or proteins, and/or membranes (e.g., a cell membrane, a viral lipid envelope, etc.). Vectors include replicons RNA replicons), bacteriophages) to which fragments of DNA may be attached and become replicated. Vectors thus include, but are not limited to RNA, autonomous self-replicating circular or linear DNA or RNA, e.g., plasmids, viruses, and the like (U.S. Pat. No. 5,217,879), and includes both the expression and nonexpression plasmids. Where a recombinant cell or culture is described as hosting an "expression vector" this includes both extrachromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

Exemplary virus vectors that may be used include recombinant adenoviruses (Horowitz, M S, In: Virology, Fields, B N et al., eds, Raven Press, N Y, 1990, p. 1679; Berkner, K Biotechniques 6:616-29, 1988; Strauss, S E, In: The Adenoviruses, Ginsberg, H S, ed., Plenum Press, N Y, 1984, chapter 11) and herpes simplex virus (HSV). Advantages of adenovirus vectors for human gene delivery include the fact that recombination is rare, no human malignancies are known to be associated with such viruses, the adenovirus genome is double stranded DNA which can be manipulated to accept foreign genes of up to 7.5 kb in size, and live adenovirus is a safe human vaccine organisms. Adeno-associated virus is also useful for human therapy (Samulski, R J et al., EMBO J. 10:3941, 1991) according to the present invention.

Another vector which can express the DNA molecule of the present invention, and is useful in the present therapeutic setting is vaccinia virus, which can be rendered non-replicating (U.S. Pat. Nos. 5,225,336; 5,204,243; 5,155,020; 4,769,330; Fuerst, T R et al., Proc. Natl. Acad. Sci. USA 86:2549-53, 1992; Chakrabarti, S et at, Mol Cell Biol 5:3403-9, 1985). Descriptions of recombinant vaccinia viruses and other viruses containing heterologous DNA and their uses in immunization and DNA therapy are reviewed in: Moss, B, CurrT Opin Genet Dev 3:86-90, 1993; Moss, B, Biotechnol. 20:345-62, 1992).

Other viral vectors that may be used include viral or non-viral vectors, including adeno-associated virus vectors; retrovirus vectors, lentivirus vectors, and plasmid vectors. Exemplary types of viruses include HSV (herpes simplex virus), AAV (adeno associated virus), HIV (human immunodeficiency virus), BIV (bovine immunodeficiency virus), and MLV (murine leukemia virus).

A DNA vaccine may also use a replicon, e.g., an RNA replicon, a self-replicating RNA vector. Generally, RNA replicon vaccines may be derived from alphavirus vectors, such as Sindbis virus (Hariharan, M J et al., 1998. J Virol 72:950-8.), Semliki Forest virus (Berglund, P M et al., 1997. AIDS Res Hum Retroviruses 13:1487-95; Ying, H T et al., 1999. Nat Med 5:823-7) or Venezuelan equine encephalitis virus (Pushko, P M et al., 1997. Virology 239:389-401). These self-replicating and self-limiting vaccines may be administered as either (1) RNA or (2) DNA which is then transcribed into RNA replicons in cells transfected in vitro or in vivo (Berglund, P C et al., 1998. Nat Biotechnol 16:562-5; Leitner, W W et al.; 2000. Cancer Res 60:51-5). An exemplary Semliki Forest virus is pSCA1 (DiCiommo, D P et al., J Biol Chem 1998; 273:18060-6).

In addition to naked DNA or viral vectors, engineered bacteria may be used as vectors. A number of bacterial strains including Salmonella, BCG and Listeria monocytogenes (LM) (Hoiseth et al., Nature 291:238-9, 1981; Poirier, T P et al., J Exp Med 168:25-32; 1988); Sadoff, J C et al., Science 240:336-8, 1988; Stover, C K et al., Nature 351:456-60, 1991; Aldovini A et al., Nature 351:479-82, 1991). These organisms display two promising characteristics for use as vaccine vectors: (1) enteric routes of infection, providing the possibility of oral vaccine delivery; and (2) infection of monocytes/macrophages thereby targeting antigens to professional APCs.

In addition to virus-mediated gene transfer in vivo, physical means well-known in the art can be used for direct transfer of DNA, including administration of plasmid DNA (Wolff et al.; 1990, supra) and particle-bombardment mediated gene transfer (Yang, N-S, et al., Proc Natl Acad Sci USA 87:9568, 1990; Williams, R S et al., Proc Natl Acad Sci USA 88:2726, 1991; Zelenin, A V et al., FEBS Lett 280:94, 1991; Zelenin, A V et al., FEBS Lett 244:65, 1989); Johnston, S A et al., In Vitro Dev Biol 27:11, 1991). Furthermore, electroporation, a well-known means to transfer genes into cell in vitro, can be used to transfer DNA molecules according to the present invention to tissues in vivo (Titomirov, A V et al., Biochim Biophys Acta 1088:131, 1991).

"Carrier mediated gene transfer" has also been described (Wu, C H et al., J Biol Chem 264:16985, 1989; Wu, G Y et al., *J Biol Chem* 263:14621; 1988; Soriano, P et al., *Proc Nat. Acad Sci USA* 80:7128, 1983; Wang, C-Y et al., *Pro. Natl Acad Sci USA* 84:7851, 1982; Wilson, M et al., *J Biol Chem* 267:963, 1992). Preferred carriers are targeted liposomes (Nicolau, C et al., *Proc Natl Acad Sci USA* 80:1068, 1983; Soriano et al., supra) such as immunoliposomes, which can incorporate acylated mAbs into the lipid bilayer (Wang et at, supra). Polycations such as asialoglycoprotein/polylysine (Wu et al., 1989, supra) may be used, where the conjugate includes a target tissue-recognizing molecule (e.g., asialo-orosomucoid for liver) and a DNA binding compound to bind to the DNA to be transfected without causing damage, such as polylysine. This conjugate is then complexed with plasmid DNA of the present invention.

Plasmid DNA used for transfection or microinjection may be prepared using methods well-known in the art, for example using the Qiagen procedure (Qiagen), followed by DNA purification using known methods, such as the methods exemplified herein.

Such expression vectors may be used to transfect host cells (in vitro, ex vivo or in vivo) for expression of the DNA and production of the encoded proteins which include fusion proteins or peptides. In one embodiment, a DNA vaccine is administered to or contacted with a cell, e.g., a cell obtained from a subject (e.g., an antigen presenting cell), and administered to a subject, wherein the subject is treated before, after or at the same time as the cells are administered to the subject.

RNA Vaccines

In some embodiments, the vaccine comprises a nucleic acid expressing a cancer-specific antigen, or a cancer-specific fragment thereof, and the nucleic acid is RNA.

RNA vaccines, as provided herein, comprise at least one (one or more) ribonucleic acid (RNA) polynucleotide having an open reading frame encoding at least one cancer-specific antigen, or a cancer-specific fragment thereof. The term "nucleic acid," in its broadest sense, includes any compound and/or substance that comprises a polymer of nucleotides. These polymers are referred to as polynucleotides.

In some embodiments, polynucleotides of the present disclosure function as messenger RNA (mRNA). "Messenger RNA" (mRNA) refers to any polynucleotide that encodes a (at least one) polypeptide (a naturally-occurring, non naturally-occurring, or modified polymer of amino acids) and can be translated to produce the encoded polypeptide in vitro in vivo, in situ or ex vivo.

The basic components of an mRNA molecule typically include at least one coding region, a 5' untranslated region (UTR), a 3' UTR, a 5' cap and a poly-A tail. Polynucleotides of the present disclosure may function as mRNA but can be distinguished from wild type mRNA in their functional and/or structural design features which serve to overcome existing problems of effective polypeptide expression using nucleic-acid based therapeutics.

RNA (e.g., mRNA) vaccines of the present disclosure comprise, in some embodiments, at least one ribonucleic acid (RNA) polynucleotide having an open reading frame encoding at least one cancer-specific antigen, or a cancer-specific fragment thereof, wherein said RNA comprises at least one chemical modification.

Polynucleotides (e.g., RNA polynucleotides, such as mRNA polynucleotides), in some embodiments, comprise various (more than one) different modifications. In some embodiments, a particular region of a polynucleotide contains one, two or more (optionally different) nucleoside or nucleotide modifications. In some embodiments, a modified RNA polynucleotide (e.g., a modified mRNA polynucleotide), introduced to a cell or organism, exhibits reduced degradation in the cell or organism, respectively, relative to an unmodified polynucleotide. In some embodiments, a modified RNA polynucleotide (e.g., a modified mRNA polynucleotide), introduced into a cell or organism, may exhibit reduced immunogenicity in the cell or organism, respectively (e.g., a reduced innate response).

Polynucleotides (e.g., RNA polynucleotides, such as mRNA polynucleotides), in some embodiments, comprise non-natural modified nucleotides that are introduced during synthesis or post-synthesis of the polynucleotides to achieve desired functions or properties. The modifications may be present on an internucleotide linkages, purine or pyrimidine bases, or sugars. The modification may be introduced with chemical synthesis or with a polymerase enzyme at the terminal of a chain or anywhere else in the chain. Any of the regions of a polynucleotide may be chemically modified.

The present disclosure provides for modified nucleosides and nucleotides of a polynucleotide (e.g., RNA polynucleotides, such as mRNA polynucleotides). A "nucleoside" refers to a compound containing a sugar molecule (e.g., a pentose or ribose) or a derivative thereof in combination with an organic base (e.g., a purine or pyrimidine) or a derivative thereof (also referred to herein as "nucleobase"). A nucleotide" refers to a nucleoside, including a phosphate group. Modified nucleotides may by synthesized by any useful method, such as, for example, chemically, enzymatically, or recombinantly, to include one or more modified or non-natural nucleosides. Polynucleotides may comprise a region or regions of linked nucleosides. Such regions may have variable backbone linkages. The linkages may be standard phosphdioester linkages, in which case the polynucleotides would comprise regions of nucleotides.

Cancer vaccines of the present disclosure comprise at least one RNA polynucleotide, such as a mRNA (e.g., modified mRNA). mRNA, for example, is transcribed in vitro from template DNA, referred to as an "in vitro transcription template." In some embodiments, an in vitro transcription template encodes a 5' untranslated (UTR) region, contains an open reading frame, and encodes a 3' UTR and a polyA tail. The particular nucleic acid sequence composition and length of an in vitro transcription template will depend on the mRNA encoded by the template.

In some embodiments, a polynucleotide includes 200 to 3,000 nucleotides. For example, a polynucleotide may include 200 to 500, 200 to 1000, 200 to 1500, 200 to 3000, 500 to 1000, 500 to 1500, 500 to 2000, 500 to 3000, 1000 to 1500, 1000 to 2000, 1000 to 3000, 1500 to 3000, or 2000 to 3000 nucleotides).

In other aspects, the invention relates to a method for preparing an mRNA cancer vaccine by IVT methods. In vitro transcription (IVT) methods permit template-directed synthesis of RNA molecules of almost any sequence. The size of the RNA molecules that can be synthesized using IVT methods range from short oligonucleotides to long nucleic acid polymers of several thousand bases. IVT methods permit synthesis of large quantities of RNA transcript (e.g., from microgram to milligram quantities) (Beckert et al., Synthesis of RNA by in vitro transcription, *Methods Mol Biol.* 703:29-41 (2011); Rio et al. RNA: A Laboratory Manual. Cold Spring Harbor: Cold Spring Harbor Laboratory Press, 2011, 205-220.; Cooper, Geoffery M. The Cell: A Molecular Approach. 4th ed. Washington D.C.: ASM Press, 2007. 262-299). Generally, IVT utilizes a DNA template featuring a promoter sequence upstream of a sequence of interest. The promoter sequence is most commonly of bacteriophage origin (ex. the T7, T3 or SP6 promoter sequence) but many other promotor sequences can be tolerated including those designed de novo. Transcription of the DNA template is typically best achieved by using the RNA polymerase corresponding to the specific bacteriophage promoter sequence. Exemplary RNA polymerases include, but are not limited to T7 RNA polymerase, T3 RNA polymerase, or SP6 RNA polymerase, among others. IVT is generally initiated at a dsDNA but can proceed on a single strand.

Vaccine Compositions

In some embodiments, the vaccine minimally includes the antigen.

To further achieve an effective vaccine according to this disclosure, materials and methods can be employed to enhance availability of the vaccine. One such method employs an adjuvant.

The term "adjuvant" refers to material that enhances the immune response to an antigen and is used herein in the customary use of the term. The precise mode of action is not understood for all adjuvants, but such lack of understanding does not prevent their clinical use for a wide variety of vaccines, whether protein-based or DNA-based. Traditionally, some adjuvants physically trap antigen at the site of injection, enhancing antigen presence at the site and slowing its release. This in turn prolongs and/or increases the recruitment and activation of APCs, such as in this case iDCs.

In particular embodiments a squalene-based adjuvant is used. Squalene is part of the group of molecules known as triterpenes, which are all hydrocarbons with 30 carbon molecules. Squalene can be derived from certain plant sources, such as rice bran, wheat germ, amaranth seeds, and olives, as well as from animal sources, such as shark liver oil. In particular embodiments, the squalene-based adjuvant is MF59®, which is an oil-in-water emulsion (Novartis, Basel, Switzerland; see Giudice, G D et al. *Clin Vaccine Immunol.* 2006 September; 13(9):1010-3). An example of a squalene-based adjuvant that is similar to MF59® but is designed for preclinical research use is Addavax™ (InvivoGen, San Diego, CA). MF59 has been FDA approved for use in an influenza vaccine, and studies indicate that it is safe for use during pregnancy (Tsai T, et al. Vaccine. 2010. 17:28 (7):1877-80; Heikkinen T, et al. Am J Obstet Gynecol. 2012. 207(3):177). In particular embodiments, squalene-based adjuvants can include 0.1%-20% (v/v) squalene oil. In particular embodiments, squalene-based adjuvants can include 5% (v/v) squalene oil. In particular embodiments, the squalene-based adjuvant is AS03, which includes α-tocopherol, squalene, and polysorbate 80 in an oil-in-water emulsion (GlaxoSmithKline; see Garcon N et al. *Expert Rev Vaccines.* 2012 March; 11(3):349-66).

In particular embodiments, polyinosinic:polycytidilyic acid (also referred to as poly(I:C) is used. Poly(I:C) is a synthetic analog of double-stranded RNA that stimulates the immune system. In particular embodiments, Poly-ICLC (Hiltinol) is used (Ammi R et al. Pharmacol Ther. 2015 February; 146:120-31). In particular embodiments, Poliu-IC12U (Ampligen) is used (Martins K A et al. *Expert Rev Vaccines.* 2015 March; 14(3):447-59).

In particular embodiments the adjuvant alum can be used. Alum refers to a family of salts that contain two sulfate groups, a monovalent cation, and a trivalent metal, such as aluminum or chromium. Alum is an FDA approved adjuvant. In particular embodiments, vaccines can include alum in the amounts of 1-1000 ug/dose or 0.1 mg-10 mg/dose.

In particular embodiments, the adjuvant Vaxfectin® (Vical, Inc., San Diego, CA) can be used. Vaxfectin® is a cationic lipid based adjuvant that can be used for DNA or protein vaccines.

Compositions for Administration. Vaccines of the disclosure can be formulated into pharmaceutical compositions for administration including a vaccine of the disclosure can be formulated in a variety of forms, e.g., as a liquid, gel, lyophilized, or as a compressed solid. The particular form will depend upon the particular indication being treated and will be apparent to one of ordinary skill in the art.

An example of a pharmaceutical composition is a solution designed for parenteral administration. Although in many cases pharmaceutical solution formulations are provided in liquid form, appropriate for immediate use, such parenteral formulations can also be provided in frozen or in lyophilized form. In the former case, the composition must be thawed prior to use. The latter form is often used to enhance the stability of the active compound contained in the composition under a wider variety of storage conditions, as it is recognized by those or ordinary skill in the art that lyophilized preparations are generally more stable than their liquid counterparts. Such lyophilized preparations are reconstituted prior to use by the addition of one or more suitable pharmaceutically acceptable diluents such as sterile water for injection or sterile physiological saline solution.

Parenterals can be prepared for storage as lyophilized formulations or aqueous solutions by mixing, as appropriate, the composition having the desired degree of purity with one or more pharmaceutically acceptable carriers, excipients or stabilizers typically employed in the art (all of which are termed "excipients"), for example buffering agents, stabilizing agents, preservatives, isotonifiers, non-ionic detergents, antioxidants and/or other miscellaneous additives.

Buffering agents help to maintain the pH in the range which approximates physiological conditions. They are typically present at a concentration ranging from 2 mM to 50 mM. Suitable buffering agents for use with the present disclosure include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium glyuconate mixture, etc.), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additional possibilities are phosphate buffers, histidine buffers and trimethylamine salts such as Tris.

Preservatives can be added to retard microbial growth, and are typically added in amounts of 0.2%-1% (w/v). Suitable exemplary preservatives for use with the present disclosure include phenol, benzyl alcohol, meta-cresol, methyl paraben, propyl paraben, octadecyldimethylbenzyl ammonium chloride, benzalkonium halides (e.g., benzalkonium chloride, bromide or iodide), hexamethonium chloride, alkyl parabens such as methyl or propyl paraben, catechol, resorcinol, cyclohexanol and 3-pentanol.

Isotonicifiers can be added to ensure isotonicity of liquid compositions and include polyhydric sugar alcohols, trihydric or higher sugar alcohols, such as glycerin, erythritol, arabitol, xylitol, sorbitol and mannitol. Polyhydric alcohols can be present in an amount between 0.1% and 25% by weight, typically 1% to 5%, taking into account the relative amounts of the other ingredients.

Stabilizers refer to a broad category of excipients which can range in function from a bulking agent to an additive which solubilizes the vaccine or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, and glycerol; polyethylene glycol; amino acid polymers; sulfur-containing reducing agents, such as urea, glutathione, thioctic acid, sodium thioglycolate, thioglycerol, alpha-monothioglycerol and sodium thiosulfate; low molecular weight polypeptides (i.e., <10 residues); proteins such as human serum albumin, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran. Stabilizers are typically present in the range of from 0.1 to 10,000 parts by weight based on the vaccine composition. Additional miscellaneous excipients include bulking agents or fillers (e.g., starch), chelating agents (e.g., EDTA), antioxidants (e.g., ascorbic acid, methionine, vitamin E) and cosolvents.

The vaccine composition can also be entrapped in microcapsules prepared, for example, by coascervation techniques or by interfacial polymerization, for example hydroxymethylcellulose, gelatin or poly-(methylmethacylate) microcapsules, in colloidal drug delivery systems (for example liposomes, albumin microspheres, microemulsions, nanoparticles and nanocapsules) or in macroemulsions. Such techniques are disclosed in Remington's Pharmaceutical Sciences.

Parenteral formulations to be used for in vivo administration generally are sterile. This is readily accomplished, for example, by filtration through sterile filtration membranes.

Suitable examples of sustained-release vaccine compositions include semi-permeable matrices of solid hydrophobic polymers containing the composition, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylene-vinyl acetate, degradable lactic acid-glycolic acid copolymers such as the PROLEASE® (Alkermes, Inc., Waltham, MA) technology or LUPRON DEPOT® (injectable microspheres composed of lactic acid-glycolic acid copolymer and leuprolide acetate; Abbott Endocrine, Inc., Abbott Park, IL), and poly-D-(–)-3-hydroxybutyric acid. While polymers such as ethylene-vinyl acetate and lactic acid-glycolic acid enable release of molecules for long periods, such as up to or over 100 days, certain hydrogels release compounds for shorter time periods.

EXAMPLES

Example 1

Reported herein is the development of a novel platform to significantly enhance the efficacy and safety of Follicular lymphoma treatment. Since lymphoma is a clonal malignancy of a diversity system, every tumor has a different antibody on its cell surface. Combinatorial autocrine-based selection is used to rapidly identify specific ligands for these B cell receptors on the surface of FL tumor cells. The selected ligands are used in a CAR-T format for redirection of human CTLs. Essentially, the format is the inverse of the usual CAR-T protocol. Instead of being a guide molecule, the antibody itself is the target. Thus, these studies raise the possibility of personalized treatment of lymphomas utilizing a private antibody binding ligand that can be obtained in few weeks.

Although a special case, the B cell receptor (BCR) on lymphoma cells is the purest form of a tumor specific antigen (1). This is because lymphoma is a tumor of one member of a diversity system were each tumor expresses only one of $10^8$ different antibody molecules (2). Thus, it's remarkable that antigens selective for BCR's binding have not been more generally used for therapy (3, 4). Probably, the reason is that the workflow to find a selective antigen for each patient is not possible in most therapeutic settings. Here we describe an autocrine-based format that allows identification of peptide antigens selective for individual BCR's with a speed compatible with their use in the clinic. These selected antigens can be used as guide molecules for CAR-T or other approaches such as radiotherapy. The main point is that autocrine-based selections allow for the speed and specificity that are required if personalized therapy of lymphoma is to be realized.

Materials and Methods

Identification and Reconstitution of Lymphoma Cells BCR

Lymph nodes biopsies from patients with follicular lymphoma diagnosis (FL) were kindly provided by N. N. Petrov Research Institute of Oncology (St. Petersburg, Russia). Immediately after surgery the biopsy sample was separated to four equal slices, two of them were loaded into the RNAlater reagent (Qiagen) and others were cryopreserved. Lymphoma cell counts and expression of surface Ig is determined by flow cytometry. Cell suspension aliquots containing approx. 250,000 cells were stained with monoclonal antibodies in 4 tubes: 1. Isotype control; 2. CD45-FITC, CD20-PE, CD3-PCS, CD19-PE-Cy7; 3. IgG-PE-Cy5, IgM-FITC, CD19-PECy7; and 4. kappa-FITC, lambda-PE, CD19-PE-Cy7. Immunoglobulin expression was estimated on lymphocytes as gated using SSC/FSC and CD19C. Monoclonal immunoglobulin expression of either M or G heavy chain, either kappa or lymbda light chain was detected. The RNAlater processed biopsy samples were used for isolation of the total mRNA using RNAeasy Mini Kit (Qiagen). Total cDNA was synthesized by reverse transcription using a QuantiTect Reverse Transcription Kit (Qiagen). Variable region genes of heavy and light Ig chains identified by flow cytometry were amplified in separate reactions for each gene. Semi-nested PCR using high-fidelity DNA-polymerase (Q5, NEB) with a set of family specific V-gene forward primers and a C-gene specific reverse primer was used (Table 1). First step PCR products were subjected to heteroduplex analysis in polyacrylamide gel to discriminate homoduplexes (monoclonal PCR products) from a smear of slowly moving heteroduplexes (derived from polyclonal lymphocytes). DNA fragments of the expected size are extracted and the DNA eluted. Proximal reverse C-gene specific primer was used for the second step amplification and sequencing. Identified variable fragments of the follicular lymphoma BCRs were cloned as a scFv into the lentiviral vector pLV2-Fc-MTA coding for a membrane-anchored human antibody Fc fragment (5) (FIGS. 5B and 5C) (FL). Jurkat and Raji cells were transduced with these viruses. Transduced Jurkat-FL and Raji-FL were analyzed by FACS in order to select the cells carrying the follicular lymphoma BCR, which were then used for autocrine selections or animal experiments.

TABLE 1

List of primers for variable region genes of heavy and light Ig chains amplification.

| Primer | Sequence 5'-3' | Orientation |
|---|---|---|
| L-VH1-start | ATGGACTGGACCTGGAGGATCCT (SEQ ID NO: 4) | forward |
| L-VH2-start | ATGGACATACTTTGTTCCACGCTC (SEQ ID NO: 5) | forward |
| L-VH3-start | ATGGAGTTTGGGCTGAGCTGG (SEQ ID NO: 6) | forward |
| L-VH4-start | ATGAAACACCTGTGGTTCTTCCT (SEQ ID NO: 7) | forward |
| L-VH5-start | ATGGGGTCAACCGCCATCCTC (SEQ ID NO: 8) | forward |
| L-VH6-start | ATGTCTGTCTCCTTCCTCATCTTC (SEQ ID NO: 9) | forward |
| IgM-3' | CTCTCAGGACTGATGGGAAGCC (SEQ ID NO: 10) | reverse distal |
| IgM-clon | GGAGACGAGGGGGAAAAG (SEQ ID NO: 11) | reverse proximal |
| IgG-3' | GCCTGAGTTCCACGACACC (SEQ ID NO: 12) | reverse distal |
| IgG-clon | CAGGGGGAAGACCGATGG (SEQ ID NO: 13) | reverse proximal |
| Vκ1-clon | GACATCCAGATGACCCAGTCTCC (SEQ ID NO: 14) | forward |
| Vκ2-clon | GATATTGTGATGACCCAGACTCCA (SEQ ID NO: 15) | forward |
| Vκ3-clon | GAAATTGTGTTGACACAGTCTCCA (SEQ ID NO: 16) | forward |
| IGKC-3' | CCCCTGTTGAAGCTCTTTGT (SEQ ID NO: 17) | reverse distal |
| IGKC-clon | AGATGGCGGGAAGATGAAG (SEQ ID NO: 18) | reverse proximal |
| VL1_(51)_clon | CAGTCTGTGTTGACGCAGCCGCCCTC (SEQ ID NO: 19) | forward |
| VL1_(36-47)_clon | TCTGTGCTGACTCAGCCACCCTC (SEQ ID NO: 20) | forward |
| VL1_(40)_clon | CAGTCTGTCGTGACGCAGCCGCCCTC (SEQ ID NO: 21) | forward |
| VL2-clon | TCCGTGTCCGGGTCTCCTGGACAGTC (SEQ ID NO: 22) | forward |

TABLE 1-continued

List of primers for variable region genes of heavy and light Ig chains amplification.

| Primer | Sequence 5'-3' | Orientation |
|---|---|---|
| VL3-clon | ACTCAGCCACCCTCGGTGTCAGTG (SEQ ID NO: 23) | forward |
| VL4-clon | TCCTCTGCCTCTGCTTCCCTGGGA (SEQ ID NO: 24) | forward |
| VL5-clon | CAGCCTGTGCTGACTCAGCC (SEQ ID NO: 25) | forward |
| IGLC-3' | GTGTGGCCTTGTTGGCTTG (SEQ ID NO: 26) | reverse distal |
| IGLC2-7_clon | CGAGGGGGCAGCCTTGGG (SEQ ID NO: 27) | reverse proximal |
| IGLC1_clon | AGTGACCGTGGGGTTGGCCTTGGG (SEQ ID NO: 28) | reverse proximal |

Construction of a CAR-Based Combinatorial Peptide Library

Figure 5C:
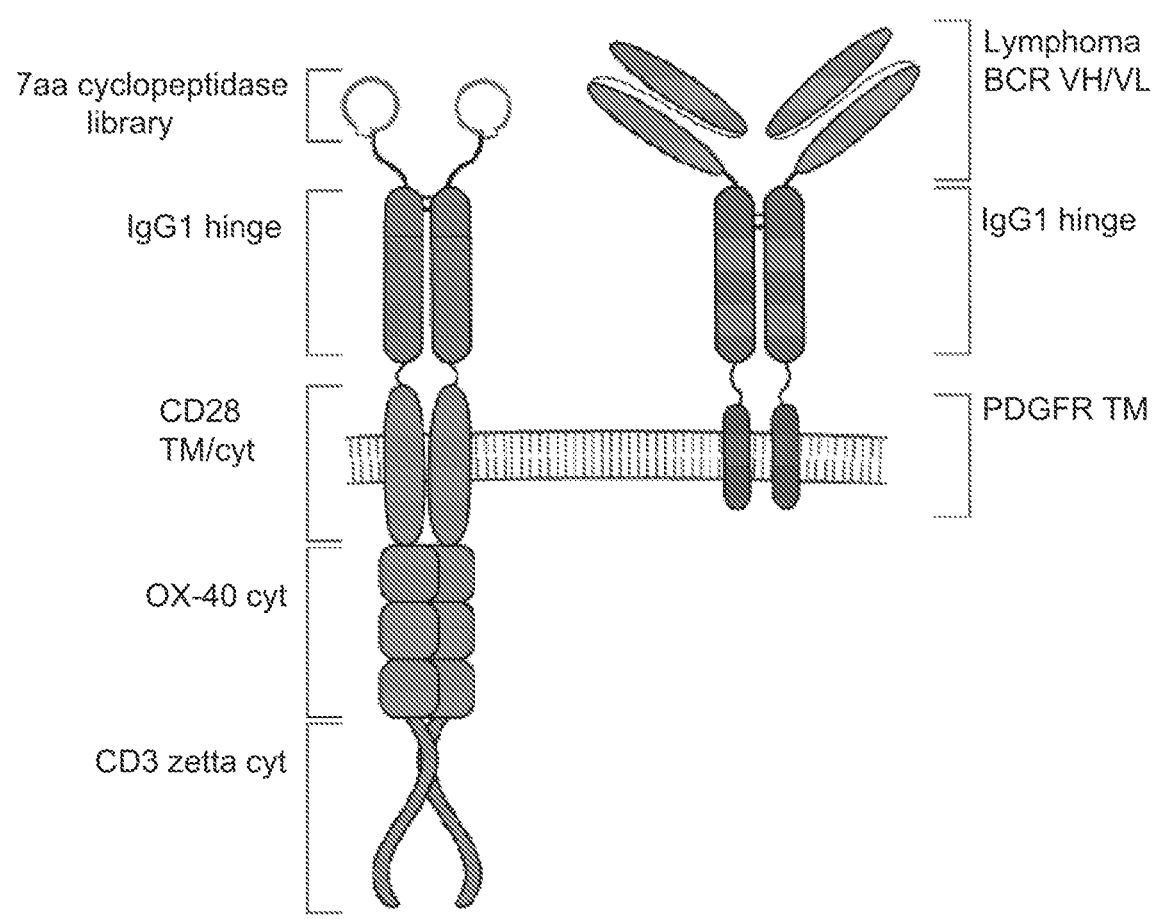

The DNA fragment coding for the 3rd generation chimeric antigen T-cell receptor was synthesized (GeneCust) and cloned into the pLV2 lentiviral vector (Clontech) under control of the EF1a promoter. The arrangement of genes are in the order of: interleukin 2 signal peptide at the N terminus; IgG1 Fc spacer domain with modified PELLGG and ISR motifs; GGGS linker; a CD28 trans-membrane and intracellular region; intracellular domains of the OX-40 and CD3zeta (FIGS. 5A and 5C). To construct the combinatorial cyclopeptide library, randomized peptides in the format of $CX_7C$, (X=20 natural amino acids) were appended to the N terminus of the Fc domain by PCR using oligonucleotides with degenerate NNK codons. The diversity of the generated library was estimated as $10^9$ members. The lentiviral library of $CX_7C$-Fc-CAR was prepared by co-transfection of HEK293T cells with the library plasmid and the packaging plasmids. Supernatants containing virus were collected at 48 h post transfection. The titer of lentivirus preparations was determined using Lenti-X p24 ELISAs (Clontech).

FACS-Based Sorting

Jurkat-FL1, Jurkat-FL2 and Jurkat-FL3 cells were transduced with the lentiviral cyclopeptide-CAR library. Two days post-infection, CD69-positive cells were sorted using a FACSAria III (BD Biosciences). The peptides sequences were determined directly from sorted cells by PCR of the genes that encode them and were cloned into the lentiviral vector to construct libraries for the next round of selection. Four iterative rounds of selection were carried out.

Cells and Culturing Conditions

Cell lines were cultured in media supplemented with 10% FBS (Gibco), 10 mM HEPES, 100 U/ml penicillin, 100 ug/ml streptomycin, and 2 mM GlutaMAX (Gibco). The 293T lentiviral packaging cell line (Clontech) and HEp-2 cell line were cultured in DMEM (Gibco). Human HEp-2 (CCL-23), Jurkat (TIB-152) and Raji (CCL-86) cell lines were obtained from the Institute of Cytology RAS culture collection (St. Petersburg, Russia). The Jurkat, Jurkat-FL, Raji and Raji-FL cell lines were cultured in RPMI (Gibco). Human peripheral blood mononuclear cells (PBMCs) were isolated from the blood of healthy donors by gradient density centrifugation on a Ficoll-Paque (GE Healthcare), washed and then re-suspended in serum-free RPMI.

CD8+ T Cell Activation, Expansion and Transduction

Dynabeads CD8 Positive Isolation Kit (Life Technologies) was utilized for isolation of CD8 T cells from human PBMCs. Human CD8 T cells were activated with CD3/CD28 beads at a 1:1 ratio (Life Technologies) in a complete RPMI media containing 40 IU/ml recombinant IL-2 for 72 hours. Activated T cells were re-suspended at concentration of 4 million cells per 3 ml of FL1-CAR, FL2-CAR, FL3-CAR, CD19-CAR or Myc-Fc-CAR in lentiviral supernatant plus 1 ml of fresh RPMI media with 40 IU/ml IL-2 and cultured in 6-well plates. Plates were centrifuged at 1200×g for 90 minutes at 32° C. and then incubated for 4 hours at 37° C. Second and third transductions were performed two more times.

Animal Experiments

All animal procedures were carried out in a strict accordance with the recommendations for proper use and care of laboratory animals (ECC Directive 86/609/EEC). The protocol was approved by the Inter-Institute Bioethics Commission of the Siberian Branch of the Russian Academy of Sciences (SB RAS). The experiments were conducted in the Center for Genetic Resources of Laboratory Animals at the Institute of Cytology and Genetics, SB RAS. Six- to eight-week-old female NOD SCID (CB17-Prkdc$^{scid}$/NcrCrl) mice with an average weight of 16-20 g were used. Tumors were engrafted by inoculating of 5×10$^6$ Raji-FL1 cells in 200 µL 0.9% saline solution subcutaneously into the left side of mice. Once tumors had reached a palpable volume of at least 50 mm$^3$, mice were randomly assigned to experimental or control groups. Tumor-bearing mice were injected intravenously (i.v.) with 3×10$^6$FL1-CART, CD19-CART or Myc-CART cells on day 17$^{th}$ post tumor inoculation. Tumor volume was measured with calipers and estimated using the ellipsoidal formula. Animals were sacrificed when the volume of the tumor node reached 2 cm$^3$. On the 38th day after tumor inoculation (21st day post CART infusion), animals from each experimental group were used for isolation of blood, spleen and bone marrow cells. Erythrocytes were lysed with RBC lysis buffer (0.15 M NH$_4$Cl, 10 mM NaHCO$_3$, 0.1 mM EDTA) and cells were stained with antibodies specific for CD3 (for blood samples), CD45RA and CCR7 and analyzed by Novocyte flow cytometer (ACEA Biosciences). The tumors were fixed in 4% neutral buffered formaldehyde for 2 weeks and processed for paraffin sectioning utilizing standard protocols.

Biophotonic Tumor Imaging

Animals were injected intraperitonealy with 150 µl (4.29 mg per mouse) of a freshly thawed aqueous solution of D-luciferin potassium salt (GOLDBIO). After 10 minutes animals were sacrificed and brain, lungs, heart, liver, spleen, kidneys, and tumors were collected. Each organ was rinsed with PBS and bioluminescence intensity was visualized utilizing an In-Vivo MS FX PRO Imaging System (Carestream).

Histology and Immunohistochemistry

A macroscopic post-mortem analysis included examination of the external surfaces, appearance of primary tumor nodes, thoracic condition, abdominal and pelvic cavities with their associated organs and tissues. For further histological evaluation, specimens of tumor nodes from each animal were collected during autopsy and fixed in 10% neutral-buffered formalin, dehydrated in ascending ethanols and xylols, and embedded in HISTOMIX paraffin (BioVitrum). Paraffin sections (5 µm) were stained with hematoxylin and eosin, microscopically examined and scanned. Tumor sections for immunohistochemical (IHC) studies (3-4 µm) were sliced on a Microm HM 355S microtome (Thermo Fisher Scientific), and further de-paraffinated and rehydrated; antigen retrieval was carried out after exposure in a microwave oven at 700 W. The samples were incubated with the CD8-specific antibodies (M3164, Spring BioScience) according to the manufacture's protocol. Next, the sections were incubated with secondary HRP-conjugated antibodies (Spring Bioscience detection system), exposed to DAB substrate, and stained with Mayer's hematoxylin. Images were obtained using a Axiostar Plus microscope equipped with a Axiocam MRc5 digital camera (Zeiss, Germany) at 10×, 20× and 40× magnifications. Gross examination of tumors included evaluation of size of the tumor node, presence of a capsule, and presence of necrosis and hemorrhages. Microscopic examination of tumors included evaluation of histopathological changes in tumor tissue in terms of necrosis and apoptosis, presence of mitoses and presence of CD8-lymphocyte infiltration.

Statistics

The data obtained ex vivo (flow cytometry, cytotoxicity test) were statistically processed using the Student's t-test (two-tailed, unpaired). The tumor volume measurements were statistically processed using one-way ANOVA (STATISTICA 10.0). Survival curves were generated using the Kaplan-Meier method, and statistical comparisons were performed using the log-rank (Mantel-Cox) test. Significance was considered for p<0.05.

Cytotoxicity Assays

The cytotoxicity and specificity of engineered T cells were evaluated in a standard lactate dehydrogenase (LDH) release assay (CytoTox 96® Non-Radioactive Cytotoxicity Assay, Promega) following manufacturer's recommendations. Mock transduced, CD19-CAR, FL1-CAR, FL2-CAR, FL3-CAR, or Myc-CAR T cells were co-incubated for 6 hours together with 10$^4$ of the Raji-FL1, Raji-FL2, Raji-FL3 or cells from the patient's biopsy in a complete RPMI media supplemented with 40 U/ml of human IL-2. As negative controls Raji cells or cells isolated from an irrelevant lymphoma lymph node biopsy were used. All the experiments were performed in triplicate.

Flow Cytometry Analysis

The following antibodies were used in this study; anti-human CD3 FITC (Biolegend), anti-human CD8 PE (Biolegend), anti-human CCR7 PE (Biolegend), anti-human CD45RA FITC (Biolegend), mouse anti-human CD69 Alexa Fluor488 (Biolegend), anti-human B220 APC (Biolegend). Chimeric FL-BCR expression was detected using anti-human IgG1 PE antibody (SouthernBiotech) or synthetic biotinylated cyclopeptides (GeneCust) and streptavidin conjugated with FITC or PE (Thermo Fisher Scientific). The CAR molecules were detected using goat cross-absorbed anti-human IgG antibody conjugated with DyLight650 (Thermo Fisher Scientific). The CD19-CAR (FMC63 clone) molecules were detected using biotinylated protein L (Thermo Fisher Scientific) and streptavidin conjugated with FITC (Thermo Fisher Scientific).

Identification of the Bcl-2 Translocation

Crude DNA extracts were prepared by proteinase K digestion of follicular lymphoma lymph node biopsy sample. PCR amplification was carried out using primer pairs comprising a consensus primer to JH and one of the three different primers homological to sequences in the mbr1, mcr2 or icr5 regions of bcl2 gene as described in (14).

IFA

Self-reactivity of the lymphoma BCR was tested by indirect immunofluorescence assay (IFA) on HEp-2 and HEL293T cells as described in (15). Plasmid vector encoding recombinant myoferlin (22443, Addgene) was transfected into the HEK293T cells with Lipofectamine 2000

(Invitrogen) as per the manufacturer's instructions. Recombinant Igs representing lymphoma BCR and irrelevant human antibody were diluted in PBS with 2% BSA and used at a concentration of 50 µg/mL and incubated with cells for 1 hour. Detection of bound antibodies were accomplished by anti-human Ig-PE using Nikon Eclipse Ti U microscope.

Results

Overall Workflow

The aim of these proof-of-concept experiments is to find an antigen that selectively reacts with the BCR on the surface of the lymphoma cell (FIG. 1). The central idea is that if the BCR can be cloned and expressed on the surface of indicator cells also expressing a very large array of peptides, the system becomes autocrine and each cell becomes a selection system onto itself. If the overall system is constructed such that the BCR signals when it reacts with one of the co-expressed ligands, specific interactions between the BCR and the ligand can be readily identified by FACS. Importantly, the autocrine-based selection, as used here, selects for functional interactions where antibody binding to the peptide on the CAR activates the system.

Identification of the BCRs on Malignant B Cells

Lymph node biopsies from 3 patients with Follicular lymphoma (FL) were used to determine the nucleotide sequence of the BCRs from malignant cells. The central part of the tumor biopsy was taken in order to reduce the abundance of BCR genes from non-malignant cells. Total mRNA was used as a template in a reverse transcription reaction with subsequent PCR amplification of Ig V genes. Up to 95% percent of analyzed sequences were identical due to the clonal nature of lymphomas. The selected Ig variable regions were cloned into the pComb3X vector in a scFv format (5). Thus, the ScFv fused with constant domain of antibody (Fc) is linked via a flexible linker to a membrane-spanning domain of the platelet-derived growth factor receptor (PDGFR) such that the antibody molecules are integrated as dimers into the plasma membrane with their binding sites facing the solvent (5) (FIGS. 5B and 5C).

Autocrine-Based Selection of a Ligand for the BCR on the Malignant Cells

Figure 2A:
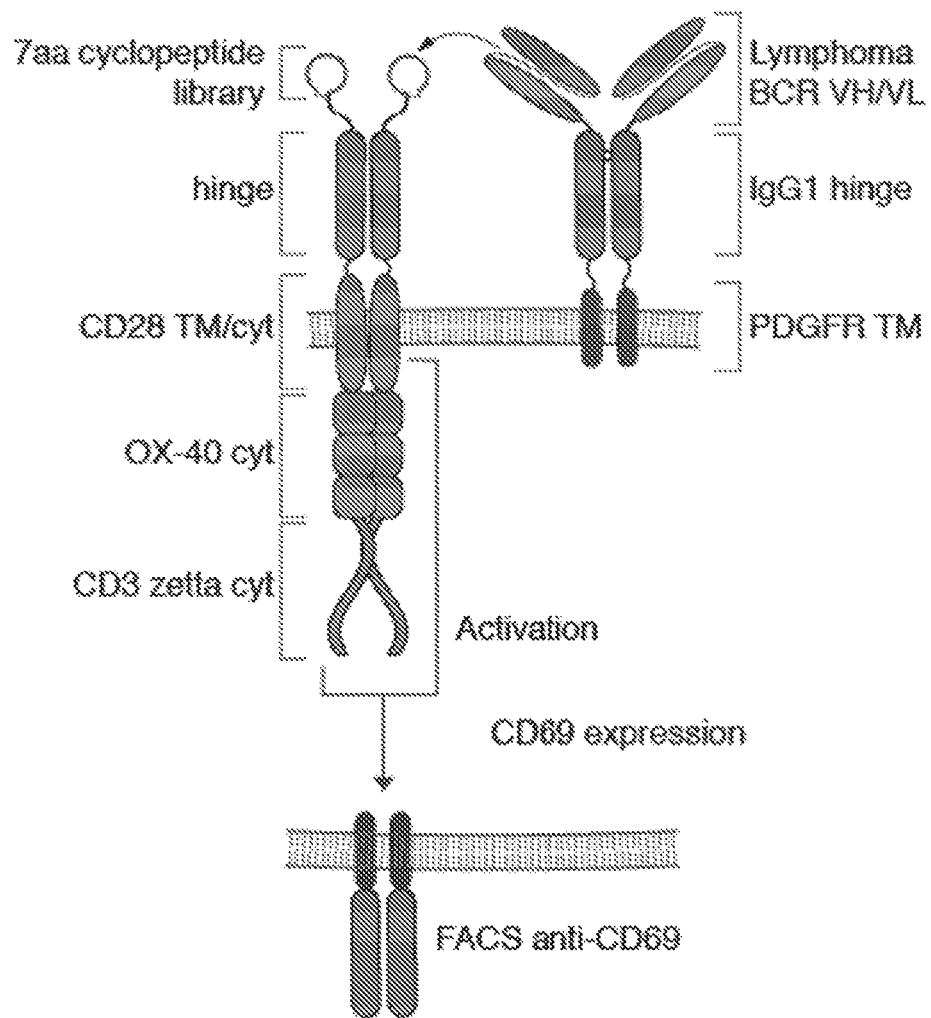
FIGS. 2A-2C shows autocrine-based selection of malignant FL-BCR ligands.

An autocrine-based reporter system for direct selection of ligands that are specific to the BCR on malignant cells (FIG. 2A) was used. The method allows direct selection of a ligand that may be used for tumor targeting. T cells infected with both the BCR and combinatorial cyclopeptide library containing $10^9$ members were used as the reporter system. Immortal Jurkat human T lymphocytes were modified to simultaneously express the lymphoma BCR and a randomized 7 amino acid cyclopeptide library. The cyclopeptide library was fused with a chimeric antigen receptor containing signaling domains (FIGS. 5A-5C). When the Ig fused with the PDGFR membrane-spanning domain reacts with a peptide from the cyclopeptide library, the signaling domains of the chimeric antigenic receptor trigger a T cell activation cascade. Activated T-cells start to express CD69 (early T-cell activation antigen) (6) and thus may be easily detected utilizing specific fluorescent-labeled antibodies.

Figure 2B:
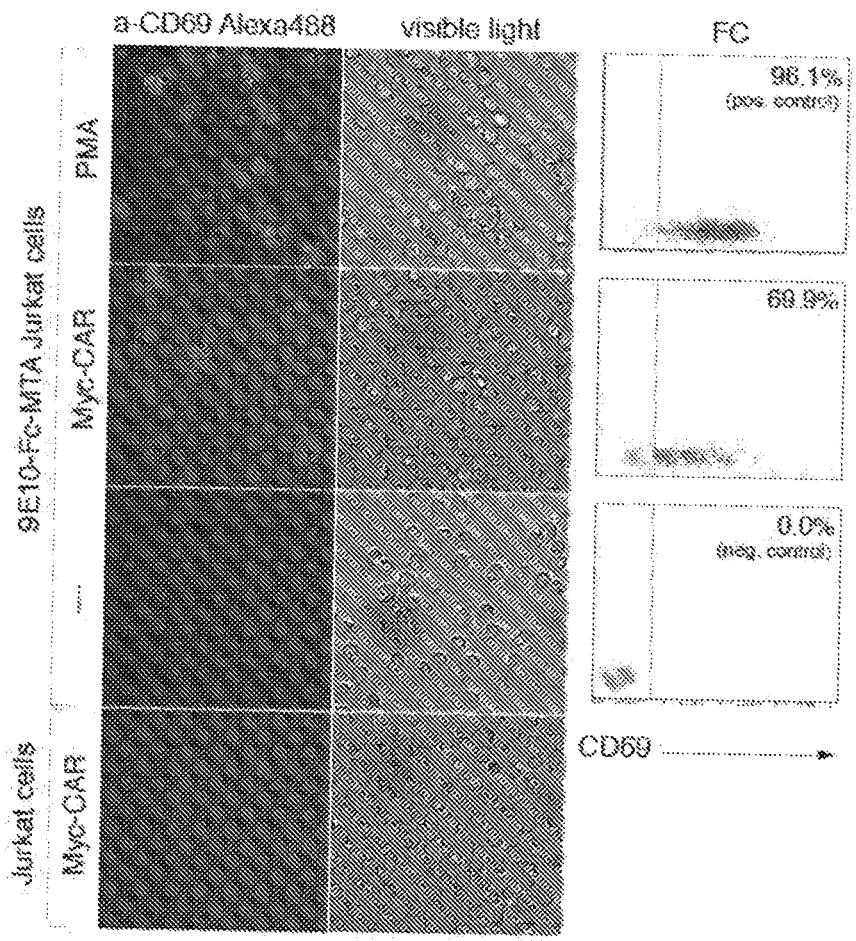

First, the capacity of the reporter construction was confirmed using a model system. A c-Myc epitope on CAR and the variable domains of the anti-Myc antibody (9E10 clone) was used as a model membrane bounded BCR. Jurkat cells expressing only membrane-bound anti-Myc antibody without co-expression of Myc-CAR showed no detectable activation. But, cells containing both membrane-bound anti-Myc antibody and Myc-CAR were activated FIG. 2B).

Figure 2C:
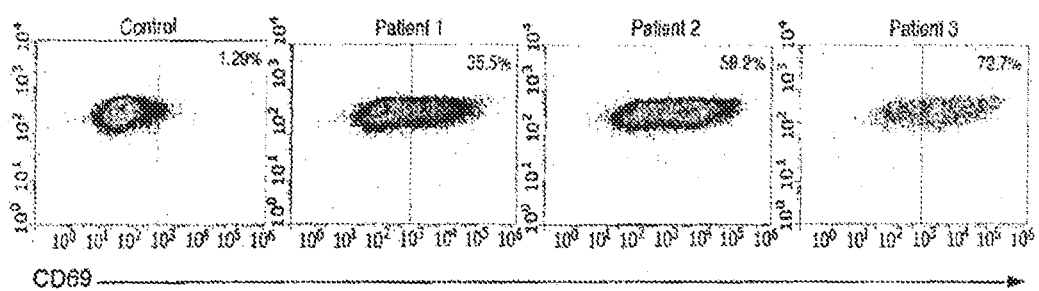

The results from the Myc model system encouraged us to move forward to the actual BCR from the patient with lymphoma. In order to select peptide ligands of the reconstituted lymphoma BCRs, several rounds of selection were performed, resulting in discovery of the three cyclopeptides CILDLPKFC (FL1) (SEQ ID NO: 1), CMPHWQNHC (FL2) (SEQ ID NO: 2) and CTTDQARKC (FL3) (SEQ ID NO: 3) specific for three patient derived BCRs scFv. Individual selected peptides-CAR fusions trigger a T cell activation cascade in Jurkat cells when co-transduced by corresponding membrane tethered BCRs as measured by CD69 membrane expression (FIG. 2C).

Specific Lytic Activity Against Lymphoma Cells

Figure 3A:
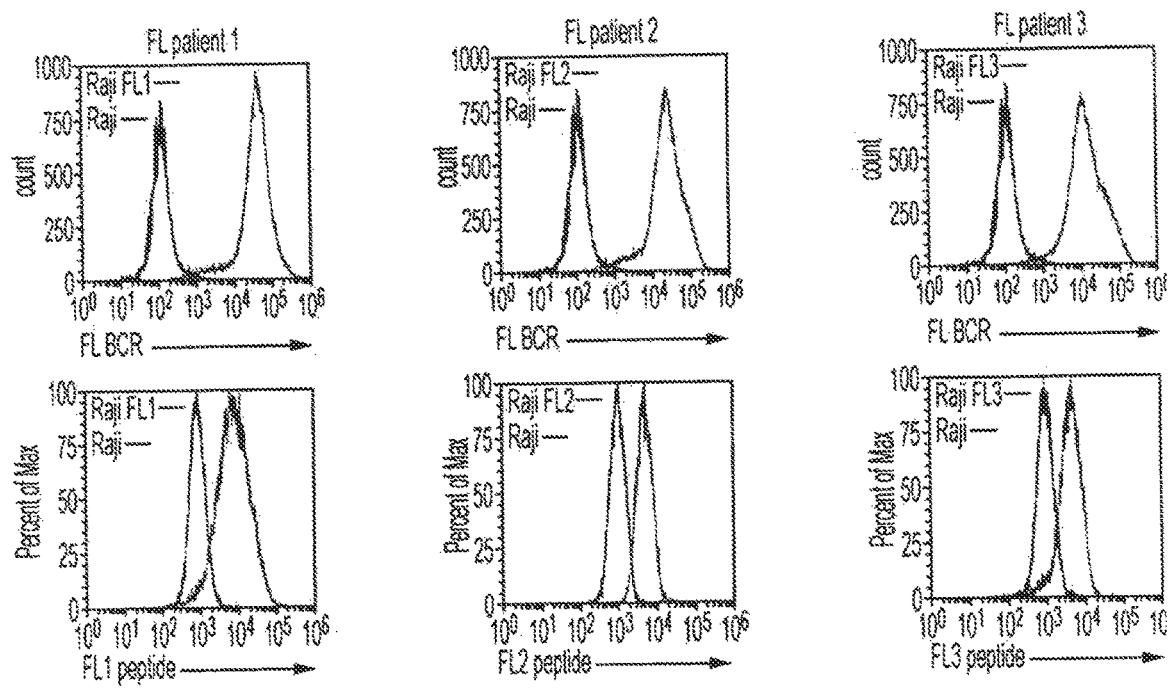
FIGS. 3A-3D are graphs showing the selected peptide ligands specifically interact with the FL-BCRs and redirects CTLs to kill tumor cells.

Next, it was tested whether T cells transduced with the FL1-CAR, FL2-CAR and FL3-CAR constructs demonstrated killing activity in vitro when incubated with the Raji lymphoma cell lines transduced with the isolated follicular lymphoma B cell receptors (FL-BCR). Surface expression of the functional BCR from the malignant cells was confirmed by staining with a-Fc antibody and biotinylated FL1, FL2 and FL3 peptides (FIG. 3A). These studies confirmed that BCRs capable of binding to the peptides were present on these cells.

Figure 3B:
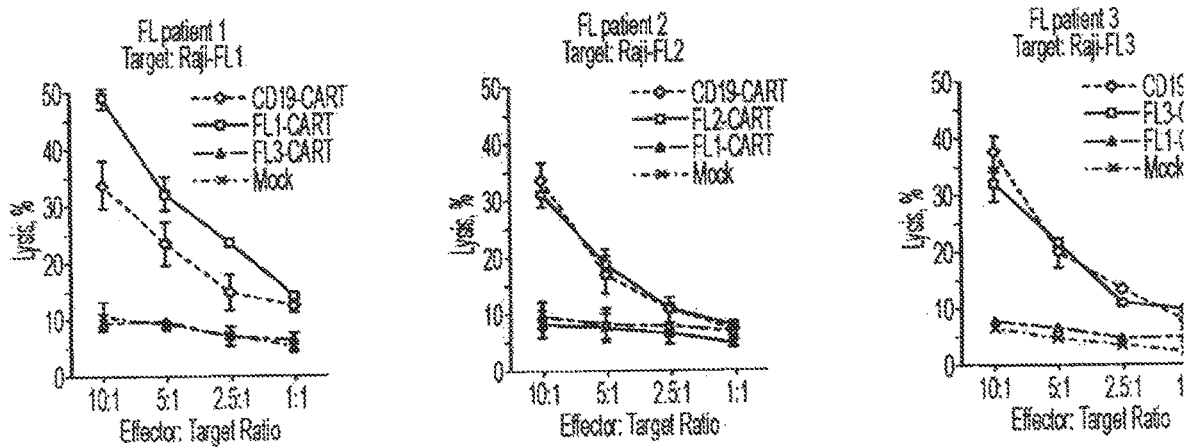
Figure 6:
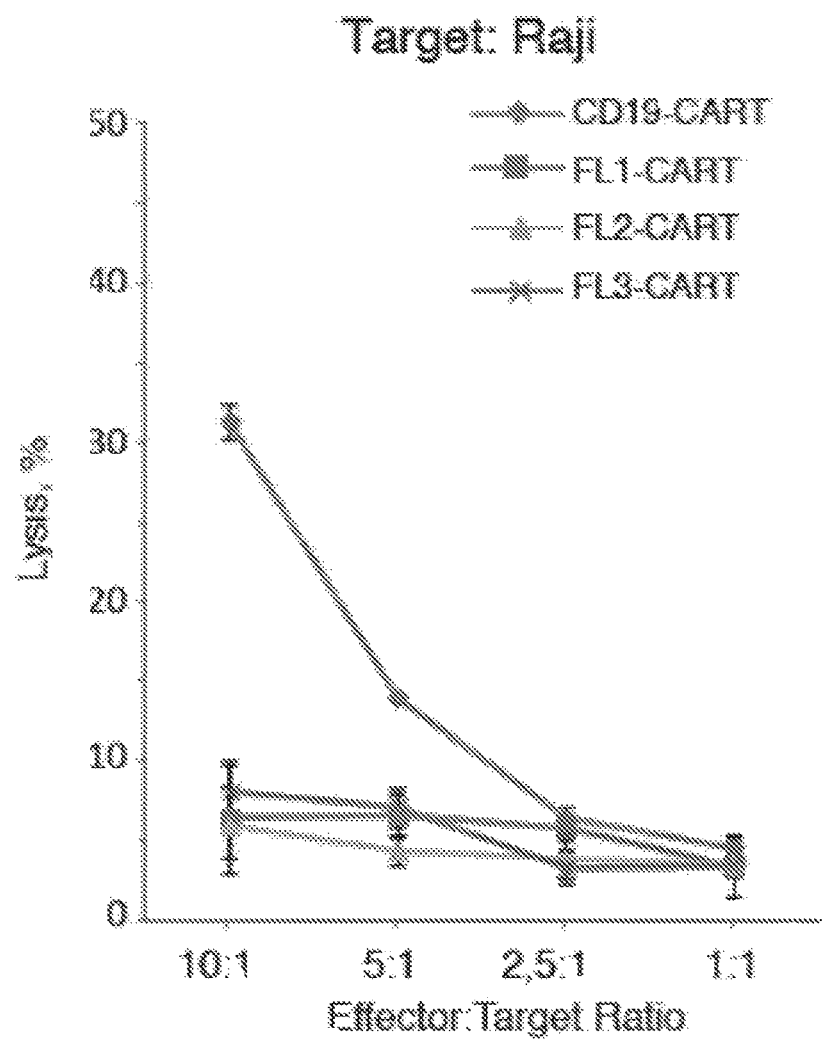
FIG. 6 shows that FL-CARTs do not eliminate Raji cells without exogenous lymphoma BCR. Only CD-19 CART showed killing activity on regular Raji cells. Minimum unspecific lysis was observed when FL1-CAR, FL2-CAR and FL3-CAR T cells were incubated with Raji cells. Cytotoxicity was determined by measuring lactate dehydrogenase release after 6 hours.
Figure 7A:
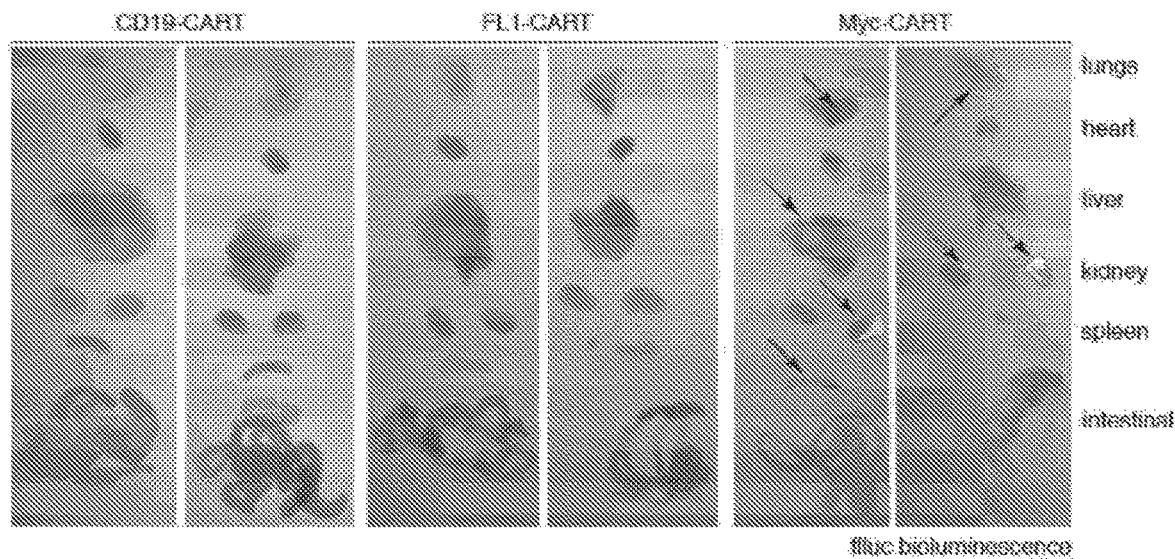
FIGS. 7A-7C shows that CTLs redirected by FL1-CAR infiltrate solid tumors and prevent xenograft metastasis.
Figure 7B:
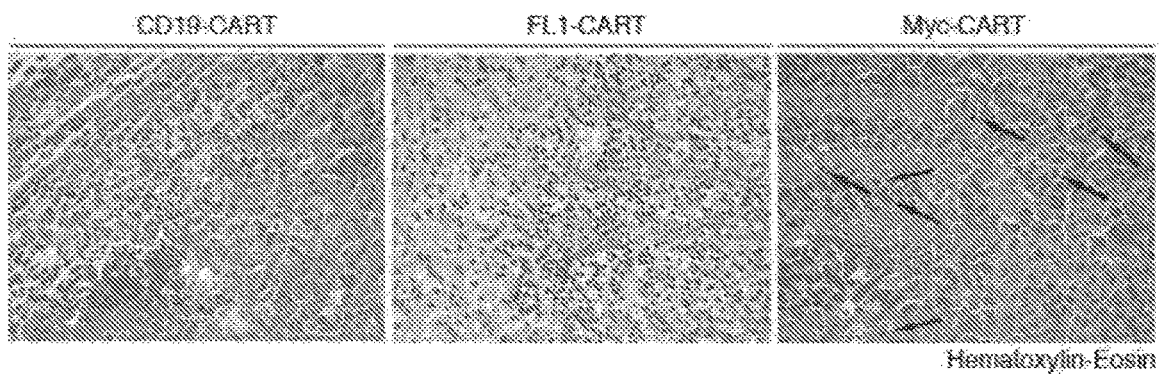
Figure 7C:
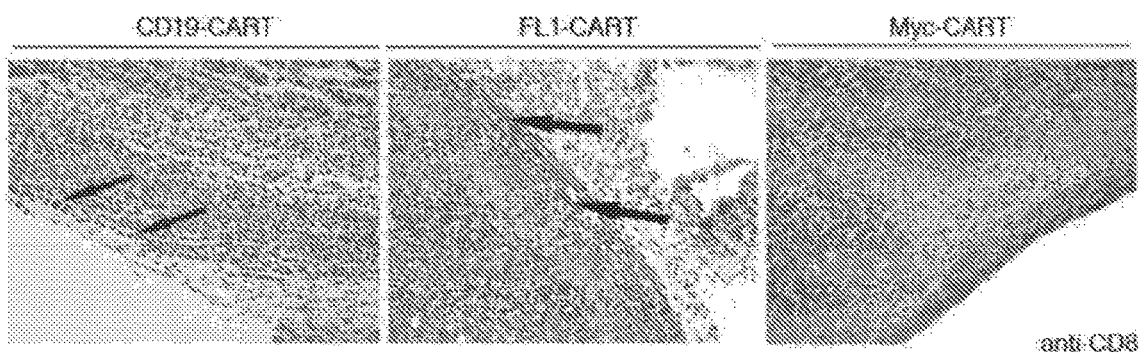
Figure 8A:
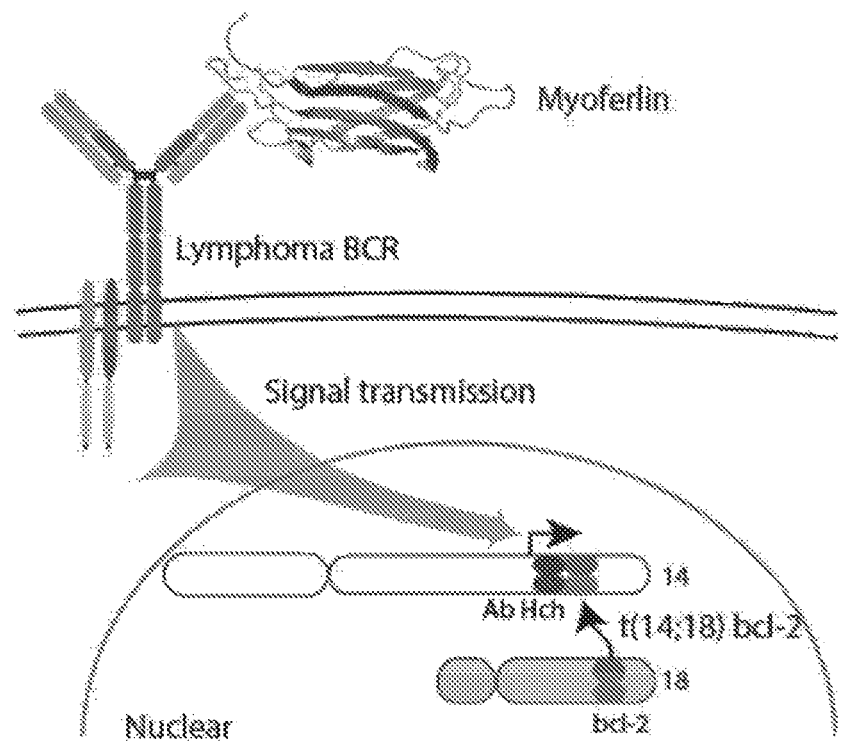
Figure 8B:
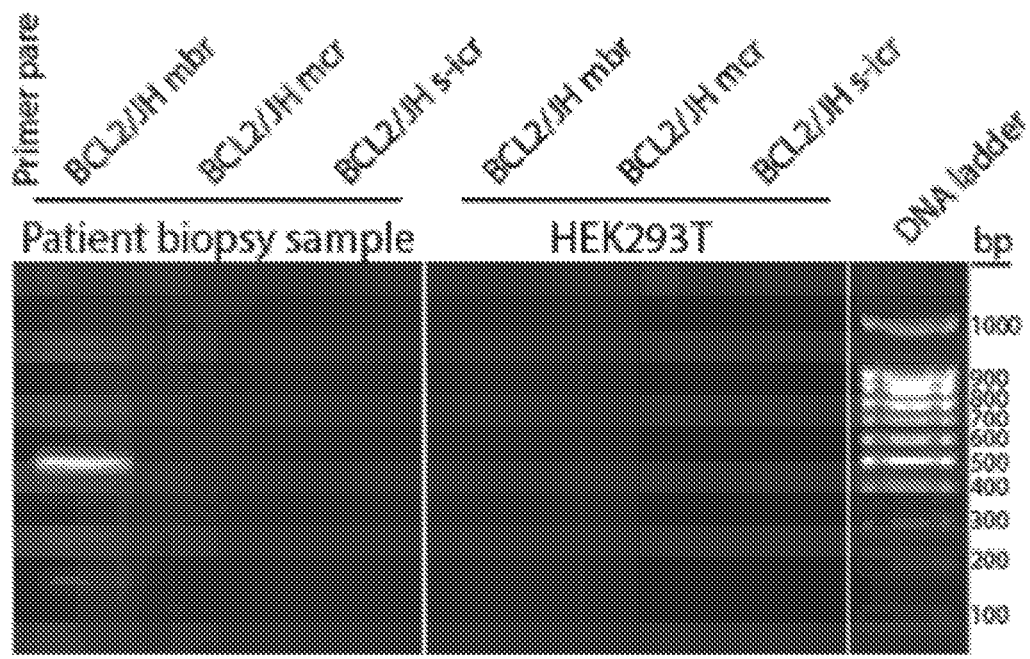

To determine if CTLs expressing CAR-T were capable of killing target cells, lentiviral vectors coding for the FL1-CAR, FL2-CAR, FL3-CAR or CD19-CAR were used to transduce human $CD8^+$ T cells. Activated human $CD8^+$ T-cells baring peptide-CAR lysed Raji cells expressing the corresponding BCRs from the lymphomas (Raji-FL1, Raji-FL2 and Raji-FL3), as measured by LDH release (FIG. 3B). Notably, the specific cytotoxicity of the FL1-CAR, FL2-CAR and FL3-CAR cells was comparable to the best-studied CD19 CAR-T cell targeting CD19 antigen (FMC63-CAR). In contrast, minimum lysis was observed when control CARs T cells were used. Also, no cell lysis was observed in case of incubation of FL1-CAR, FL2-CAR and FL3-CAR with unmodified Raji cells, suggesting high therapeutic potential and safety of the BCR targeting CART (FIG. 6).

Figure 3C:
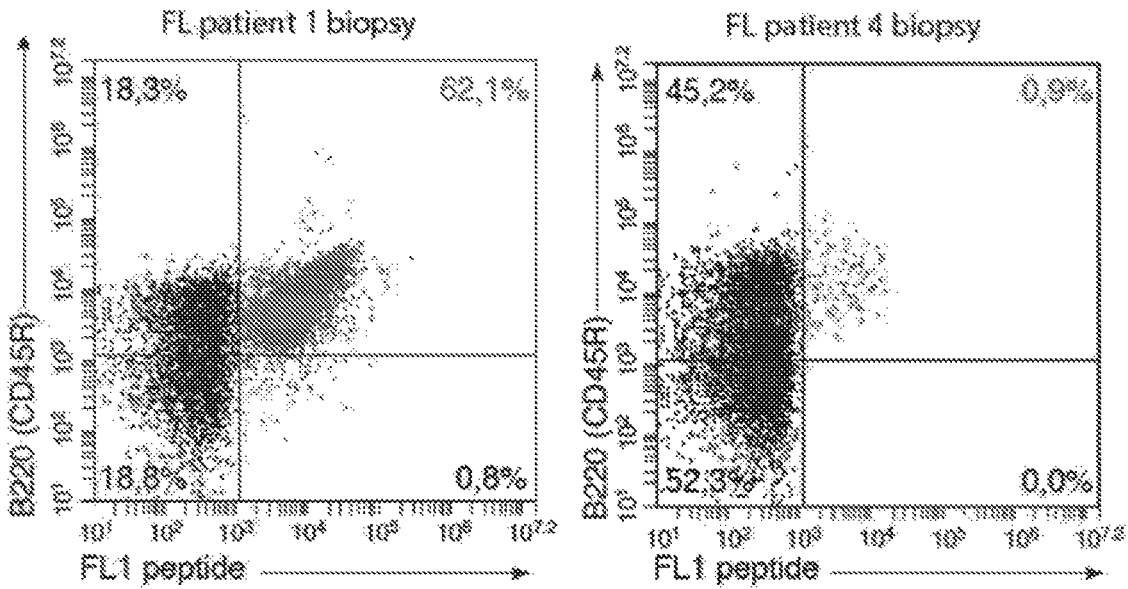
Figure 3D:
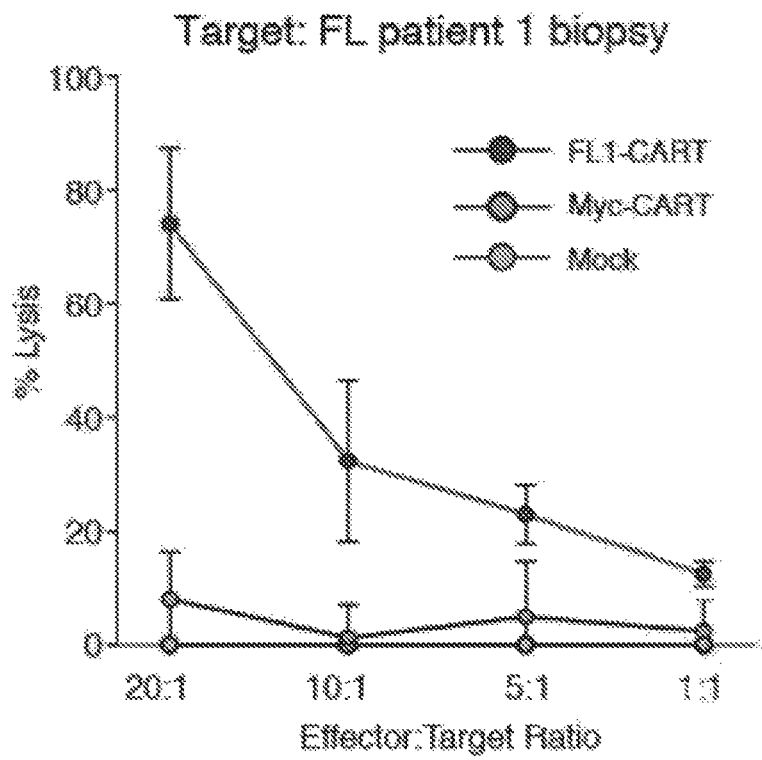

Next, cytotoxicity was estimated ex vivo of the FL1-CART against cells from the patient 1 initial biopsy. More than 60% of cells in biopsy sample are B-cells specific to the FL1 peptide (FIG. 3C, bottom panels). Cells from a control biopsy sample derived from another patient with follicular lymphoma (patient 4) did not demonstrate any significant staining by FL1 peptide. The CTL assay showed that FL1-CAR-T specifically lysed cells from the biopsy sample, while Myc-CAR-T and Mock T cells did not have any anti-tumor lytic activity (FIG. 3D).

FL1-CAR Redirected CTLs Suppress Lymphoma Cells In Vivo

Figure 4A:
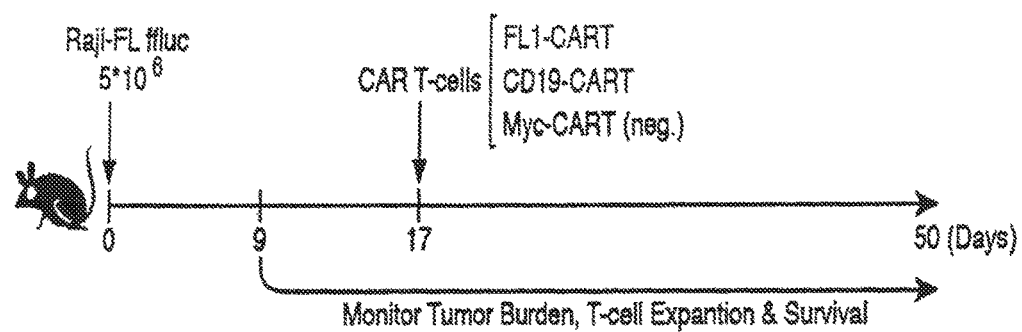
FIGS. 4A-4F show CTLs re-directed by FL1-CAR suppress lymphomagenesis in vivo.
Figure 4B:
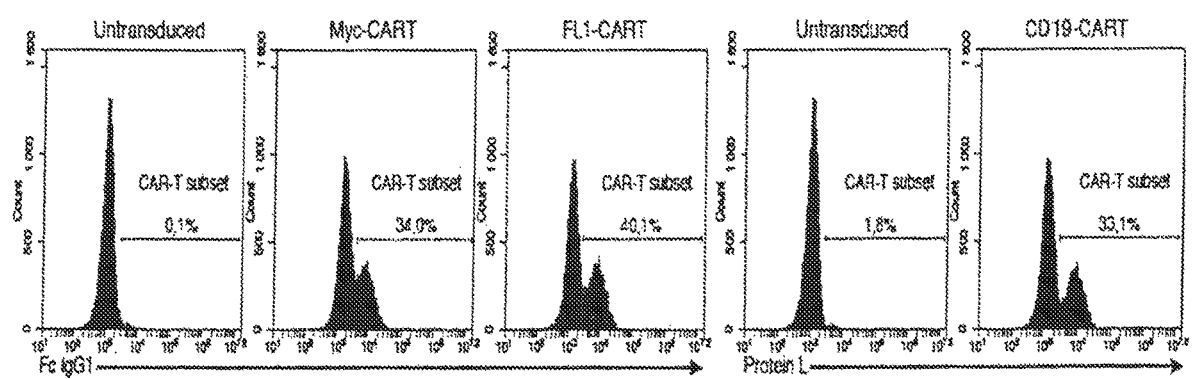
Figure 4C:
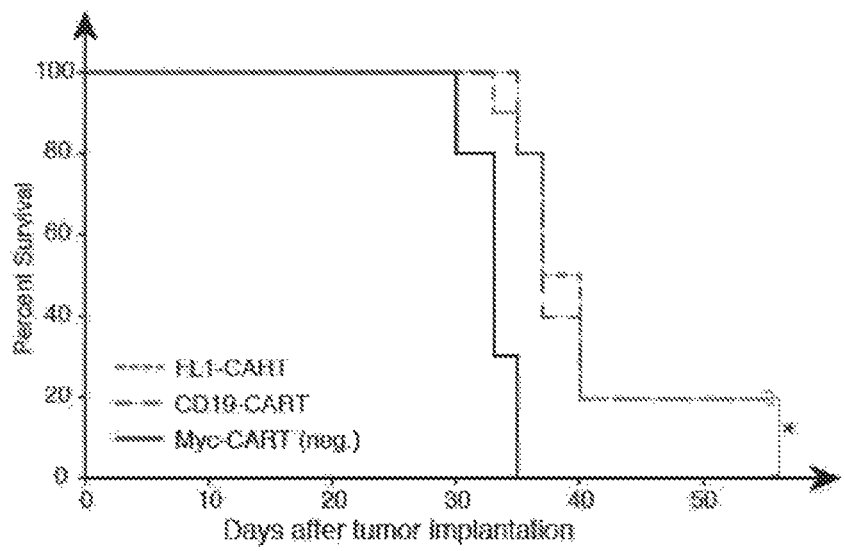
Figure 4D:
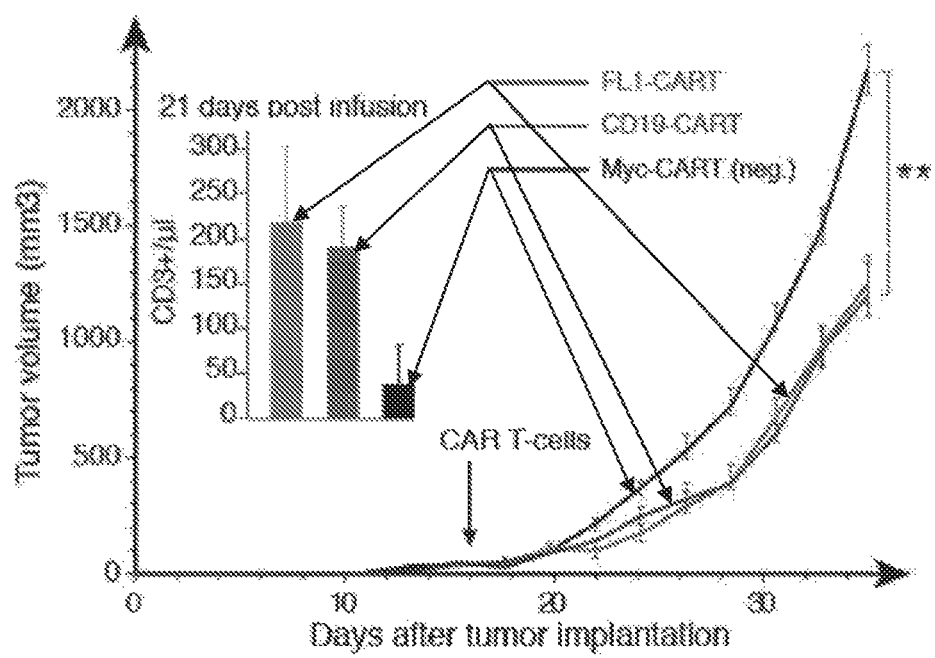
Figure 4E:
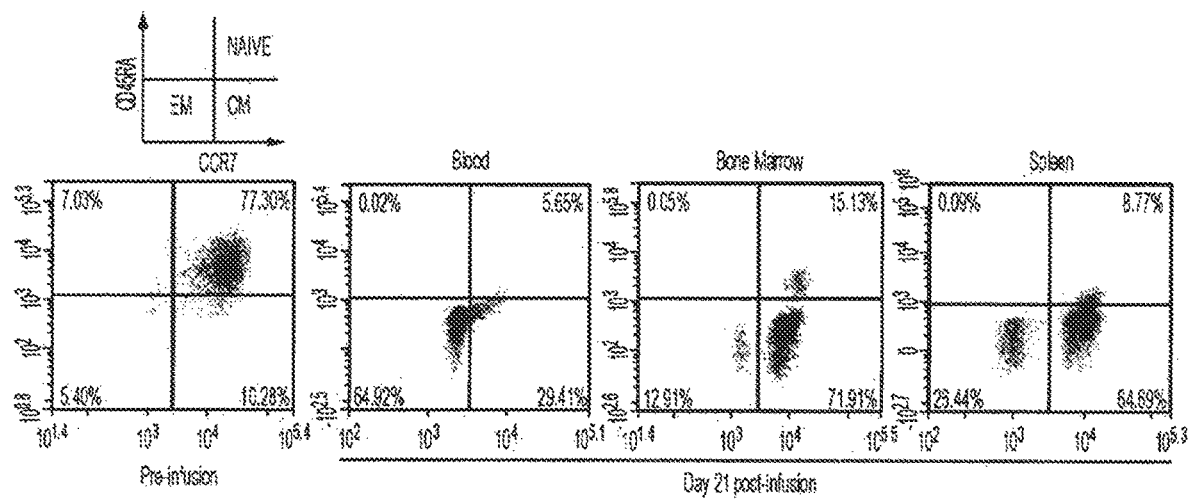
Figure 4F:
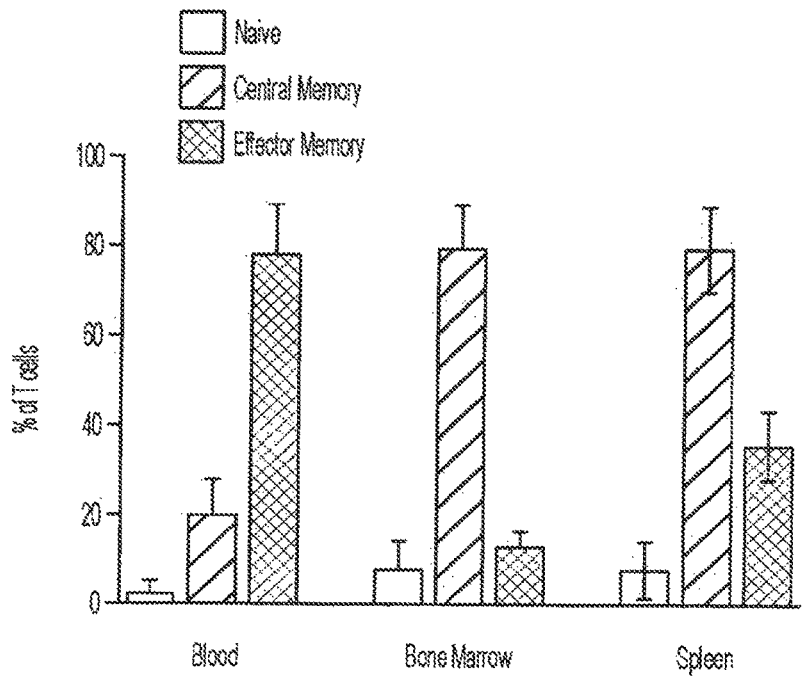

The efficacy of FL1-CART was tested in a relevant model of follicular lymphoma using immune-deficient NOD SCID (CB17-Prkdc$^{scid}$/NcrCrl) mice engrafted with $5 \times 10^6$ Raji cells expressing the FL1-BCR (Raji-FL1) (FIG. 4A). Lentiviral vectors coding for FL1-CAR, Myc-CAR or CD19-CAR were used to transduce CD3/CD28 bead-activated human $CD8^+$ T cells resulting in a high efficiency of gene transfer (FIG. 4B). Injection of $5 \times 10^6$ FL1-CART or CD19-CART significantly suppressed the tumor burden and improved survival in comparison with control group treated by Myc-CART (FIGS. 4C and 4D, FIGS. 7A-7C). On the 37th day 100% mice from the control Myc-CART group were dead compared to 80% alive animals in the FL1-CART and CD19-CART groups. Flow cytometry was used to show that CAR-modified T cells persist in peripheral blood 21 days post infusion, FL1-CAR-T and CD19-CAR-T cells were present in significantly elevated amounts relative to Myc-CAR-T cells (FIG. 4D insert). As expected, expansion of CD8+ CAR-expressing T cells was correlated with expression of surface markers associated with effector phenotypes (FIG. 4E). Interestingly, the population of FL1-CART in peripheral blood generally consisted of an effector memory subset, while spleen and bone marrow were expanded by a central memory subset of cells (FIG. 4F). These later cells are thought to be important for persistence and sustained anti-tumor activity.

Discussion

As immunotherapy expands, a way to discover more tumor antigens and their specific ligands is needed. At present the "menu" of tumor antigens is limited (7-12). However in the case of lymphomas the tumor antigen is already present as the BCR. Moreover, the BCR is an antibody whose physiological role is to bind to antigen. This property of the BCR greatly simplifies the problem of searching for ligands that interact with the malignant BCR. Herein a "forced proximity" autocrine approach (13) was used, in which each reporter cell co-expresses one member of a large peptide library on the cell surface together with the target BCR where they are co-integrated into the membranes of a population of reporter cells. Several rounds of autocrine-based selection allows discovery of a specific peptide ligand for the BCR.

It was demonstrated that T cells modified by these peptides fused with CAR efficiently eliminate tumor cells both, ex vivo and in vivo as efficiently as the well-known CD19-targeted CAR.

One advantage of this approach to antigen selection is that after the rounds of panning the selected peptide ligands are already in a construct where they are fused to the chimeric antigen receptor. This allows one to immediately generate therapeutic T lymphocytes modified by tumor-specific CAR.

In essence the format reported here is the opposite of the usual CART protocol. Usually in cells bearing the CAR-T directionality is govern by antibody and target is a surface peptide or protein of the tumor cell. Here the inverse is used in that binding of the CAR-T is directed by the peptide and a target is an antibody. Moreover, since the antibody molecule is part of a huge diversity system, the target universe is basically unlimited. This large target universe greatly simplifies the problem of selecting ligands that are highly specific and tightly binding.

As more patients are studied, the selected peptide sequences may be used to determine the proteins they are derived from and by inference the driving force for the malignant transformation. In this context, it is interesting the discovered peptide is homologous to a region of Myoferlin and identical to regions of surface proteins from *Streptococcus mitis* and *Pneumocytis jirovecii* (FIGS. 8A-8E). Given that there is a suggestion that some lymphomas such as MALT are driven by sustained exposure to an infectious agent, the driving force for generation of lymphoid malignancies will be investigated as more antigens that bind to the BCR are unearthed. Finally, the ability to use sequences other than CD19 as targets not only expands the choice in a therapeutic setting but also my help when the CD19 is absent or down regulated as may occur in many patients.

References

1. B. S. Kahl, D. T. Yang, Follicular lymphoma: evolving therapeutic strategies. Blood 127, 2055-2063 (2016).
2. K. Basso, R. Dalla-Favera, Germinal centres and B cell lymphomagenesis. Nat Rev Immunol 15, 172-184 (2015).
3. J. O. Armitage, R. D. Gascoyne, M. A. Lunning, F. Cavalli, Non-Hodgkin lymphoma. Lancet, (2017).
4. V. Ribrag, S. Koscielny, J. Bosq, T. Leguay, O. Casasnovas, L. Fornecker, C. Recher, H. Ghesquieres, F. Morschhauser, S. Girault, S. Le Gouill, M. Ojeda-Uribe, C. Mariette, J. Cornillon, G. Cartron, V. Verge, C. Chassagne-Clement, H. Dombret, B. Coiffier, T. Lamy, H. Tilly, G. Salles, Rituximab and dose-dense chemotherapy for adults with Burkitt's lymphoma: a randomised, controlled, open-label, phase 3 trial. Lancet 387, 2402-2411 (2016).
5. J. Xie, H. Zhang, K. Yea, R. A. Lerner, Autocrine signaling based selection of combinatorial antibodies that transdifferentiate human stem cells. Proc Natl Acad Sci USA 110, 8099-8104 (2013).
6. R. Testi, J. H. Phillips, L. L. Lanier, T cell activation via Leu-23 (CD69). J Immunol 143, 1123-1128 (1989).
7. E. R. Quinn et al., The B-cell receptor of a hepatitis C virus (HCV)-associated non-Hodgkin lymphoma binds the viral E2 envelope protein, implicating HCV in lymphomagenesis. Blood 98, 3745-3749 (2001).
8. M. S. Khodadoust, N. Olsson, L. E. Wagar, O. A. Haabeth, B. Chen, K. Swaminathan, K. Rawson, C. L. Liu, D. Steiner, P. Lund, S. Rao, L. Zhang, C. Marceau, H. Stehr, A. M. Newman, D. K. Czerwinski, V. E. Carlton, M. Moorhead, M. Faham, H. E. Kohrt, J. Carette, M. R. Green, M. M. Davis, R. Levy, J. E. Elias, A. A. Alizadeh, Antigen presentation profiling reveals recognition of lymphoma immunoglobulin neoantigens. Nature 543, 723-727 (2017).
9. R. J. Bende, W. M. Aarts, R. G. Riedl, D. de Jong, S. T. Pals, C. J. van Noesel, Among B cell non-Hodgkin's lymphomas, MALT lymphomas express a unique antibody repertoire with frequent rheumatoid factor reactivity. J Exp Med 201, 1229-1241 (2005).
10. V. J. Craig, I. Arnold, C. Gerke, M. Q. Huynh, T. Wündisch, A. Neubauer, C. Renner, S. Falkow, A. Müller, Gastric MALT lymphoma B cells express polyreactive, somatically mutated immunoglobulins. Blood 115, 581-591 (2010).
11. A. A. Warsame, H. C. Aasheim, K. Nustad, G. Trøen, A. Tierens, V. Wang, U. Randen, H. P. Dong, S. Heim, A. Brech, J. Delabie, Splenic marginal zone lymphoma with VH1-02 gene rearrangement expresses poly- and self-reactive antibodies with similar reactivity. Blood 118, 3331-3339 (2011).
12. C. C. Chu, R. Catera, K. Hatzi, X. J. Yan, L. Zhang, X. B. Wang, H. M. Fales, S. L. Allen, J. E. Kolitz, K. R. Rai, N. Chiorazzi, Chronic lymphocytic leukemia antibodies with a common stereotypic rearrangement recognize non-muscle myosin heavy chain IIA. Blood 112, 5122-5129 (2008).
13. H. Zhang, E. Sturchler, J. Zhu, A. Nieto, P. A. Cistrone, J. Xie, L. He, K. Yea, T. Jones, R. Turn, P. S. Di Stefano, P. R. Griffin, P. E. Dawson, P. H. McDonald, R. A. Lerner, Autocrine selection of a GLP-1R G-protein biased agonist with potent antidiabetic effects. Nat Commun 6, 8918 (2015).
14. C. C. Yin, R. Luthra, Molecular detection of t(14;18)(q32;q21) in follicular lymphoma. Methods Mol Biol 999, 203-209 (2013).
15. K. L. Sachen et al., Self-antigen recognition by follicular lymphoma B-cell receptors. Blood 120, 4182-4190 (2012).

Example 2

Follicular Lymphoma

Lymphoma biopsy samples and patient mononuclear cell apheresis material were provided by N.N. Petrov Research Institute of Oncology (St. Petersburg, Russia) from a patient with advanced follicular lymphoma scheduled to receive high dose chemotherapy and ASCT. CD34+ HSC were isolated from apheresis material using anti-human CD34 microbeads and MACS cell separation technique as per the manufacturer's protocol (Miltenyi Biotech). Cell purity following MACS separation was >98% as determined by flow cytometry following staining of the purified cells with anti-CD34-PE conjugated (Miltenyi). The remaining mononuclear cell fraction was used for isolation of CD8 T cells. Both CD34+ cells and CD8 T cells were cryopreserved until use. Fresh and viable samples of lymphoma tissue obtained through biopsy were cut at 3-5 mm$^3$ pieces and implanted subcutaneously at multiple sites to four six week old female NOD SCID (CB17-Prkdc$^{scid}$/NcrCrl) (Laboratory Animals at the Institute of Cytology and Genetics, SB RAS).

Generation of Patient Specific Humanised Mice

Adult female NOD/SCID mice 5 weeks of age were acclimatized for at least a 7-day period and were myeloablated by sublethal whole body irradiation (325 rad) delivered by a Gammacell 40 Exactor (Best Theratronics). 18 mice were injected with 0.25×10$^6$ purified CD34+ HSC cells per animal in a total volume of 200 mkl of phosphate-buffered saline (PBS) via the tail vein. All engrafted mice were housed under BL-2 conditions and provided with autoclaved and water supplemented with Baytril (enrofloxacin).

Analysis of Immune Reconstitution of Patient Specific Humanised Mice

To measure the level of reconstitution with human immune cells following stem cell transplant, mice were bled via the mandibular route (cheek pouch) using a sterile lancet (Braintree Scientific). Approximately ~100 mkl of blood was collected each time in K$_2$EDTA coated BD microtainer capillary blood collector tubes (Fisher Scientific).

The tubes were spun down at 500 Xg for 5 minutes for separation of the plasma. The cell pellet was treated with ACK lysis buffer to lyse RBC and washed extensively with MACS buffer containing BSA (Miltenyi) to enrich for peripheral blood mononuclear cells (PBMC).

Human PBMC, used as controls during flow cytometry analysis (FACS), was purified from leukapheresis blood collars, following standard Ficoll density gradient centrifugation techniques. Immunophenotyping was performed by staining the mononuclear cells with flurochrome conjugated antibodies specific for different human immune cell surface markers (e.g., CD45, CD3, CD19, CD4, CD8, etc.) followed by multi-colour flow cytometry using a LSRII Flow Cytometr (Becton Dickinson, NJ). Antibodies were obtained from eBioscience, Biolegend or BD Biosciences. During FACS, cell gating was done on viable lymphoid cells based on the forward and side scatter profile and most analysis performed on cells within the lymphoid gate.

A comparison between the percentages of human CD45$^+$ and endogenous mouse CD45$^+$ was performed to measure the level of immune reconstitution in mice. Background staining was determined using the corresponding isotype controls or staining cells isolated from unengrafted animals. Data was analyzed using the FlowJo software version 7.6.5 (Tree Star).

Figure 9:
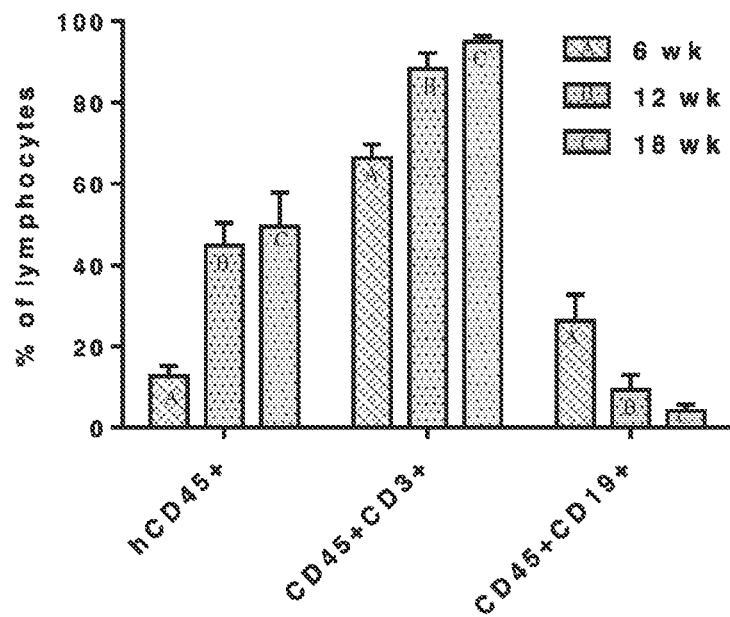
FIG. 9 shows percentages of hCD45+ lymphocytes, CD3+ T cells and CD19+ B cells in the lymphoid gate of PBMC at different time points following transplant.
Figure 10:
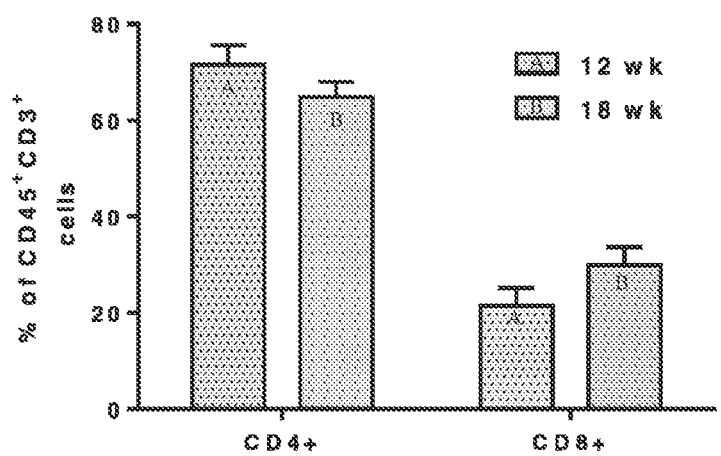
FIG. 10 shows percentages of CD4+ and CD8+ human T cell subsets in the PBMC at different time points following transplant.
Figure 11:
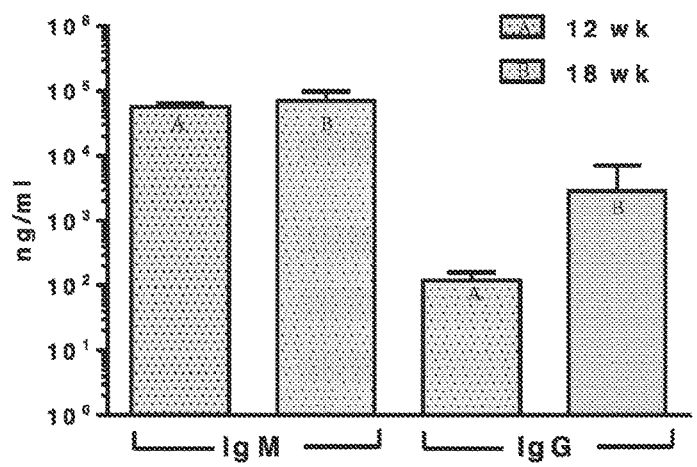
FIG. 11 shows levels of human IgM and IgG in humanized mice plasma at different time points following transplant.

The electrochemiluminiscent based MSD platform (Meso Scale Discovery, Gaithersburg, MD) was used to measure specific levels of human IgM and IgG in the plasma of mice at specific time points post transplantation. MSD 96-well High Bind Multi-Array plates were coated with 5 mkl of either anti-human IgM or anti-human IgG Fc (Bethyl Laboratories) at a concentration of 20 mkg/ml per well at 4° C. overnight. Plates were blocked with PBS/2% fetal bovine serum for 1 h followed by repeated washing with PBS/0.05% Tween-20. Mouse plasma samples were tested at 1:50-1:100 dilutions for human IgG levels and 1:500-1:1000 dilutions for human IgM levels in a total volume of 20 μl for each sample added per well in duplicates. Following incubation and washing as described earlier, 20 μl goat anti-human Ig antibody with SULFO-Tag at a concentration of 2 μg/ml per well was used as the detection Ab and plates incubated for 1 h at room temperature. Plates were developed by adding the appropriate substrate and read on the MSD Sector Imager 2400 according to the manufacturer's protocol. Human IgM and IgG standards (Bethyl Labs) was used to obtain the standard curve and human of Ig levels computed using GraphPad Prism program version 5. The results are summarized in FIGS. 9-11.

Identification of the BCR on the malignant B cell is specified in RU 2017134483. Autocrine-based selection of a ligand for the BCR on the malignant cells is specified in RU 2017134483. Lentiviral CAR T construct is specified in RU 2017134483.

CD8$^+$ T Cell Activation, Expansion and Transduction

Dynabeads CD8 Positive Isolation Kit (Life Technologies) was utilized for isolation of CD8 T cells from patient PBMCs fraction collected by apheresis. Human CD8 T cells were activated with CD3/CD28 beads at a 1:1 ratio (Life Technologies) in a complete RPMI media containing 40 IU/ml recombinant IL-2 for 72 hours. Activated T cells were re-suspended at concentration of 4 million cells per 3 ml of FL1-CART in lentiviral supernatant plus 1 ml of fresh RPMI media with 40 IU/ml IL-2 and cultured in 6-well plates. Plates were centrifuged at 1200×g for 90 minutes at 32° C. and then incubated for 4 hours at 37° C. Second and third transductions were performed two more times.

BCR Vaccination

In order to obtain the soluble form of patient follicular lymphoma BCR as a full-size antibody, VH and VL were cloned into the pFUSE antibody expression vectors (Invivogen) and produced utilizing FreeStyle 293 Expression System (Thermo Fisher Scientific). Protein was further purified and coupled to keyhole limpet hemocyanin using 0.1% glutaraldehyde as described by Levy (R. Levy. 1987 et al., Idiotype vaccination against murine B cell lymphoma. Humoral and cellular responses elicited by tumor-derived IgM and its molecular subunits. J Immunol. 139:2825.). Human IgG Isotype Control antibody (Invitrogen, cat 12000C) was conjugated to keyhole limpet hemocyanin as used as the control vaccine. Mice were immunized using subcutaneous injections with 0.1 ml with an emulsion of equal parts Freund's complete adjuvant and KLH-IgG at 100 mkg/ml in PBS.

Animal Experiments

All animal procedures were carried out in a strict accordance with the recommendations for proper use and care of laboratory animals (ECC Directive 86/609/EEC. All mouse surgical procedures and imaging were performed with the animals anesthetized by intramuscular injection of a 0.02 ml solution of 50% ketamine, 38% xylazine, and 12% acepromazine maleate. Patient B Cell FL tumor nodules were excised from female NOD SCID (CB17-Prkdc$^{scid}$/NcrCrl) mice, tumor fragments without evidence of necrosis were sliced to equal 3 mm$^3$ pieces and transplanted subcutaneously to sixteen NOD/SCID mice with reconstituted patient immune system at 18 w age. Tumor volume was measured with calipers and estimated using the formula $\pi/6\times(\text{length}\times \text{width}\times\text{height})$. Mice were divided into three experimental groups treated as follows:

Group 1: $3\times10^6$ FL1-CART intravenously at day 10 after transplant

Figure 12:
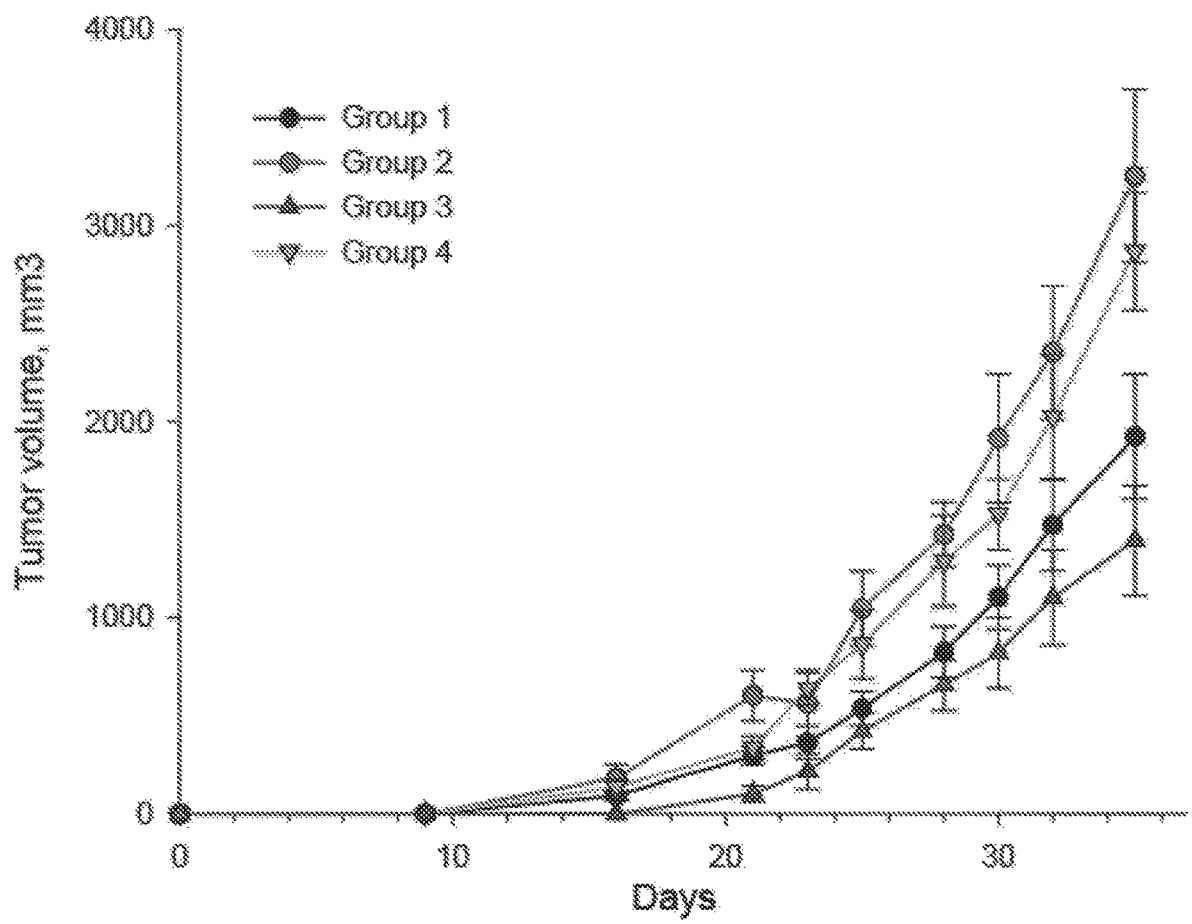
FIG. 12 shows tumor growth kinetics in experimental groups.
Figure 13:
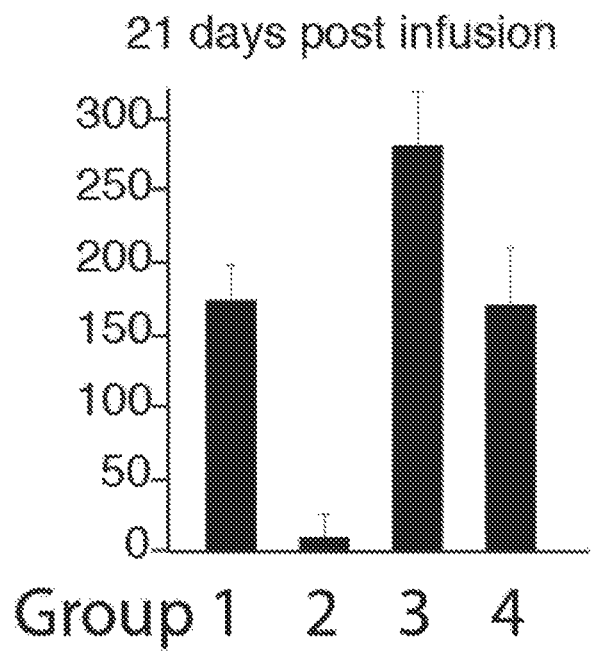
FIG. 13 shows quantity of CART cells on day 38.

Group 2: KLH-patient BCR vaccine subcutaneously at days 1, 5, 15 after transplant Group 3: $3\times10^6$ FL1-CART intravenously at day 10 after transplant+KLH- patient BCR vaccine subcutaneously at days 1, 5 and 15 after transplant Group 4: $3\times10^6$ FL1-CART intravenously at day 10 after transplant+KLH isotype control vaccine subcutaneously at days 1, 5 and 15 after transplant Animals were sacrificed at day 38 following transplant. Tumor growth kinetics in experimental groups are presented in FIG. 12.

Thus, the combination of intravenous FL1-CART therapy and vaccination using the patient BCR vaccine results in synergistic suppression of tumor growth. Opposite to that, the combination of intravenous FL1-CART therapy with isotype control vaccine reduces efficacy of FL1-CART therapy.

Flow Cytometry Analysis

On the 38th day after tumor inoculation (21st day post CART infusion), animals from each experimental group were used for isolation of blood. Erythrocytes were lysed with RBC lysis buffer (0.15 M $NH_4Cl$, 10 mM $NaHCO_3$, 0.1 mM EDTA). Chimeric FL-BCR expression was detected using synthetic ACILDLPKFCGGGS-Bio (SEQ ID NO: 29) cyclopeptide (GeneCust) and streptavidin conjugated with FITC (Thermo Fisher Scientific) and analyzed by Novocyte flow cytometer (ACEA Biosciences).

The combination of intravenous FL1-CART therapy and vaccination using patient BCR vaccine results in the highest levels of FL1-CART cells in circulation while concomitant vaccination with isotype control vaccine do not produce any synergy.

Meso-Scale Based Analysis of Specific Antibody Responses

MSD analysis of the terminal plasma samples were performed to measure antibody responses against the patient specific BCR and IgG Isotype Control Patient BCR antigen and Isotype Control antigens were coated on high bind MSD 96-well plates at concentrations between 20-50 mkg/ml with 5 mkl added per well and incubated overnight at 4° C. Plasma samples were tested at 1:80 dilution. Sulfo-tagged Anti-human Ig was used as the detection antibody and reaction developed using an electrochemiluminiscent (ECL) substrate and read in a MSD Sector Imager 2400 (Meso Scale Discovery).

TABLE 2

Anti BCR and Isotype Control antibody responses (MSD relative units) in immunized mice on day 38.

| | Group 1 | Group 2 | Group 3 | Group 4 |
|---|---|---|---|---|
| BCR | 700 ± 115 | 4700 ± 610 | 9700 ± 1550 | 1150 ± 175 |
| IgG Isotype Control | 690 ± 225 | 950 ± 170 | 1050 ± 135 | 3950 ± 375 |

MSD analysis of plasma reactivity to the respective antigens were measured and compared. Data is represented as mean+/−SEM. The combination of intravenous FL1-CART therapy and vaccination using patient BCR vaccine results in the highest levels of anti BCR reactivity versus BCR vaccine alone.

The data above clearly confirm the finding of substantial therapeutic synergy (tumor growth inhibition and level of personalized cancer antigen directed CAR T cells and immunoglobulins) between CAR T adoptive immunotherapy and vaccination wherein both targets same personalized cancer antigen.

NSCLC Harbouring EGFRvIII Mutation

To further confirm the observations, a patient with advanced NSCLC who was scheduled to undergo a cytoreductive surgery at Advanced Surgery Department of Kirov Academy of Military Medicine (St. Petersburg) and whose tumor tissue was positive for EGFRvIII mutation as confirmed by ICH staining of biopsy material was identified.

Epidermal growth factor receptor variant III (EGFRvIII) is the result of a novel tumor-specific gene rearrangement that produces a unique protein expressed in approximately 30% of gliomas, and certain other cancers including lung, breast and ovarian cancers. By deletion of a segment of the ligand-binding domain, EGFRvIII bypasses the need of ligand. This deletion spans exons 2-7, resulting in the introduction of a novel glycine residue at the fusion junction. While this mutant cannot bind ligands, it resides at the cell membrane and present a case of well-established personalized cancer model antigen harbouring a tumor specific mutation.

Two weeks prior to surgery patients were mobilized with 10 mkg/kg of GM-CSF (Neostim, Pharmsynthez) administered subcutaneously once a day for 5 consecutive days. Mobilized peripheral blood stem cells were collected on the Cobe Spectra Apheresis system. Approximately 3-6 blood volumes were processed during each daily collection, which lasted up to 11 hours. Patient underwent two daily apheresis procedures to collect $2\times10^6$ CD34+ cells per kg. CD34+ HSC were isolated from apheresis material using anti-human CD34 microbeads and MACS cell separation technique as per the manufacturer's protocol (Miltenyi Biotech). Cell purity following MACS separation was >98% as determined by flow cytometry following staining of the purified cells with anti-CD34-PE conjugated (Miltenyi). The remaining mononuclear cell fraction was used for isolation of CD8 T cells. Both CD34+ cells and CD8 T cells were cryopreserved until use. Fresh and viable samples of tumor tissue obtained during patient surgery were cut at 3-5 $mm^3$ pieces and implanted subcutaneously at multiple sites to four six week old female NOD SCID (CB17-Prkdc$^{scid}$/NcrCrl) (Laboratory Animals at the Institute of Cytology and Genetics, SB RAS).

Generation of Patient Specific Humanised Mice

Adult female NOD/SCID mice 5 weeks of age were acclimatized for at least a 7-day period and were myeloablated by sublethal whole body irradiation (325 rad) delivered by a Gammacell 40 Exactor (Best Theratronics). 18 mice were injected with $0.25\times10^6$ purified CD34+ HSC cells per animal in a total volume of 200 mkl of phosphate-buffered saline (PBS) via the tail vein. All engrafted mice were housed under BL-2 conditions and provided with autoclaved and water supplemented with Baytril (enrofloxacin).

Analysis of Immune Reconstitution

Figure 14:
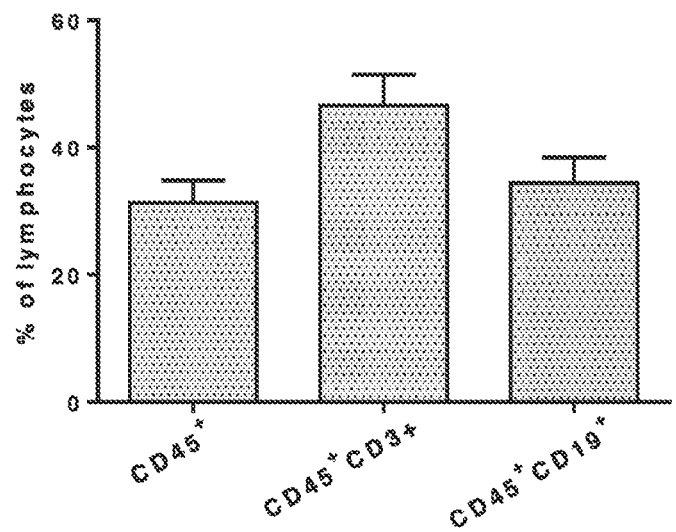
FIG. 14 shows levels of hCD45+ lymphocytes, CD3+ T cells and CD19+ B cells in the lymphoid gate in PBMC.
Figure 15:
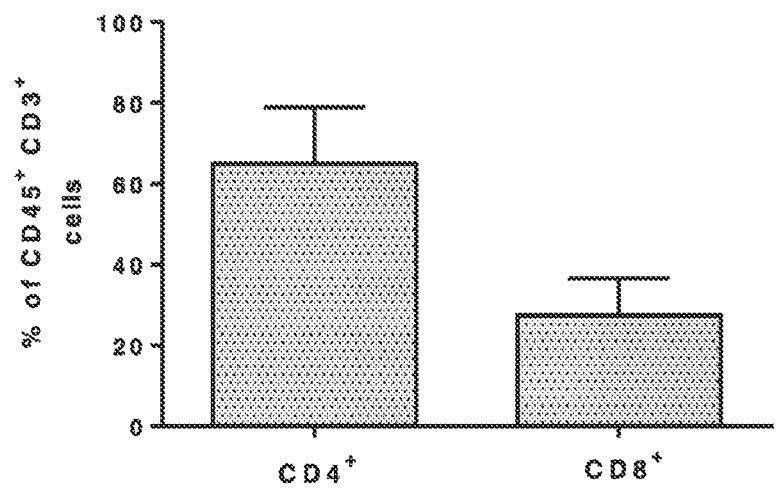
FIG. 15 shows percentages of CD4+ and CD8+ human T cell subsets in the PBMC.
Figure 16:
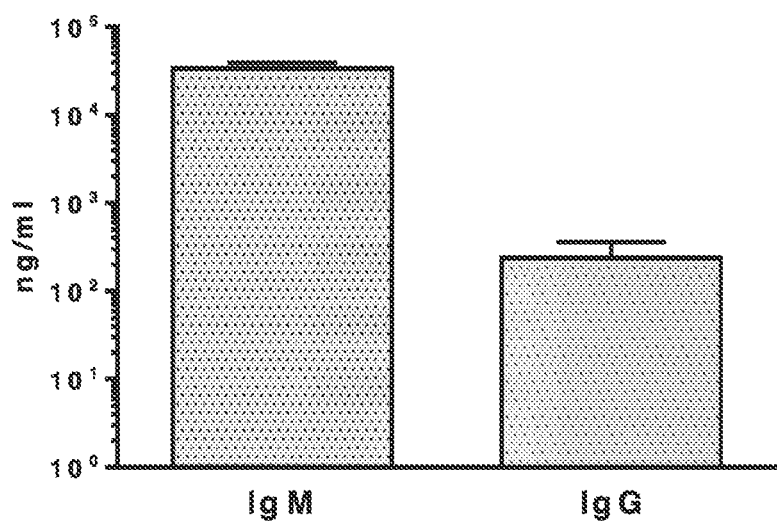
FIG. 16 shows levels of human IgM and IgG in mice plasma at different time points following transplant.
Figure 17:
FIG. 17 shows the CAR T lentiviral vector.

Analysis of immune reconstitution was performed as described above at 6, 12 and 18 wk. Data is presented in FIGS. 14-16.

CAR T Lentiviral Vector

A EGFRvIII targeting 139-scFv-based CAR vector was assembled using scFv sequence from human anti-EGFRvIII antibody 131 to T-cell signalling domains from CD28-41BB-CD3ζ as described by Rosenberg (Steven A. Rosenberg et al., Recognition of Glioma Stem Cells by Genetically Modified T Cells Targeting EGFRvIII and Development of Adoptive Cell Therapy for Glioma, *Hum Gene Ther.* 2012 October; 23(10): 1043-1053.) DNA fragment coding for CD28-41BB-CD3ζ was synthesized (GeneCust) and cloned into the pLV2 lentiviral vector (Clontech) under control of the EF1a promoter. The arrangement of genes is in the order of: IL2-signal sequence, 139-scFv, GGGS linker; a CD28 trans-membrane and intracellular region; intracellular domains of the OX-40 and CD3zetta. The lentiviruses were prepared by co-transfection of HEK293T cells with the pLV2-139-scFv-CD28-41BB-CD3zetta plasmid and the packaging plasmids ($2^{nd}$ generation). Supernatants containing the virus were collected at 48 h post transfection. The titer of lentivirus preparations was determined using Lenti-X p24 ELISAs (Clontech).

$CD8^+$ T Cell Activation, Expansion and Transduction

Dynabeads CD8 Positive Isolation Kit (Life Technologies) was utilized for isolation of CD8 T cells from patient PBMCs fraction collected by apheresis. Human CD8 T cells were activated with CD3/CD28 beads at a 1:1 ratio (Life Technologies) in a complete RPMI media containing 40 IU/ml recombinant IL-2 for 72 hours. Activated T cells were re-suspended at concentration of 4 million cells per 3 ml of CD28-41BB-CD3ζ-CAR in lentiviral supernatant plus 1 ml of fresh RPMI media with 40 IU/ml IL-2 and cultured in 6-well plates. Plates were centrifuged at 1200×g for 90 minutes at 32° C. and then incubated for 4 hours at 37° C. Second and third transductions were performed two more times.

Vaccination 14-amino acid peptide corresponding to the amino acid sequence at the fusion junction (LEEKKGNYVVTDHC) (SEQ ID NO: 30), was synthesized, purified, and coupled to keyhole limpet hemocyanin as described by Bigner (Monoclonal Antibodies against EGFRvIII are Tumor Specific and React with Breast and Lung Carcinomas and Malignant Gliomas. Darell D. Bigner et al., Cancer Res. 1995 Jul. 15; 55(14):3140-8.). LEEKKGNYVVTDHC (SEQ ID NO: 30) is an epitope recognized by antibody 139, used for engineering of 139-scFv-based CAR. Mice were immunized using subcutaneous injections with 0.1 ml with an emulsion of equal parts Freund's complete adjuvant and KLH-LEEK at 100 mkg/ml in PBS.

Animal Experiments

Figures 18, 19:
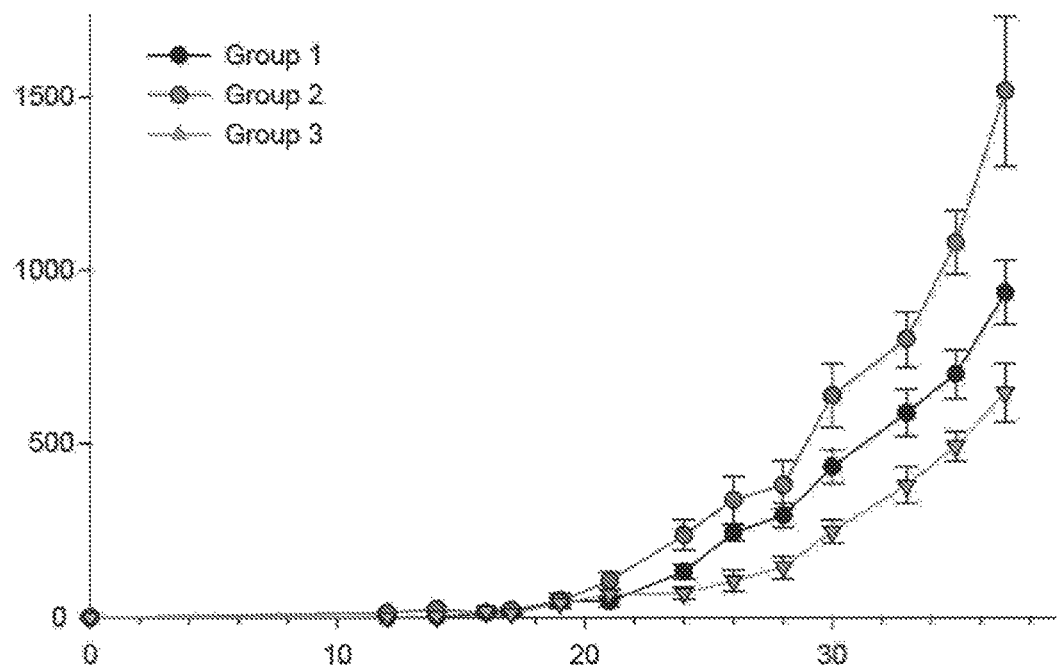
FIG. 18 shows tumor growth kinetics in experimental groups.
FIG. 19 shows NNK coding moiety flanked by Cysteines used in the Phage Display Cyclopeptide Library Kit used in Example 3. The sequences from top to bottom correspond to SEQ ID NOs: 38, 39, and 40.

All animal procedures were carried out in a strict accordance with the recommendations for proper use and care of laboratory animals (ECC Directive 86/609/EEC. All mouse surgical procedures and imaging were performed with the animals anesthetized by intramuscular injection of a 0.02 ml solution of 50% ketamine, 38% xylazine, and 12% acepromazine maleate. Patient NSCLC tumor nodules were excised from female NOD SCID (CB17-Prkdc$^{scid}$/NcrCrl) mice, tumor fragments without evidence of necrosis were sliced to equal 3 $mm^3$ pieces and transplanted subcutaneously to fifteen NOD/SCID mice with reconstituted patient immune system at 18 w age. Tumor volume was measured with calipers and estimated using the formula π/6×(length× width×height). Mice were divided into three experimental groups treated as follows:

Group 1: 3×$10^6$ CD28-41BB-CD3ζ-CART intravenously at day 10 after transplant
Group 2: KLH-LEEK vaccine subcutaneously at days 1, 5, 15 after transplant
Group 3: 3×$10^6$ CD28-41BB-CD3ζ-CART intravenously at day 10 after transplant+
KLH-LEEK vaccine subcutaneously at days 1, 5 and 15 after transplant Animals were sacrificed at day 38 following transplant. Tumor growth kinetics in experimental groups is presented in FIG. 18.

The data confirm the finding of substantial therapeutic synergy between CAR T adoptive immunotherapy and vaccination wherein both targets same personalized cancer antigen.

Example 3

Method for Identification of B Cell Receptor Ligand by Phage Display

As a general alternative to the Reporter Cells a phage-displayed cyclopeptide library panning may be performed for identification of the malignant BCR specific moiety. Commercially available phage-peptide libraries such as New England Biolabs Ph.D.-7 and Ph.D.-12 libraries may be utilized. For randomization Ph.D.™-C7C Phage Display Cyclopeptide Library Kit uses NNK coding moiety flanked by Cysteines shown in FIG. 19. Herein, we provide modified NEB protocol for a malignant BCR specific peptides identification. It is recommended to perform negative-selection incubation during each round of panning.

Panning procedure:

1. Inoculate 10 ml of LB+Tet medium with ER2738, for use in titering. If amplifying the eluted phage on the same day, also inoculate 20 ml of LB medium in a 250-ml Erlenmeyer flask (do not use a 50-ml conical tube) with ER2738. Incubate both cultures at 37° C. with vigorous shaking. ER2738 is *E. coli* host strain F' proA+B+ lacIq Δ(lacZ)M15 zzf::Tn10(TetR)/fhuA2 glnV Δ(lac-proAB) thi-1 Δ(hsdS-mcrB)5.
2. Transfer 50 μl of a 50% aqueous suspension of affinity beads appropriate for capture of the antibody to a microfuge tube. Add 1 ml of TBS+0.1% Tween (TBST). Suspend the resin by tapping the tube.
3. Pellet the resin by magnetic capture. Carefully pipette away and discard the supernatant.
4. Suspend the resin in 1 ml of blocking buffer (0.1 M NaHCO3 (pH 8.6), 5 mg/ml BSA, 0.02% NaN3 (optional). Filter sterilize, store at 4° C.).
5. Incubate for 60 minutes at 4° C., mixing occasionally.
6. In the meantime, mix the 2×$10^9$ phages with 2 mkg of a negative-selection antibody to a final volume of 200 μl with TBST.
7. Incubate for 20 minutes at room temperature.
8. Following the blocking reaction in Step 4, pellet the resin as in Step 3 and wash 4 times with 1 ml of TBST, pelleting the resin each time.
9. Resuspend resing in 1 ml and aliquote to a two separate tubes (500 mkl each).
10. Transfer the phage-neg-antibody mixture to the first tube containing the washed resin. Mix gently and incubate for 15 minutes at room temperature, mixing occasionally.
11. Pellet the resin as in Step 3, collect the supernatant.
12. Mix the supernatant with 2 mkg of the malignant BCR antibody.
13. Incubate for 20 minutes at room temperature.
14. Pellet the resin as in Step 3, discard the supernatant, and wash 10 times with 1 ml of TBST, pelleting the resin each time.

15. Elute the bound phage by suspending the resin in 1 ml of Glycine Elution Buffer (0.2 M Glycine-HCl, pH 2.2, 1 mg/ml BSA).
16. Incubate for 10 minutes at room temperature.
17. Pellet resin by magnetization for 1 minute.
18. Carefully transfer the supernatant to a new microfuge tube, taking care not to disturb the pelleted resin.
19. Immediately neutralize the eluate with 150 µl of 1 M Tris-HCl, pH 9.1.
20. Amplify the remaining eluate by adding it to the 20 ml ER2738 culture from Step 1 (must be early-log; no later) and incubating at 37° C. with vigorous shaking for 4.5 hours.
21. Transfer the culture to a centrifuge tube and spin for 10 minutes at 12,000 g at 4° C. Transfer the supernatant to a fresh tube and re-spin (discard the pellet).
22. Pipette the upper 80% of the supernatant to a fresh tube and add to it ⅙ volume of 20% PEG/2.5 M NaCl.
23. Allow the phage to precipitate at 4° C. for 2 hours or overnight.
24. Spin the PEG precipitation at 12,000 g rpm for 15 minutes at 4° C.
25. Decant and discard the supernatant, respin briefly, and remove the residual supernatant with a pipette.
26. Suspend the pellet in 1 ml of TBS. Transfer the suspension to a tube and spin for 5 minutes at 4° C. to pellet residual cells.
27. Transfer the supernatant to a fresh microcentrifuge tube and reprecipitate with ⅙ volume of 20% PEG/2.5 M NaCl.
28. Incubate for 15-60 minutes on ice.
29. Microcentrifuge at 14,000 rpm for 10 minutes at 4° C.
30. Discard the supernatant, respin briefly, and remove residual supernatant with a micropipet.
31. Suspend the pellet in 200 µl of TBS.
32. Microcentrifuge at 14,000 rpm for 1 minute to pellet any remaining insoluble matter.
33. Transfer the supernatant to a fresh tube. This is the amplified eluate.
34. Perform a second and third rounds of panning.

Plaque Amplification for ELISA and Sequencing:
1. Dilute an overnight culture of ER2738 1:100 in LB. Dispense 1 ml of diluted culture into 96-well deepwell plates (#260251, Thermo Scientific). For each antibody to be characterized use 2 plates.
2. Stab a blue plaque from a phage plates.
3. Use a microplate tape sealer to cover the plates.
4. Incubate the plates at 37° C. with shaking for 4.5-5 hours.
5. Centrifuge plates at 250 g for 10 minutes at RT.
6. Carefully collect 700 mkl of the supernatant and transfer to a fresh plate.
7. This is the amplified phage stock and can be stored at 4° C. for two days.

Phage ELISA Binding Assay:
1. Coat ELISA plate wells with 100 µl of 100 µg/ml of malignant BCR antibody or negative-control antibody in 0.1 M NaHCO₃, pH 8.6.
2. Incubate overnight at 4° C.
3. Wash each plate 5 times with TBST.
4. Block ELISA plate wells by 5% Milk in PBST.
5. Incubate 1 hour at RT.
6. Wash each plate 5 times with TBST.
7. In the separate blocked plate, carry out fourfold serial dilutions of the phage supernatant.
8. Using a multichannel pipettor, transfer 100 µl from each row of diluted phage to a row of antibody-coated wells.
9. Incubate at RT for 2 hours with agitation.
10. Wash each plate 5 times with TBST.
11. Dilute HRP-conjugated anti-M13 monoclonal antibody (GE Healthcare. #27-9421-01) in blocking buffer to the final dilution recommended by the manufacturer. Add 200 µl of diluted conjugate to each well.
12. Incubate at RT for 1 hour with agitation.
13. Add 50 µl of substrate solution to each well, and incubate for 10-60 minutes at room temperature with gentle agitation.
14. Read the plates using a microplate reader set at 415 nm. For each phage clone, compare the signals obtained with negative-control and malignant BCR antibody.

Sequencing of Phage DNA:
1. Transfer 500 µl of the phage-containing supernatant to a fresh microfuge tube.
2. Add 200 µl of 20% PEG/2.5 M NaCl. Invert several times to mix, and let stand for 10-20 minutes at room temperature.
3. Microfuge at 14,000 rpm for 10 minutes at 4° C. and discard the supernatant. Phage pellet may not be visible.
4. Re-spin briefly. Carefully pipet away and discard any remaining supernatant.
5. Suspend the pellet thoroughly in 100 µl of Iodide Buffer by vigorously tapping the tube.
6. Add 250 µl of ethanol.
7. Incubate 10-20 minutes at room temperature.
8. Spin in a microfuge at 14,000 rpm for 10 minutes at 4° C.
9. Discard the supernatant.
10. Wash the pellet with 0.5 ml of ice-cold 70% ethanol.
11. Suspend the pellet in 30 µl of TE buffer.
12. Use 5 µl of the DNA in TE buffer as a template for sequencing.
13. Use the reverse primer for DNA sequencing (GCA ATG CGA TTG ATA CTC CC (SEQ ID NO: 41)).

Results of the panning are shown in the following tables. For the display the full-size follicular lymphoma BCR in IgG1 format was used. Patent FL1 is as described in Example 1.

Figure 20:
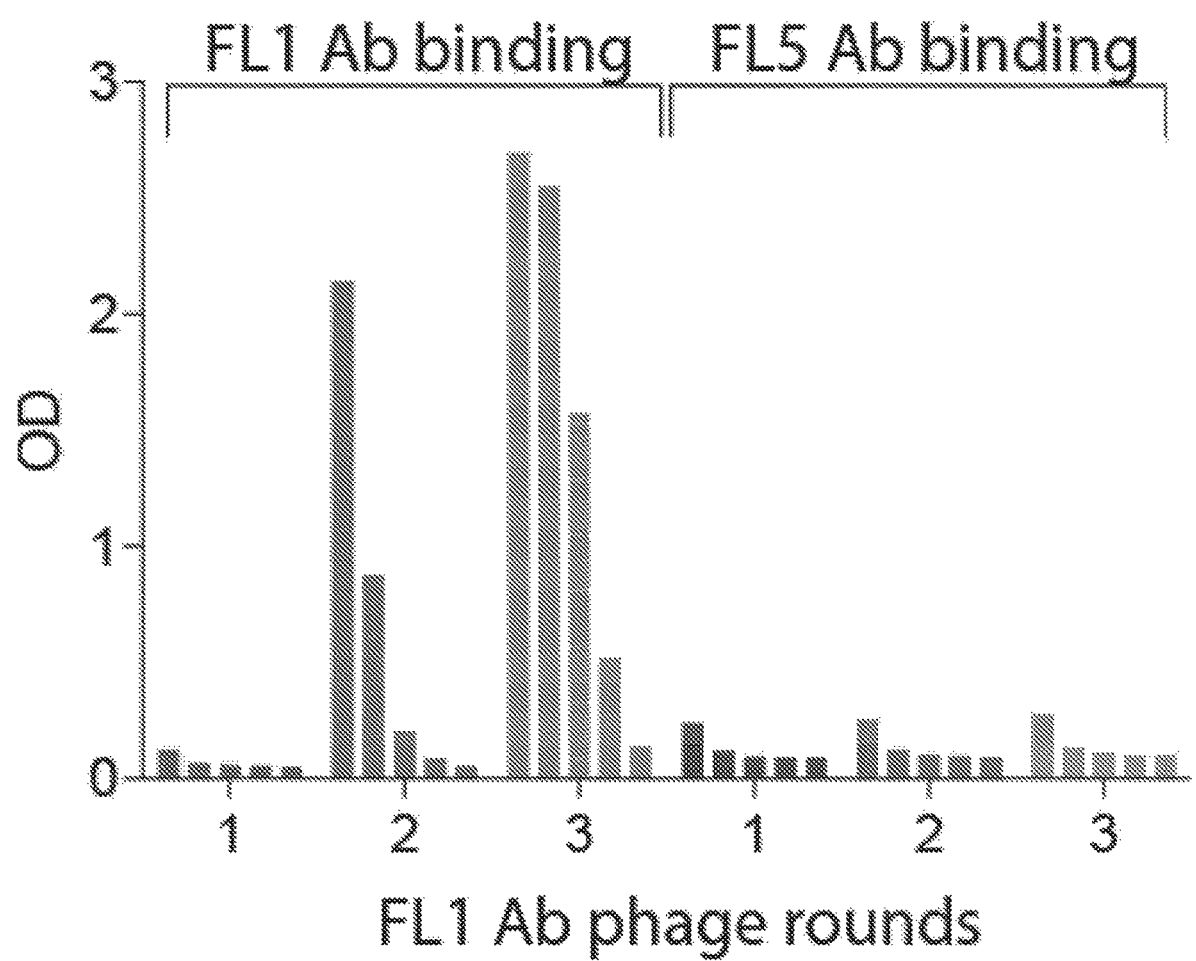
FIG. 20 shows ELISA results for the binding of phages resulting from I-III rounds of panning as described in Example 3 against the BCR of patient FL1 with the BCR of patients FL1 and FL5. Phage concentrations are, from left to right, 5, 2.5, 1.25, 0.63, and 0.31 mk/well for each round of panning for each antibody shown.

Table 3 shows ELISA results for the binding of amplified phages resulting from I-III rounds of panning against the BCR of patient FL1 with the BCR of patients FL1 and FL5 at the phage concentrations shown. Results are also shown in FIG. 20.

| Phages amount | FL1 Ab FL1 Ab phage rounds | | | FL5 Ab FL1 Ab phage rounds | | |
|---|---|---|---|---|---|---|
| mkl/well | 1 | 2 | 3 | 1 | 2 | 3 |
| 5 | 0.1234 | 2.1417 | 2.6927 | 0.2405 | 0.2538 | 0.2753 |
| 2.50 | 0.0656 | 0.873 | 2.5545 | 0.122 | 0.1241 | 0.133 |
| 1.25 | 0.0577 | 0.2054 | 1.5719 | 0.093 | 0.1014 | 0.1127 |
| 0.63 | 0.0534 | 0.0868 | 0.5184 | 0.092 | 0.0948 | 0.0982 |
| 0.31 | 0.0523 | 0.056 | 0.1392 | 0.091 | 0.0901 | 0.1 |

Table 4 shows ELISA results for the binding of phages from individual plaques after III rounds of panning against the BCR of patient FL1 with the BCR of patient FL1.

|   | 1 | 2 | 3 | 4 | 5 | 6 | 7 | 8 | 9 | 10 | 11 | 12 |
|---|---|---|---|---|---|---|---|---|---|---|---|---|
| A | 0.063 | 2.024 | 1.313 | 1.305 | 1.132 | 0.683 | 0.908 | 0.718 | 0.142 | 0.379 | 0.225 | 0.098 |
| B | 0.054 | 0.053 | 0.117 | 0.073 | 1.013 | 0.068 | 1.135 | 0.436 | 0.1 | 0.062 | 0.537 | 0.695 |
| C | 1.015 | 0.054 | 0.495 | 0.743 | 0.639 | 0.456 | 0.076 | 0.213 | 0.061 | 0.728 | 0.626 | 0.639 |
| D | 0.055 | 0.783 | 0.808 | 0.522 | 0.754 | 0.43 | 0.513 | 0.443 | 0.499 | 0.27 | 0.147 | 0.519 |
| E | 1.444 | 0.682 | 0.564 | 0.592 | 0.08 | 0.42 | 0.519 | 0.088 | 0.111 | 0.368 | 0.316 | 0.055 |
| F | 0.871 | 0.371 | 0.627 | 0.604 | 0.491 | 0.159 | 0.371 | 0.128 | 0.316 | 0.241 | 0.12 | 0.647 |
| G | 0.794 | 0.909 | 0.573 | 0.453 | 0.484 | 0.435 | 0.136 | 0.379 | 0.598 | 0.517 | 0.525 | 0.501 |
| H | 0.079 | 1.229 | 0.205 | 0.415 | 1.459 | 0.36 | 0.231 | 0.12 | 0.075 | 0.522 | 0.409 | 0.091 |

Table 5 shows ELISA results for the binding of phages from individual plaques after III rounds of panning against the BCR of patient FL1 with the BCR of patient FL5.

|   | 1 | 2 | 3 | 4 | 5 | 6 | 7 | 8 | 9 | 10 | 11 | 12 |
|---|---|---|---|---|---|---|---|---|---|---|---|---|
| A | 0.081 | 0.076 | 0.056 | 0.074 | 0.108 | 0.073 | 0.088 | 0.124 | 0.088 | 0.063 | 0.064 | 0.074 |
| B | 0.059 | 0.066 | 0.077 | 0.102 | 0.117 | 0.063 | 0.079 | 0.067 | 0.097 | 0.062 | 0.093 | 0.211 |
| C | 0.121 | 0.085 | 0.091 | 0.161 | 0.074 | 0.091 | 0.058 | 0.091 | 0.059 | 0.068 | 0.093 | 0.204 |
| D | 0.073 | 0.123 | 0.097 | 0.088 | 0.098 | 0.101 | 0.083 | 0.08 | 0.071 | 0.066 | 0.064 | 0.196 |
| E | 0.067 | 0.134 | 0.101 | 0.068 | 0.067 | 0.086 | 0.092 | 0.067 | 0.058 | 0.141 | 0.095 | 0.061 |
| F | 0.082 | 0.276 | 0.118 | 0.109 | 0.064 | 0.08 | 0.059 | 0.059 | 0.065 | 0.118 | 0.068 | 0.092 |
| G | 0.179 | 0.188 | 0.106 | 0.129 | 0.087 | 0.143 | 0.063 | 0.106 | 0.108 | 0.106 | 0.227 | 0.127 |
| H | 0.102 | 0.083 | 0.118 | 0.15 | 0.133 | 0.076 | 0.08 | 0.13 | 0.06 | 0.119 | 0.117 | 0.149 |

The positive clones from Table 4 were amplified and sequenced. The sequence, location on Table 4, and OD are shown below in Table 6. The peptide identified as binding the BCR of patient FL1 was also identified as a BCR ligand in Example 1 using the autocrine signaling method.

TABLE 6

|   | Sequence (SEQ ID NO: 42) | Position | OD |
|---|---|---|---|
| 1 | ILDLPKF | C1 | 1.02 |
| 2 | ILDLPKF | E1 | 1.44 |
| 3 | ILDLPKF | A2 | 2.02 |
| 4 | ILDLPKF | H2 | 1.23 |
| 5 | ILDLPKF | A3 | 1.31 |
| 6 | ILDLPKF | A4 | 1.31 |
| 7 | ILDLPKF | A5 | 1.13 |
| 8 | ILDLPKF | B5 | 1.01 |
| 9 | ILDLPKF | H5 | 1.46 |
| 10 | ILDLPKF | B7 | 1.14 |

After the cyclopeptide specific for the FL1 patient's BCR was identified, as shown in Table 6, the sequence was cloned into a 3-generation CAR lentiviral vector. Two complementary primers coding for the selected cyclopeptide flaked by EcoRI and NheI cloning sites were synthesized.

```
Primer FL1peptide FW
                                      (SEQ ID NO: 43)
TCACGAATTCGGCTTGTATTCTTGATTTGCCGA

AGTTTTGCGGTGGAGGTTCGGCTAGC
```

```
Primer FL1peptide Rev
                                      (SEQ ID NO: 44)
GCTCGCTAGCCGAACCTCCACCGCAAAACTTCG

GCAAATCAAGAATACA
```

After amplification the PCR product was cloned into the pLV2-Fc-CAR vector at the EcoRI and NheI restriction sites.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of treating lymphoma in a human subject comprising:
   - identifying a unique B cell receptor expressed in clonally related malignant lymphoma cells of the subject;
   - modifying a population of T cells by introducing nucleic acid molecules encoding the the unique B cell receptor and nucleic acid molecules encoding a library of CARs wherein each CAR within the library comprises extracellular antigen binding domain comprising a distinct putative ligand of a unique B cell receptor, wherein the T cells co-express the unique B cell receptor and a CAR from the library on the cell surface;
   - measuring activation of the T cells in response to autocrine CAR signaling induced by binding of the putative ligand of the CAR to the co-expressed unique B cell receptor, thereby identifying a ligand of the unique B cell receptor ligand; and
   - administering to the subject a therapeutically effective amount of the ligand of the unique B cell receptor coupled to an immunotherapeutic agent, wherein the putative ligand of the unique B cell receptor is a peptide, a cyclopeptide, or a VHH.

2. The method of claim 1, wherein the putative ligand of the unique B cell receptor is a peptide.

3. The method of claim 2, wherein the putative ligands of the unique B cell receptor comprise VHH antigen binding domains.

4. The method of claim 1, wherein measuring activation of the T cells comprises measuring expression of CD69 or CD25.

5. The method of claim 1, wherein the subject is determined to have lymphoma and wherein the subject is determined to have one or more single-nucleotide polymorphisms (SNPs) associated with lymphoma.

6. The method of claim 1, wherein identifying the unique B cell receptor expressed in lymphoma cells of the subject comprises:
  obtaining B cells from a biopsy from the subject;
  extracting RNA from the cells;
  synthesizing cDNA from the extracted RNA;
  amplifying the variable region genes of heavy and light Ig chains;
  sequencing the variable region genes; and
  identifying the unique B cell receptor based on the sequencing of the variable region genes from the B cells.

7. The method of claim 1, wherein identifying the unique B cell receptor expressed in lymphoma cells of the subject comprises cloning and sequencing variable region genes of heavy and light Ig chains from circulating cell free DNA obtained from the subject and identifying the unique B cell receptor based on the sequencing of the variable region genes.

8. The method of claim 1, wherein the method is performed in 3 weeks or less.

9. The method of claim 1, wherein the ligand of the unique B cell receptor coupled to an immunotherapeutic agent is a CART cell wherein the extracellular domain of the CAR comprises the ligand of the unique B cell receptor.

10. The method of claim 1, wherein the subject is administered the unique B cell receptor, or a fragment thereof that binds to the ligand, concomitantly with the ligand of the unique B cell receptor that is coupled to the immunotherapeutic agent.

* * * * *